US011382642B2

United States Patent
Robertson et al.

(10) Patent No.: US 11,382,642 B2
(45) Date of Patent: *Jul. 12, 2022

(54) ROTATABLE CUTTING IMPLEMENTS WITH FRICTION REDUCING MATERIAL FOR ULTRASONIC SURGICAL INSTRUMENTS

(71) Applicant: Cilag GmbH International, Zug (CH)

(72) Inventors: Galen C. Robertson, Apex, NC (US); Richard W. Timm, Cincinnati, OH (US); Kip M. Rupp, New Richmond, OH (US); Kristina A. Snyder, West Chester, PA (US)

(73) Assignee: Cilag GmbH International, Zug (CH)

( * ) Notice: Subject to any disclaimer, the term of this patent is extended or adjusted under 35 U.S.C. 154(b) by 366 days.

This patent is subject to a terminal disclaimer.

(21) Appl. No.: 16/420,772

(22) Filed: May 23, 2019

(65) Prior Publication Data

US 2019/0274700 A1 Sep. 12, 2019

Related U.S. Application Data

(62) Division of application No. 15/249,860, filed on Aug. 29, 2016, now Pat. No. 10,299,810, which is a (Continued)

(51) Int. Cl.
*A61B 17/32* (2006.01)
*A61B 17/22* (2006.01)
*A61B 17/3207* (2006.01)

(52) U.S. Cl.
CPC .... *A61B 17/2202* (2013.01); *A61B 17/22004* (2013.01); *A61B 17/3207* (2013.01);
(Continued)

(58) Field of Classification Search
CPC ..... A61B 17/22; A61B 17/32; A61B 17/3207; A61B 17/320068; A61B 17/22004; A61B 17/320783; A61B 2017/320072
See application file for complete search history.

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| CA | 2535467 A1 | 4/1993 |
| CN | 2460047 Y | 11/2001 |

(Continued)

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
(Continued)

*Primary Examiner* — Vi X Nguyen

(57) ABSTRACT

An ultrasonic surgical instrument is disclosed. The ultrasonic surgical instrument includes a housing, an ultrasonic transducer assembly to selectively generate ultrasonic motion, a motor within the housing, an outer sheath coupled to the housing, and a blade operably coupled to the ultrasonic transducer assembly and rotatably supported within the outer sheath for rotation with the ultrasonic transducer assembly. The ultrasonic transducer assembly is rotatably supported within the housing. The motor is configured to selectively apply a rotary motion to the ultrasonic transducer assembly. The outer sheath includes a distal tip portion defining a tip cavity. The blade includes a tissue-cutting
(Continued)

distal end rotatably supported within the tip cavity. A portion of the tissue-cutting distal end is configured to apply the ultrasonic motion to tissue.

7 Claims, 44 Drawing Sheets

Related U.S. Application Data division of application No. 13/891,269, filed on May 10, 2013, now Pat. No. 9,427,249, which is a division of application No. 12/703,875, filed on Feb. 11, 2010, now Pat. No. 8,469,981.

(52) U.S. Cl.
CPC ............... *A61B 17/320068* (2013.01); *A61B 17/320783* (2013.01); *A61B 2017/22011* (2013.01); *A61B 2017/32007* (2017.08); *A61B 2017/320069* (2017.08); *A61B 2017/320089* (2017.08)

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Helges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Perstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |

(56) References Cited

U.S. PATENT DOCUMENTS

| | | |
|---|---|---|
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |

(56) References Cited

U.S. PATENT DOCUMENTS

| | | |
|---|---|---|
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatia |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tai et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |

(56) References Cited

U.S. PATENT DOCUMENTS

| | | |
|---|---|---|
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Eanko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,241,724 B1 | 6/2001 | Fleischman et al. |

(56) References Cited

U.S. PATENT DOCUMENTS

| | | |
|---|---|---|
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |

(56) References Cited

U.S. PATENT DOCUMENTS

| | | |
|---|---|---|
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |

(56) References Cited

U.S. PATENT DOCUMENTS

| | | |
|---|---|---|
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Ratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |

(56) References Cited

U.S. PATENT DOCUMENTS

| | | |
|---|---|---|
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |

(56) References Cited

U.S. PATENT DOCUMENTS

| | | |
|---|---|---|
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,055,208 B2 | 11/2011 | Lilia et al. |
| 8,056,720 B2 | 11/2011 | Hawkes |
| 8,056,787 B2 | 11/2011 | Boudreaux et al. |
| 8,057,468 B2 | 11/2011 | Esky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |

(56) References Cited

U.S. PATENT DOCUMENTS

| | | |
|---|---|---|
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisei |
| 8,382,775 B1 | 2/2013 | Bender et al. |
| 8,382,782 B2 * | 2/2013 | Robertson ...... A61B 17/320092 606/169 |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stabler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |

(56) References Cited

U.S. PATENT DOCUMENTS

| | | |
|---|---|---|
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,521,331 B2 | 8/2013 | Itkowitz |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |

(56) References Cited

U.S. PATENT DOCUMENTS

| | | |
|---|---|---|
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |

(56) References Cited

U.S. PATENT DOCUMENTS

| | | |
|---|---|---|
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 * | 2/2016 | Robertson ......... A61B 17/22004 |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |

(56) References Cited

U.S. PATENT DOCUMENTS

| | | |
|---|---|---|
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,118 B2 | 8/2017 | Schulte et al. |
| 9,724,120 B2 | 8/2017 | Faller et al. |
| 9,724,152 B2 | 8/2017 | Horiie et al. |
| 9,730,695 B2 | 8/2017 | Leimbach et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,802,033 B2 | 10/2017 | Hibner et al. |
| 9,808,246 B2 | 11/2017 | Shelton, IV et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,878,184 B2 | 1/2018 | Beaupre |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,901,321 B2 | 2/2018 | Harks et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,656 B2 | 3/2018 | Stulen |
| 9,913,680 B2 | 3/2018 | Voegele et al. |
| 9,918,730 B2 | 3/2018 | Trees et al. |
| 9,925,003 B2 | 3/2018 | Parihar et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,974,539 B2 | 5/2018 | Yates et al. |
| 9,987,033 B2 | 6/2018 | Neurohr et al. |
| 10,004,526 B2 | 6/2018 | Dycus et al. |
| 10,004,527 B2 | 6/2018 | Gee et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,070,916 B2 | 9/2018 | Artale |
| 10,080,609 B2 | 9/2018 | Hancock et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,699 B2 | 10/2018 | Boudreaux |
| 10,111,703 B2 | 10/2018 | Cosman, Jr. et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,154,848 B2 | 12/2018 | Chernov et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,179,022 B2 | 1/2019 | Yates et al. |
| 10,188,455 B2 | 1/2019 | Hancock et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,263,171 B2 | 4/2019 | Wiener et al. |
| 10,265,117 B2 | 4/2019 | Wiener et al. |
| 10,265,118 B2 | 4/2019 | Gerhardt |
| 10,271,840 B2 | 4/2019 | Sapre |
| 10,278,721 B2 | 5/2019 | Dietz et al. |
| 10,285,724 B2 | 5/2019 | Faller et al. |
| 10,285,750 B2 | 5/2019 | Coulson et al. |
| 10,299,810 B2 | 5/2019 | Robertson et al. |
| 10,299,821 B2 | 5/2019 | Shelton, IV et al. |
| 10,314,579 B2 | 6/2019 | Chowaniec et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,602 B2 | 7/2019 | Strobl et al. |
| 10,342,606 B2 | 7/2019 | Cosman et al. |
| 10,349,999 B2 | 7/2019 | Yates et al. |
| 10,357,303 B2 | 7/2019 | Conlon et al. |
| 10,363,084 B2 | 7/2019 | Friedrichs |
| 10,376,305 B2 | 8/2019 | Yates et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,413,353 B2 | 9/2019 | Kerr et al. |
| 10,420,579 B2 | 9/2019 | Wiener et al. |
| 10,420,607 B2 | 9/2019 | Woloszko et al. |

(56) References Cited

U.S. PATENT DOCUMENTS

| | | |
|---|---|---|
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,986 B2 | 10/2019 | Zikorus et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,485,607 B2 | 11/2019 | Strobl et al. |
| 10,492,849 B2 | 12/2019 | Juergens et al. |
| 10,507,033 B2 | 12/2019 | Dickerson et al. |
| 10,512,795 B2 | 12/2019 | Voegele et al. |
| 10,517,627 B2 | 12/2019 | Timm et al. |
| 10,524,787 B2 | 1/2020 | Shelton, IV et al. |
| 10,524,854 B2 | 1/2020 | Woodruff et al. |
| 10,524,872 B2 | 1/2020 | Stewart et al. |
| 10,537,351 B2 | 1/2020 | Shelton, IV et al. |
| 10,543,008 B2 | 1/2020 | Vakharia et al. |
| 10,548,655 B2 | 2/2020 | Scheib et al. |
| 10,555,769 B2 | 2/2020 | Worrell et al. |
| 10,561,560 B2 | 2/2020 | Boutoussov et al. |
| 10,575,892 B2 | 3/2020 | Danziger et al. |
| 10,595,929 B2 | 3/2020 | Boudreaux et al. |
| 10,595,930 B2 | 3/2020 | Scheib et al. |
| 10,610,286 B2 | 4/2020 | Wiener et al. |
| 10,617,420 B2 | 4/2020 | Shelton, IV et al. |
| 10,617,464 B2 | 4/2020 | Duppuis |
| 10,624,691 B2 | 4/2020 | Wiener et al. |
| RE47,996 E | 5/2020 | Turner et al. |
| 10,639,092 B2 | 5/2020 | Corbett et al. |
| 10,639,098 B2 | 5/2020 | Cosman et al. |
| 10,646,269 B2 | 5/2020 | Worrell et al. |
| 10,677,764 B2 | 6/2020 | Ross et al. |
| 10,687,884 B2 | 6/2020 | Wiener et al. |
| 10,688,321 B2 | 6/2020 | Wiener et al. |
| 10,695,119 B2 | 6/2020 | Smith |
| 10,702,329 B2 | 7/2020 | Strobl et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,729,458 B2 | 8/2020 | Stoddard et al. |
| 10,729,494 B2 | 8/2020 | Parihar et al. |
| 10,736,685 B2 | 8/2020 | Wiener et al. |
| 10,751,108 B2 | 8/2020 | Yates et al. |
| 10,758,294 B2 | 9/2020 | Jones |
| 10,765,470 B2 | 9/2020 | Yates et al. |
| 10,779,845 B2 | 9/2020 | Timm et al. |
| 10,779,849 B2 | 9/2020 | Shelton, IV et al. |
| 10,779,879 B2 | 9/2020 | Yates et al. |
| 10,820,938 B2 | 11/2020 | Fischer et al. |
| 10,828,058 B2 | 11/2020 | Shelton, IV et al. |
| 10,835,307 B2 | 11/2020 | Shelton, IV et al. |
| 10,842,523 B2 | 11/2020 | Shelton, IV et al. |
| 10,842,563 B2 | 11/2020 | Gilbert et al. |
| 10,856,896 B2 | 12/2020 | Eichmann et al. |
| 10,856,929 B2 | 12/2020 | Yates et al. |
| 10,856,934 B2 | 12/2020 | Trees et al. |
| 10,874,465 B2 | 12/2020 | Weir et al. |
| 10,881,449 B2 | 1/2021 | Boudreaux et al. |
| 10,888,347 B2 | 1/2021 | Witt et al. |
| 10,898,256 B2 | 1/2021 | Yates et al. |
| 10,912,580 B2 | 2/2021 | Green et al. |
| 10,912,603 B2 | 2/2021 | Boudreaux et al. |
| 10,925,659 B2 | 2/2021 | Shelton, IV et al. |
| 10,932,847 B2 | 3/2021 | Yates et al. |
| 10,952,788 B2 | 3/2021 | Asher et al. |
| 10,966,741 B2 | 4/2021 | Illizaliturri-Sanchez et al. |
| 10,966,747 B2 | 4/2021 | Worrell et al. |
| 10,987,123 B2 | 4/2021 | Weir et al. |
| 10,987,156 B2 | 4/2021 | Trees et al. |
| 10,993,763 B2 | 5/2021 | Batross et al. |
| 11,020,140 B2 | 6/2021 | Gee et al. |
| 11,033,322 B2 | 6/2021 | Wiener et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177862 A1 | 11/2002 | Aranyi et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0208186 A1 | 11/2003 | Moreyra |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0193153 A1 | 9/2004 | Sartor et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |

(56) References Cited

U.S. PATENT DOCUMENTS

| | | |
|---|---|---|
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iijima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0200123 A1* | 9/2006 | Ryan .................... A61B 18/148 606/48 |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Vole et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |

(56) References Cited

U.S. PATENT DOCUMENTS

| | | |
|---|---|---|
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0015650 A1 | 1/2011 | Choi et al. |
| 2011/0028964 A1 | 2/2011 | Edwards |
| 2011/0071523 A1 | 3/2011 | Dickhans |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136386 A1 | 5/2012 | Kishida et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0211542 A1 | 8/2012 | Racenet |
| 2012/0253328 A1 | 10/2012 | Cunningham et al. |
| 2012/0265241 A1 | 10/2012 | Hart et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0085510 A1 | 4/2013 | Stefanchik et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0277410 A1 | 10/2013 | Fernandez et al. |
| 2013/0296843 A1 | 11/2013 | Boudreaux et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0121569 A1 | 5/2014 | Schafer et al. |
| 2014/0135804 A1 | 5/2014 | Weisenburgh, II et al. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0246475 A1 | 9/2014 | Hall et al. |
| 2014/0263541 A1 | 9/2014 | Leimbach et al. |
| 2014/0263552 A1 | 9/2014 | Hall et al. |
| 2014/0276797 A1 | 9/2014 | Batchelor et al. |
| 2015/0032150 A1 | 1/2015 | Ishida et al. |
| 2015/0080876 A1 | 3/2015 | Worrell et al. |
| 2015/0080887 A1 | 3/2015 | Sobajima et al. |

(56) References Cited

U.S. PATENT DOCUMENTS

| | | |
|---|---|---|
| 2015/0088122 A1 | 3/2015 | Jensen |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0238260 A1 | 8/2015 | Nau, Jr. |
| 2015/0257780 A1 | 9/2015 | Houser |
| 2015/0272581 A1 | 10/2015 | Leimbach et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2016/0045248 A1 | 2/2016 | Unger et al. |
| 2016/0051316 A1 | 2/2016 | Boudreaux |
| 2016/0066909 A1 | 3/2016 | Swayze et al. |
| 2016/0175029 A1 | 6/2016 | Witt et al. |
| 2016/0206342 A1 | 7/2016 | Robertson et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0358849 A1 | 12/2016 | Jur et al. |
| 2017/0000516 A1 | 1/2017 | Stulen et al. |
| 2017/0000541 A1 | 1/2017 | Yates et al. |
| 2017/0000553 A1 | 1/2017 | Wiener et al. |
| 2017/0086876 A1 | 3/2017 | Wiener et al. |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164997 A1 | 6/2017 | Johnson et al. |
| 2017/0189095 A1 | 7/2017 | Danziger et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202595 A1 | 7/2017 | Shelton, IV |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202607 A1 | 7/2017 | Shelton, IV et al. |
| 2017/0296177 A1 | 10/2017 | Harris et al. |
| 2017/0312018 A1 | 11/2017 | Trees et al. |
| 2017/0325874 A1 | 11/2017 | Noack et al. |
| 2018/0014872 A1 | 1/2018 | Dickerson |
| 2018/0098785 A1 | 4/2018 | Price et al. |
| 2018/0146976 A1 | 5/2018 | Clauda et al. |
| 2018/0235691 A1 | 8/2018 | Voegele et al. |
| 2018/0325517 A1 | 11/2018 | Wingardner et al. |
| 2019/0105067 A1 | 4/2019 | Boudreaux et al. |
| 2019/0201048 A1 | 7/2019 | Stulen et al. |
| 2019/0209201 A1 | 7/2019 | Boudreaux et al. |
| 2019/0262030 A1 | 8/2019 | Faller et al. |
| 2019/0282288 A1 | 9/2019 | Boudreaux |
| 2019/0282292 A1 | 9/2019 | Wiener et al. |
| 2019/0388091 A1 | 12/2019 | Eschbach et al. |
| 2020/0030021 A1 | 1/2020 | Yates et al. |
| 2020/0054382 A1 | 2/2020 | Yates et al. |
| 2020/0078085 A1 | 3/2020 | Yates et al. |
| 2020/0078609 A1 | 3/2020 | Messerly et al. |
| 2020/0085465 A1 | 3/2020 | Timm et al. |
| 2020/0113624 A1 | 4/2020 | Worrell et al. |
| 2020/0129261 A1 | 4/2020 | Eschbach |
| 2020/0138473 A1 | 5/2020 | Shelton, IV et al. |
| 2020/0222135 A1 | 7/2020 | Stulen et al. |
| 2020/0229833 A1 | 7/2020 | Vakharia et al. |
| 2020/0229834 A1 | 7/2020 | Olson et al. |
| 2020/0237434 A1 | 7/2020 | Scheib et al. |
| 2020/0261141 A1 | 8/2020 | Wiener et al. |
| 2020/0268433 A1 | 8/2020 | Wiener et al. |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0177481 A1 | 6/2021 | Shelton, IV et al. |
| 2021/0177496 A1 | 6/2021 | Shelton, IV et al. |
| 2021/0186553 A1 | 6/2021 | Green et al. |
| 2021/0186554 A1 | 6/2021 | Green et al. |
| 2021/0196263 A1 | 7/2021 | Shelton, IV et al. |
| 2021/0196265 A1 | 7/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196301 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196350 A1 | 7/2021 | Fiebig et al. |
| 2021/0196351 A1 | 7/2021 | Sarley et al. |
| 2021/0196352 A1 | 7/2021 | Messerly et al. |
| 2021/0196353 A1 | 7/2021 | Gee et al. |
| 2021/0196354 A1 | 7/2021 | Shelton, IV et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196360 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |
| 2021/0393314 A1 | 12/2021 | Wiener et al. |
| 2021/0393319 A1 | 12/2021 | Shelton, IV et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 101474081 A | 7/2009 |
| CN | 101516285 A | 8/2009 |
| CN | 101522112 A | 9/2009 |
| CN | 102100582 A | 6/2011 |
| CN | 102149312 A | 8/2011 |
| CN | 202027624 U | 11/2011 |
| CN | 102792181 A | 11/2012 |
| CN | 103281982 A | 9/2013 |
| CN | 103379853 A | 10/2013 |
| CN | 203468630 U | 3/2014 |
| CN | 104001276 A | 8/2014 |
| CN | 104013444 A | 9/2014 |
| CN | 104434298 A | 3/2015 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |

(56) References Cited

FOREIGN PATENT DOCUMENTS

| | | |
|---|---|---|
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 2510891 B1 | 6/2016 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | 2000210299 A | 8/2000 |
| JP | 2000271142 A | 10/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9840015 A2 | 9/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-201 1052939 A2 | 5/2011 |
| WO | WO-2011060031 A1 | 5/2011 |
| WO | WO-2012044606 A2 | 4/2012 |
| WO | WO-2012088535 A1 | 6/2012 |
| WO | WO-2012150567 A1 | 11/2012 |

OTHER PUBLICATIONS

Hörmann et al., "Reversible and irreversible denaturation of collagen fibers." Biochemistry, 10, pp. 932-937 (1971).

Technology Overview, printed from www.harmonicscalpel.com, Internet site, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008], Retrieved from the internet: URL: http//wonder.cdc.gov/wonder/prevguid/p0000191/p0000191.asp (15 pages).

Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

(56) References Cited

OTHER PUBLICATIONS

Covidien Brochure, The LigaSure Precise™ Instrument, dated Mar. 2011 (2 pages).
AST Products, Inc., "Principles of Video Contact Angle Analysis," 20 pages, (2006).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Heat-induced changes in the mechanics of a collagenous tissue: pseudoelastic behavior at 37° C.," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Moraleda et al., A Temperature Sensor Based on a Polymer Optical Fiber Macro-Bend, Sensors 2013, 13, 13076-13089, doi: 10.3390/s131013076, ISSN 1424-8220.
Leonard I. Malis, M.D., "The Value of Irrigation During Bipolar Coagulation," 1989.
http://www.ethicon.com/GB-en/healthcare-professionals/products/energy-devices/capital//ge . . . .
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
Campbell et al., "Thermal Imaging in Surgery," p. 19-3, in Medical Infrared Imaging, N. A. Diakides and J. D. Bronzino, Eds. (2008).
http://www.dotmed.com/listing/electrosurical-unit/ethicon/ultracision-g110-/1466724.
http://www.4-traders.com/JOHNSON-JOHNSON-4832/news/Johnson-Johnson-Ethicon-E . . . .
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
Sullivan, "Cost-Constrained Selection of Strand Diameter and No. in a Litz-Wire Transformer Winding," IEEE Transactions on Power Electronics, vol. 16, No. 2, Mar. 2001, pp. 281-288.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
Covidien Brochure, [Value Analysis Brief], LigaSure Advance™ Pistol Grip, dated Rev. Apr. 2010 (7 pages).
Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Erbe Electrosurgery VIO® 200 S, (2012), p. 7, 12 pages, accessed Mar. 31, 2014 at http://www.erbe-med.com/erbe/media/Marketing materialien/85140170 ERBE EN VIO 200 S D027541.
Jang, J. et al. "Neuro-fuzzy and Soft Computing." Prentice Hall, 1997, pp. 13-89, 199-293, 335-393, 453-496, 535-549.
Sullivan, "Optimal Choice for No. of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Wall et al., "Thermal modification of collagen," J Shoulder Elbow Surg, No. 8, pp. 339-344 (Jul./Aug. 1999).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Douglas, S.C. "Introduction to Adaptive Filter". Digital Signal Processing Handbook. Ed. Vijay K. Madisetti and Douglas B. Williams. Boca Raton: CRC Press LLC, 1999.
Kurt Gieck & Reiner Gieck, *Engineering Formulas* § Z.7 (7th ed. 1997).
Glaser and Subak-Sharpe,Integrated Circuit Engineering, Addison-Wesley Publishing, Reading, MA (1979). (book—not attached).
Covidien 501 (k) Summary Sonicision, dated Feb. 24, 2011 (7 pages).
http://www.megadyne.com/es_generator.php.
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
http://www.apicalinstr.com/generators.htm.

(56) References Cited

OTHER PUBLICATIONS http://www.medicalexpo.com/medical-manufacturer/electrosurgical-generator-6951.html.
http://www.valleylab.com/product/es/generators/index.html.

* cited by examiner

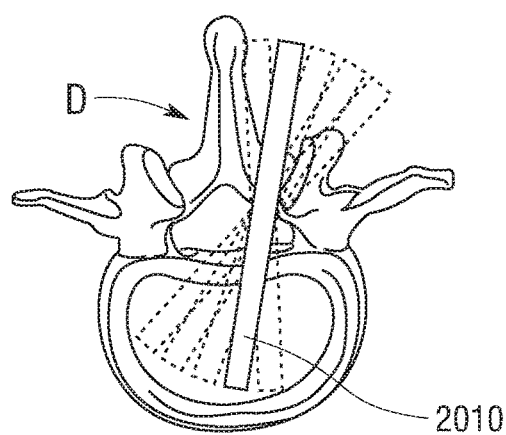
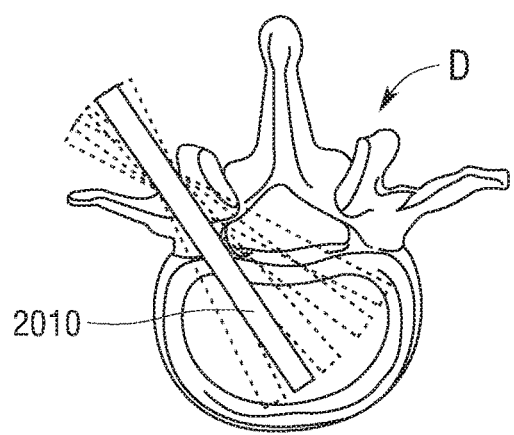
Fig.39  Fig.40
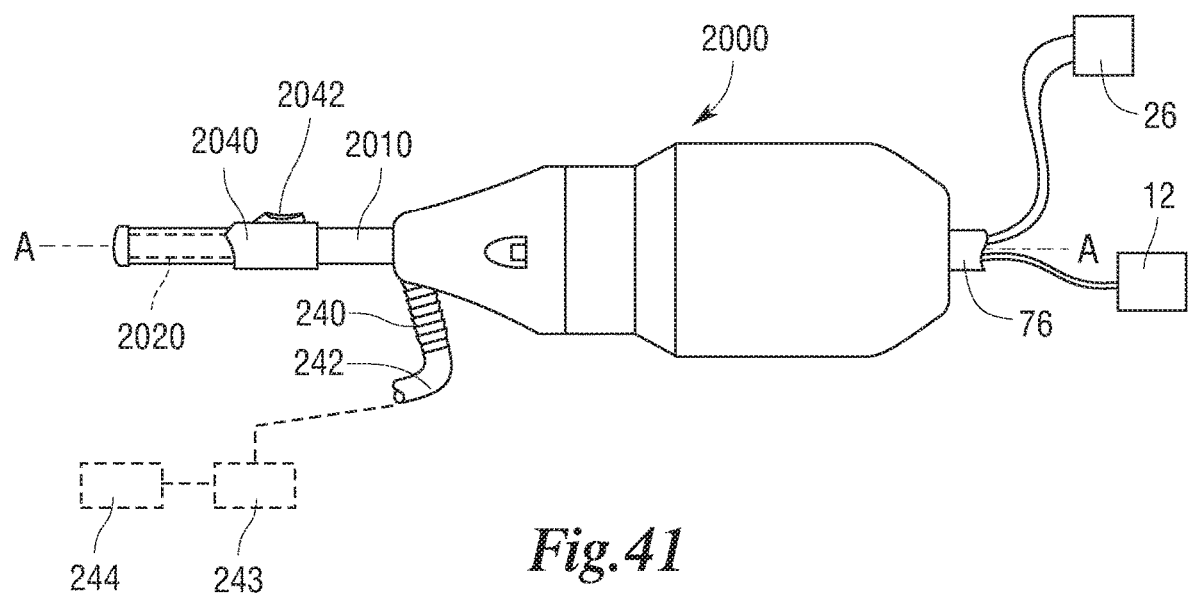
Fig.41

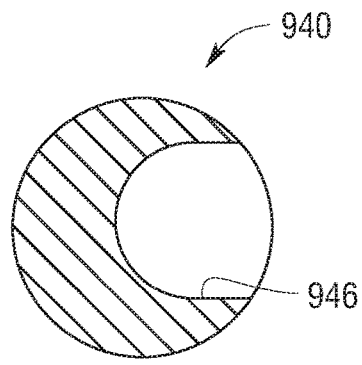 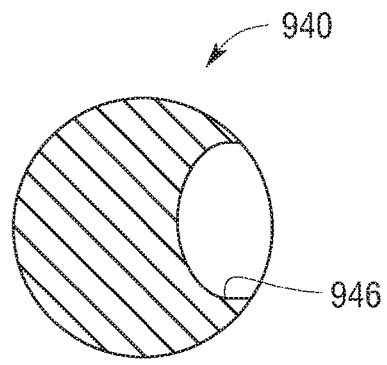 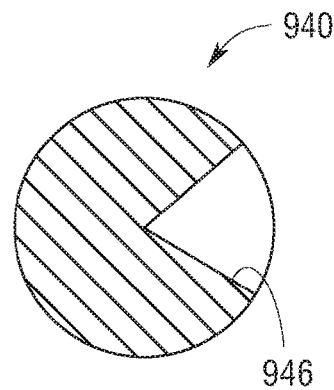
*Fig.48*  *Fig.49*  *Fig.50*
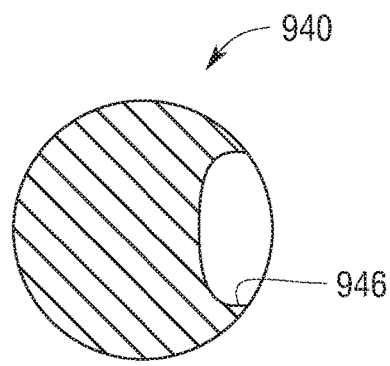
*Fig.51*

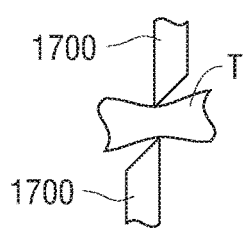
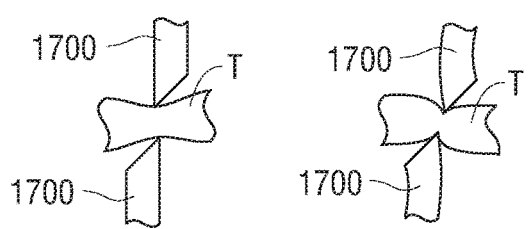
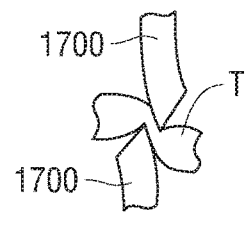
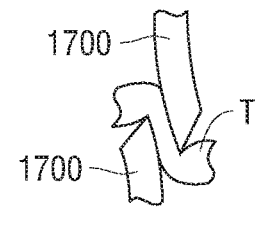
*Fig.91A*   *Fig.91B*   *Fig.91C*   *Fig.91D*
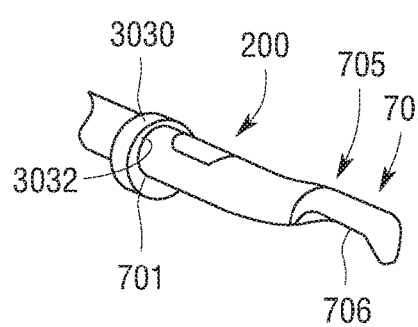
*Fig.92*
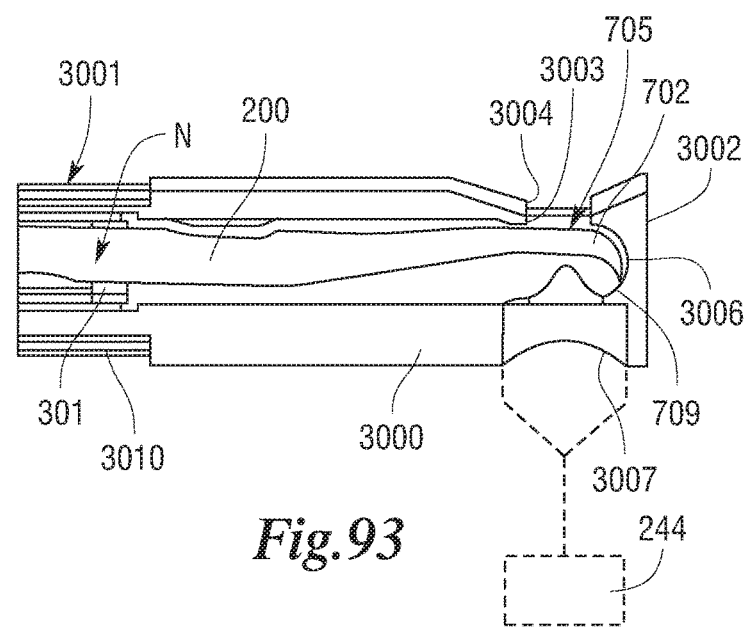
*Fig.93*
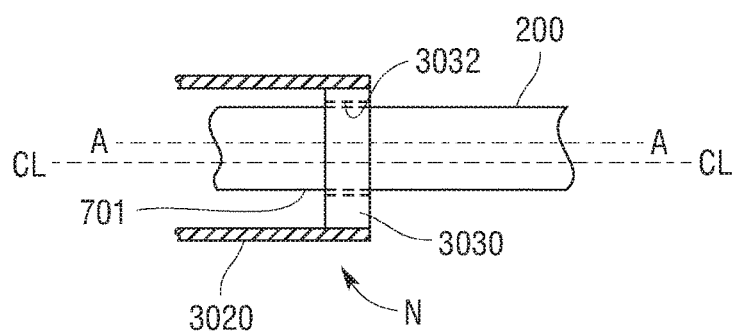
*Fig.92A*

ROTATABLE CUTTING IMPLEMENTS WITH FRICTION REDUCING MATERIAL FOR ULTRASONIC SURGICAL INSTRUMENTS

CROSS-REFERENCE TO RELATED APPLICATIONS

This non-provisional patent application is a divisional application claiming priority under 35 U.S.C. § 121 to U.S. patent application Ser. No. 15/249,860, filed Aug. 29, 2016, entitled ROTATABLE CUTTING IMPLEMENTS WITH FRICTION REDUCING MATERIAL FOR ULTRASONIC SURGICAL INSTRUMENTS, which issued on May 28, 2019 as U.S. Pat. No. 10,299,810, which is a divisional application claiming priority under 35 U.S.C. § 121 to U.S. patent application Ser. No. 13/891,269, filed May 10, 2013, entitled ROTATABLE CUTTING IMPLEMENTS WITH FRICTION REDUCING MATERIAL FOR ULTRASONIC SURGICAL INSTRUMENTS, which issued on Aug. 30, 2016 as U.S. Pat. No. 9,427,249, which is a divisional application claiming priority under 35 U.S.C. § 121 to U.S. patent application Ser. No. 12/703,875, filed Feb. 11, 2010, entitled ROTATABLE CUTTING IMPLEMENT ARRANGEMENTS FOR ULTRASONIC SURGICAL INSTRUMENTS, which issued on Jun. 25, 2013 as U.S. Pat. No. 8,469,981, the entire disclosures of which are hereby incorporated by reference herein.

BACKGROUND

The present disclosure generally relates to ultrasonic surgical systems and, more particularly, to ultrasonic systems that allow surgeons to perform cutting and coagulation of tissue.

Over the years, a variety of different types of non-ultrasonically powered cutters and shaving devices for performing surgical procedures have been developed. Some of these devices employ a rotary cutting instrument and other devices employ a reciprocating cutting member. For example, shavers are widely used in arthroscopic surgery. These devices generally consist of a power supply, a handpiece, and a single-use end effector. The end effector commonly has an inner and outer tube. The inner tube rotates relative to the outer tube and will cut tissue with its sharpened edges. The inner tube can rotate continuously or oscillate. In addition, such device may employ a suction channel that travels through the interior of the inner tube. For example, U.S. Pat. No. 4,850,354 to McGurk-Burleson, et al., discloses a non-ultrasonically powered surgical cutting instrument that comprises a rotary cutter for cutting material with a shearing action. It employs an inner cutting member which is rotatable within an outer tube.

U.S. Pat. No. 3,776,238 to Peyman et al. discloses an ophthalmic instrument in which tissue is cut by a chopping action set-up by the sharp end of an inner tube moving against the inner surface of the end of an outer tube. U.S. Pat. No. 5,226,910 to Kajiyama et al. discloses another surgical cutting instrument that has an inner member which moves relative to an outer member to cut tissue entering through an aperture in the outer member.

U.S. Pat. No. 4,922,902 to Wuchinich et al. discloses a method and apparatus for endoscopic removal of tissue utilizing an ultrasonic aspirator. The device uses an ultrasonic probe which disintegrates compliant tissue and aspirates it through a narrow orifice. U.S. Pat. No. 4,634,420 to Spinosa et al. discloses an apparatus and method for removing tissue from an animal and includes an elongated instrument having a needle or probe, which is vibrated at an ultrasonic frequency in the lateral direction. The ultrasonic movement of the needle breaks-up the tissue into fragments. Pieces of tissue can be removed from the area of treatment by aspiration through a conduit in the needle. U.S. Pat. No. 3,805,787 to Banko discloses yet another ultrasonic instrument that has a probe that is shielded to narrow the beam of ultrasonic energy radiated from the tip of the probe. In one embodiment the shield extends past the free-end of the probe to prevent the probe from coming into contact with the tissue. U.S. Pat. No. 5,213,569 to Davis discloses a phaco-emulsification needle which focuses the ultrasonic energy. The focusing surfaces can be beveled, curved or faceted. U.S. Pat. No. 6,984,220 to Wuchinich and U.S. Patent Publication No. US 2005/0177184 to Easley disclose ultrasonic tissue dissection systems that provide combined longitudinal and torsional motion through the use of longitudinal-torsional resonators. U. S Patent Publication no. US 2006/0030797 A1 to Zhou et al. discloses an orthopedic surgical device that has a driving motor for driving an ultrasound transducer and horn. An adapter is provided between the driving motor and transducer for supplying ultrasonic energy signals to the transducer.

While the use of ultrasonically powered surgical instruments provide several advantages over traditional mechanically powered saws, drills, and other instruments, temperature rise in bone and adjacent tissue due to frictional heating at the bone/tissue interface can still be a significant problem. Current arthroscopic surgical tools include punches, reciprocating shavers and radio frequency (RF) devices. Mechanical devices such as punches and shavers create minimal tissue damage, but can sometimes leave behind ragged cut lines, which are undesirable. RF devices can create smoother cut lines and also ablate large volumes of soft tissue; however, they tend to create more tissue damage than mechanical means. Thus, device which could provide increased cutting precision while forming smooth cutting surfaces without creating excessive tissue damage would be desirable.

Arthroscopic surgery involves performing surgery in the joint space. To perform the surgery, the joints are commonly filled with pressurized saline for distention and visualization. Ultrasonic instruments which may be used in such surgeries must withstand the fluid pressure without leaking. However, conventional ultrasonic instruments generally experience significant forces during use. Current seals on ultrasonic devices are generally not robust enough to withstand this environment without leaking.

It would be desirable to provide an ultrasonic surgical instrument that overcomes some of the deficiencies of current instruments. The ultrasonic surgical instruments described herein overcome many of those deficiencies.

It would also be desirable to provide more robust sealing arrangements for ultrasonic surgical instruments used to cut and coagulate in the aqueous environment of arthroscopic surgery.

The foregoing discussion is intended only to illustrate some of the shortcomings present in the field of various embodiments of the invention at the time, and should not be taken as a disavowal of claim scope.

SUMMARY

In one exemplary embodiment, a surgical instrument may comprise a housing, a transducer assembly, a motor, a hollow sheath, and a blade. The transducer assembly may be rotatably supported within the housing and may be configured to selectively generate an ultrasonic motion. The motor may be coupled to the transducer assembly and may be configured to selectively apply rotational motion to the transducer assembly. The hollow sheath may be coupled to the housing and may define a distal cavity. The blade may be coupled to the transducer assembly and may be rotatably supported within the hollow sheath. A distal end of the blade may include a tissue-cutter that may be rotatably supported in the distal cavity. The distal cavity may comprise a friction reducing material. A portion of the tissue-cutter may be arranged to apply the ultrasonic motion to tissue.

In another exemplary embodiment, an ultrasonic surgical instrument may comprise a housing, an ultrasonic transducer assembly, a motor, an outer sheath, and a blade. The ultrasonic transducer assembly may selectively generate ultrasonic motion and may be rotatably supported within the housing. The motor may be within the housing may be configured to selectively apply a rotary motion to the ultrasonic transducer assembly. The outer sheath may be coupled to the housing. The outer sheath may comprise a distal tip portion that may define a tip cavity. The blade may be operably coupled to the ultrasonic transducer assembly and may be rotatably supported within the outer sheath for rotation with the ultrasonic transducer assembly. The blade may include a tissue-cutting distal end that may be rotatably supported within the tip cavity. The tip cavity may comprise a friction reducing material. A portion of the tissue-cutting distal end may be configured to apply the ultrasonic motion to tissue.

In yet another exemplary embodiment, a surgical instrument may comprise a housing, a rotatable transducer assembly, a motor, a cylindrical shaft, and a blade. The rotatable transducer assembly may be operable to selectively generate an ultrasonic motion. The motor may be operable to selectively rotate the rotatable transducer assembly within the housing. The cylindrical shaft may be coupled to the housing and may define a distal tip cavity. The blade may be operably coupled to the rotatable transducer assembly and may be rotatably supported within the cylindrical shaft. The blade may include a tissue-cutting distal end that may be rotatably supported within the distal tip cavity. The distal tip cavity may comprise a low friction material. The tissue-cutting distal end may be arranged to apply the ultrasonic motion to tissue.

FIGURES

The features of various non-limiting embodiments are set forth with particularity in the appended claims. The various non-limiting embodiments, however, both as to organization and methods of operation, together with further objects and advantages thereof, may best be understood by reference to the following description, taken in conjunction with the accompanying drawings as follows.

FIG. 39 illustrates use of the surgical instrument embodiment of FIG. 36 in connection with performing a discectomy;

FIG. 40 depicts further use of the surgical instrument embodiment of FIG. 36 in connection with performing a discectomy;

FIG. 41 is a side elevational view of the surgical instrument embodiment of FIG. 36 with a selectively retractable safety sheath mounted thereon;

FIG. 48 is a cross-sectional view of another non-limiting blade embodiment;

FIG. 49 is a cross-sectional view of another non-limiting blade embodiment;

FIG. 50 is a cross-sectional view of another non-limiting blade embodiment;

FIG. 51 is a cross-sectional view of another non-limiting blade embodiment;

FIG. 91A is an illustration depicting an initial position of two cutting edge embodiments preparing to cut tough tissue;

FIG. 91B is a second position of the cutting edges and tissue of FIG. 91A;

FIG. 91C is a third position of the cutting edges and tissue of FIGS. 91A-B;

FIG. 91D is a fourth position of the cutting edges and tissue of FIGS. 91A-C;

FIG. 92 is a perspective view of a portion of a non-limiting cutting blade and bushing embodiment;

FIG. 92A is a partial cross-sectional view of a portion of the blade and bushing embodiment of FIG. 92 installed within an inner sheath of a non-limiting surgical instrument embodiment;

FIG. 93 is a cross-sectional view of a portion of the blade and bushing embodiment of FIG. 92 in a non-limiting surgical instrument embodiment;

DESCRIPTION

Figure 1:
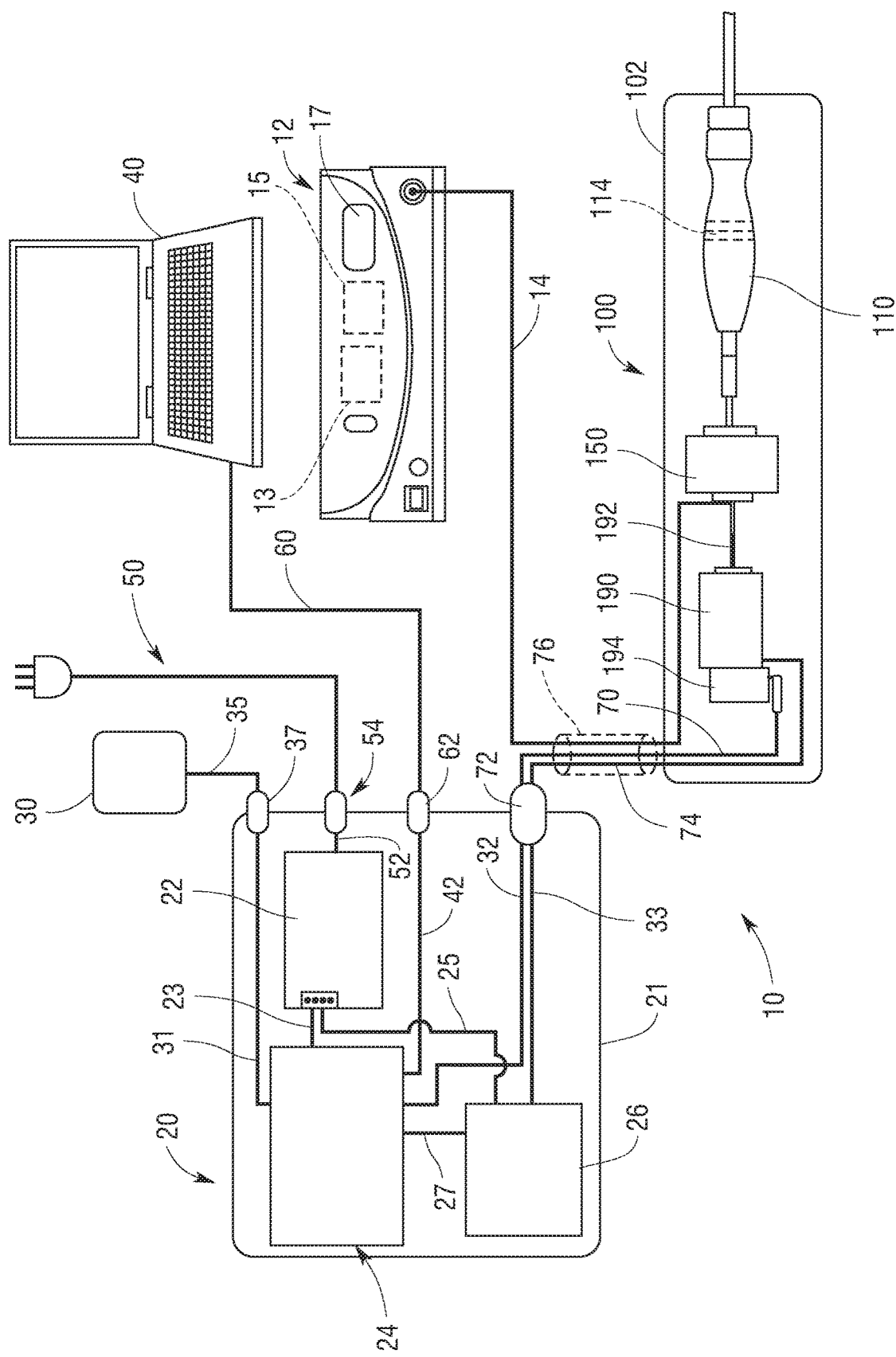
FIG. 1 is a schematic view of a non-limiting embodiment of a surgical control system.

The owner of the present application also owns the following U.S. Patent Applications, filed Feb. 11, 2010, which are herein incorporated by reference in their respective entireties:

U.S. patent application Ser. No. 12/703,860, now U.S. Pat. No. 8,531,064, entitled ULTRASONICALLY POWERED SURGICAL INSTRUMENTS WITH ROTATING CUTTING IMPLEMENT;

U.S. patent application Ser. No. 12/703,864, now U.S. Pat. No. 8,323,302, entitled METHODS OF USING ULTRASONICALLY POWERED SURGICAL INSTRUMENTS WITH ROTATABLE CUTTING IMPLEMENTS;

U.S. patent application Ser. No. 12/703,866, now U.S. Pat. No. 8,951,272, entitled SEAL ARRANGEMENTS FOR ULTRASONICALLY POWERED SURGICAL INSTRUMENTS;

U.S. patent application Ser. No. 12/703,870, now U.S. Pat. No. 9,259,234, entitled ULTRASONIC SURGICAL INSTRUMENTS WITH ROTATABLE BLADE AND HOLLOW SHEATH ARRANGEMENTS;

U.S. patent application Ser. No. 12/703,877, now U.S. Pat. No. 8,382,782, entitled ULTRASONIC SURGICAL INSTRUMENTS WITH PARTIALLY ROTATING BLADE AND FIXED PAD ARRANGEMENT;

U.S. patent application Ser. No. 12/703,879, now U.S. Pat. No. 8,486,096, entitled DUAL PURPOSE SURGICAL INSTRUMENT FOR CUTTING AND COAGULATING TIS SUE;

U.S. patent application Ser. No. 12/703,885, now U.S. Pat. No. 8,579,928, entitled OUTER SHEATH AND BLADE ARRANGEMENTS FOR ULTRASONIC SURGICAL INSTRUMENTS;

U.S. patent application Ser. No. 12/703,893, now U.S. Pat. No. 8,961,547, entitled ULTRASONIC SURGICAL INSTRUMENTS WITH MOVING CUTTING IMPLEMENT; and U.S. patent application Ser. No. 12/703,899, now U.S. Pat. No. 8,419,759, entitled ULTRASONIC SURGICAL INSTRUMENT WITH COMB-LIKE TISSUE TRIMMING DEVICE.

Various embodiments are directed to apparatuses, systems, and methods for the treatment of tissue Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

Various embodiments are directed to improved ultrasonic surgical systems and instruments configured for effecting tissue dissecting, cutting, and/or coagulation during surgical procedures as well as the cutting implements and sealing features employed thereby. In one embodiment, an ultrasonic surgical instrument apparatus is configured for use in open surgical procedures, but has applications in other types of surgery, such as laparoscopic, endoscopic, and robotic-assisted procedures. Versatile use is facilitated by selective use of ultrasonic energy and the selective rotation of the cutting/coagulation implement.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

Surgical Systems

FIG. 1 illustrates in schematic form one non-limiting embodiment of a surgical system 10. The surgical system 10 may include a ultrasonic generator 12 and an ultrasonic surgical instrument assembly 100 that may include a "self-contained" ultrasonic instrument 110. As will be discussed in further detail below, the ultrasonic generator 12 may be connected by a cable 14 to an ultrasonic transducer assembly 114 of the self-contained ultrasonic instrument 110 by a slip ring assembly 150 located in a housing portion 102 of the surgical instrument assembly 100. In one embodiment, the system 10 further includes a motor control system 20 that includes a power supply 22 that is coupled to a control module 24 by cable 23 to supply, for example, 24 VDC thereto. The motor control module 24 may comprise a control module manufactured by National Instruments of Austin, Tex. under Model No. NI cRIO-9073. However, other motor control modules may be employed. The power supply 22 may comprise a power supply manufactured by National Instruments. However, other power supplies may be successfully employed. The power supply 22 may be further coupled to a motor drive 26 by cable 25 to also supply 24 VDC thereto. The motor drive 26 may comprise a motor drive manufactured by National Instruments. Control module 24 may also be coupled to the motor drive 26 by cable 27 for supplying power thereto. A conventional foot pedal 30 or other control switch arrangement may be attached to the control module 24 by a cable 31. As will be discussed in further detail below, the ultrasonic surgical instrument 100 may include a motor 190 that has an encoder 194 associated therewith. The motor 190 may comprise a motor manufactured by National Instruments under Model No. CTP12ELF10MAA00. The encoder 194 may comprise an encoder manufactured by U.S. Digital of Vancouver, Wash. under Model No. E2-500-197-I-D-D-B. However, other motors and encoders may be used. The encoder 194 may be coupled to the motor control module 24 by an encoder cable 32 and the motor 190 may be coupled to the motor drive 26 by cable 33. The surgical system 10 may also include a computer 40 that may communicate by Ethernet cable 42 with the motor control module 24.

As can also be seen in FIG. 1, in various embodiments, the motor control system 20 is housed in an enclosure 21. To facilitate easy portability of the system, various components may be attached to the motor control system 20 by removable cable connectors. For example, foot pedal switch 30 may be attached to a detachable cable connector 37 by cable 35 to facilitate quick attachment of the foot pedal to the control system 20. A/C power may be supplied to the power supply 22 by a conventional plug/cable 50 that is attached to a detachable cable connector 54 that is attached to cable 52. The computer 40 may have a cable 60 that is attached to detachable cable connector 62 that is coupled to cable 42. The encoder 194 may have an encoder cable 70 that is attached to a detachable connector 72. Likewise, the motor 190 may have a cable 74 that is attached to the detachable connector 72. The detachable connector 72 may be attached to the control module 24 by cable 32 and the connector 72 may be attached to the motor drive 26 by cable 33. Thus, cable connector 72 serves to couple the encoder 194 to the control module 24 and the motor 190 to the motor drive 26. The cables 70 and 74 may be housed in a common sheath 76.

Figure 1A:
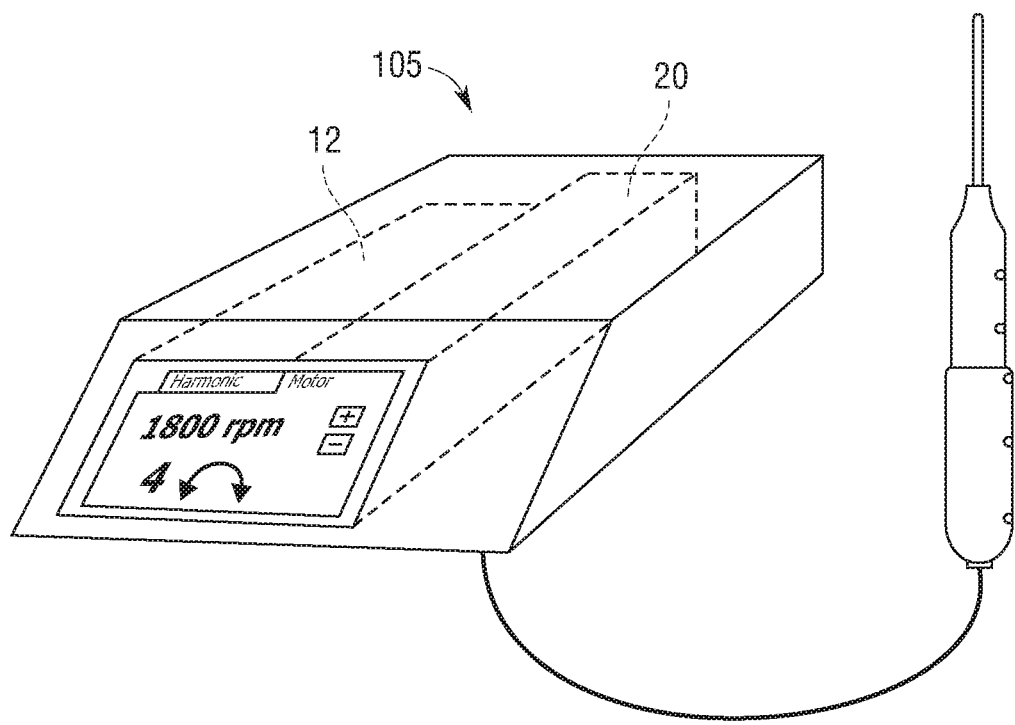
FIG. 1A is a perspective view of a non-limiting embodiment of control system enclosure.
Figure 1B:
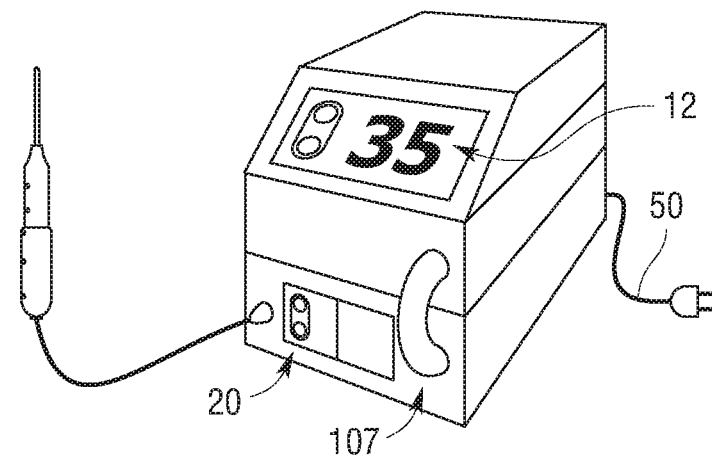
FIG. 1B is a perspective view of another non-limiting embodiment of a control system enclosure arrangement.

In an alternative embodiment, the ultrasonic generator 12 and the control system 20 may be housed in the same enclosure 105. See FIG. 1A. In yet another embodiment, the ultrasonic generator 12 may electrically communicate with the motor control system 20 by a jumper cable 107. Such arrangement may share a data link as well as a common means for supplying power (cord 50). See FIG. 1B.

In various embodiments, the ultrasonic generator 12 may include an ultrasonic generator module 13 and a signal generator module 15. See FIG. 1. The ultrasonic generator module 13 and/or the signal generator module 15 each may be integrated with the ultrasonic generator 12 or may be provided as a separate circuit module electrically coupled to the ultrasonic generator 12 (shown in phantom to illustrate this option). In one embodiment, the signal generator module 15 may be formed integrally with the ultrasonic generator module 13. The ultrasonic generator 12 may comprise an input device 17 located on a front panel of the generator 12 console. The input device 17 may comprise any suitable device that generates signals suitable for programming the operation of the generator 12 in a known manner. Still with reference to FIG. 1, the cable 14 may comprise multiple electrical conductors for the application of electrical energy to positive (+) and negative (−) electrodes of an ultrasonic transducer assembly 114 as will be discussed in further detail below.

Various forms of ultrasonic generators, ultrasonic generator modules and signal generator modules are known. For example, such devices are disclosed in commonly owned U.S. patent application Ser. No. 12/503,770, entitled Rotating Transducer Mount For Ultrasonic Surgical Instruments, filed Jul. 15, 2007, now U.S. Pat. No. 8,461,744, which is herein incorporated by reference in its entirety. Other such devices are disclosed in one or more of the following U.S. Patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

Surgical Instruments

Figure 2:
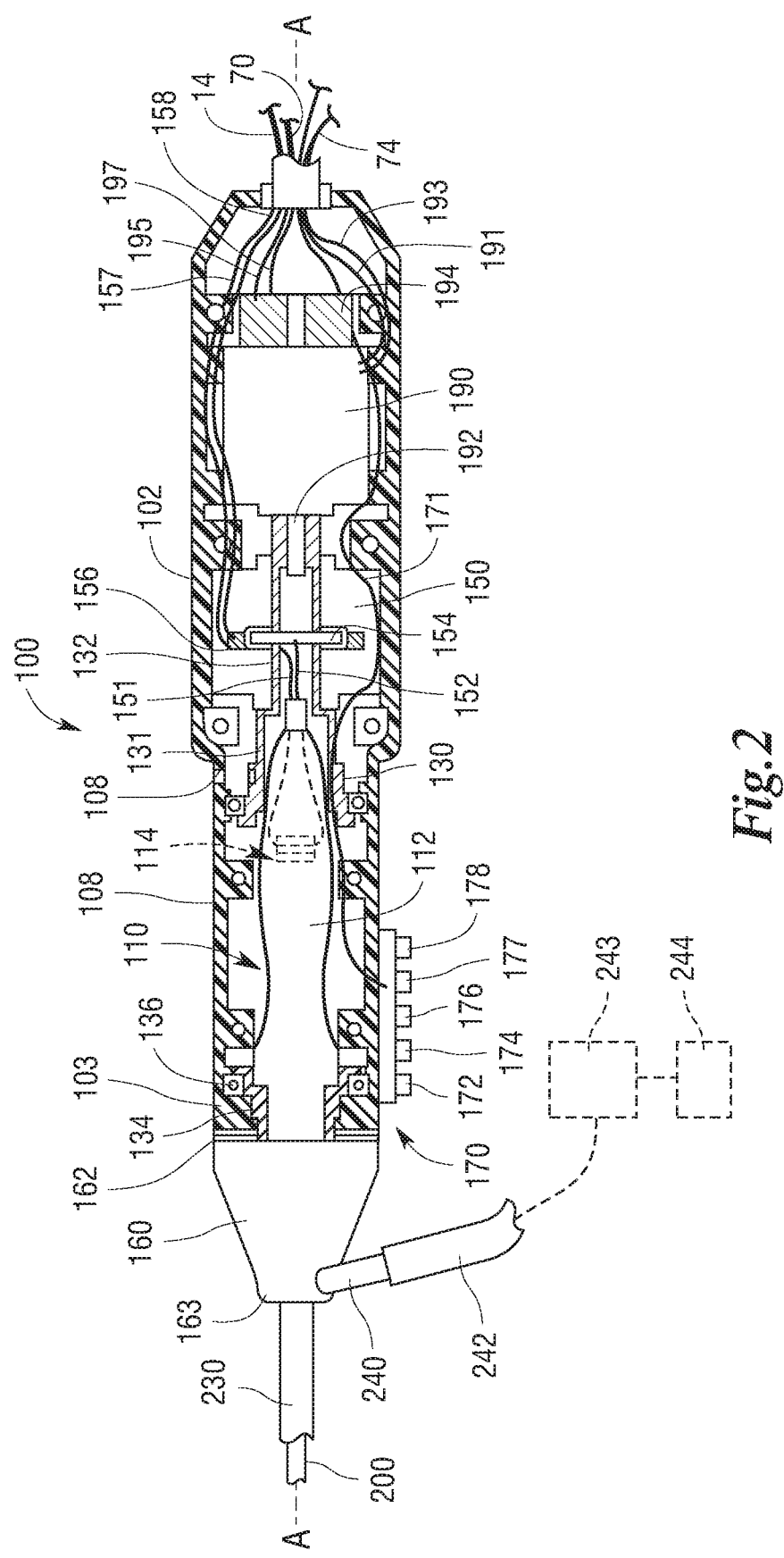
FIG. 2 is a cross-sectional view of a non-limiting embodiment of a handpiece.

As can be seen in FIG. 2, an ultrasonic surgical instrument handpiece 100 may comprise a housing 102 that houses the motor 190, the encoder 194, the slip ring assembly 150 and the self-contained ultrasonic surgical instrument 110. The housing 102 may be provided in two or more parts that are attached together by fasteners such as screws, snap features, etc. and may be fabricated from, for example, polycarbonate material. The motor 190 may comprise, for example, a stepper motor manufactured by National Instruments under Model No. CTP12ELF10MAA00. However other motors may be employed to effectuate, for example, "gross" rotational motion of the self-contained ultrasonic surgical instrument 110 relative to the housing 102 on the order of 1-6000 rpm. The encoder 194 converts the mechanical rotation of the motor shaft 192 into electrical pulses that provide speed and other motor control information to the control module 24.

Figure 3:
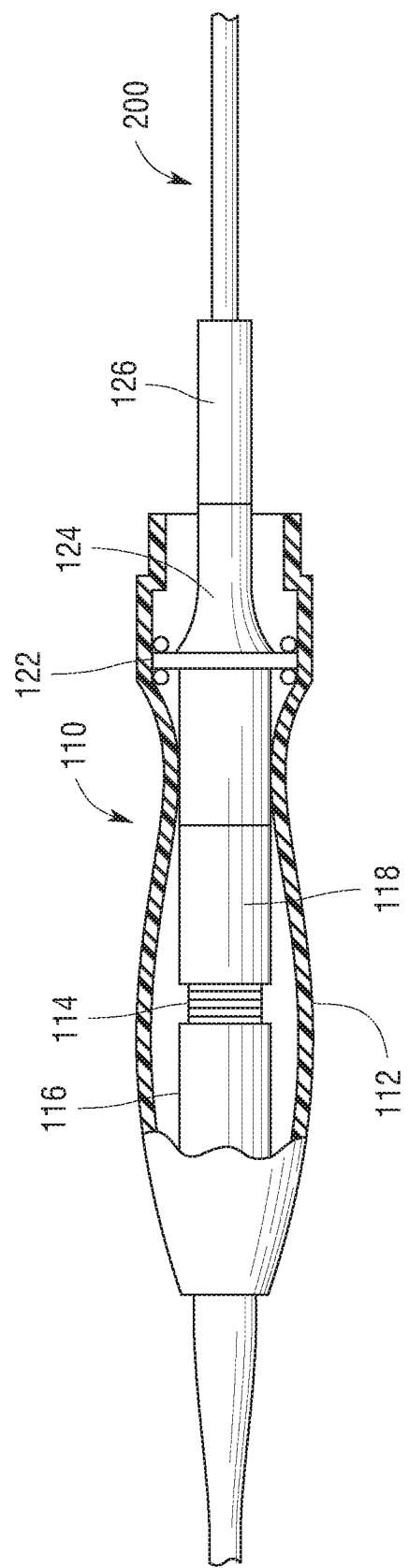
FIG. 3 is a partial cross-sectional view of an ultrasonic surgical handpiece that may be employed with various non-limiting embodiments.

The self-contained ultrasonic surgical instrument 110 may comprise a surgical instrument that is manufactured and sold by Ethicon Endo-Surgery under Model No. HP054. However, other ultrasonic instruments may be successfully employed. It will be understood that the term "self-contained" as used herein means that the ultrasonic surgical instrument may be effectively used as an ultrasonic surgical instrument on its own, apart from use with the surgical instrument 100. As illustrated in more detail in FIG. 3, the ultrasonic surgical instrument 110 includes a housing 112 that supports a piezoelectric ultrasonic transducer assembly 114 for converting electrical energy to mechanical energy that results in longitudinal vibrational motion of the ends of the transducer assembly 114. The ultrasonic transducer assembly 114 may comprise a stack of ceramic piezoelectric elements with a motion null point located at some point along the stack. The ultrasonic transducer assembly 114 may be mounted between two cylinders 116 and 118. In addition, a cylinder 120 may be attached to cylinder 118, which in turn is mounted to the housing at another motion null point 122. A horn 124 may also be attached at the null point on one side and to a coupler 126 on the other side. A blade 200 may be fixed to the coupler 126. As a result, the blade 200 will vibrate in the longitudinal direction at an ultrasonic frequency rate with the ultrasonic transducer assembly 114. The ends of the ultrasonic transducer assembly 114 achieve maximum motion with a portion of the stack constituting a motionless node, when the ultrasonic transducer assembly 114 is driven at maximum current at the transducer's resonant frequency. However, the current providing the maximum motion will vary with each instrument and is a value stored in the non-volatile memory of the instrument so the system can use it.

The parts of the ultrasonic instrument 110 may be designed such that the combination will oscillate at the same resonant frequency. In particular, the elements may be tuned such that the resulting length of each such element is one-half wavelength or a multiple thereof. Longitudinal back and forth motion is amplified as the diameter closer to the blade 200 of the acoustical mounting horn 124 decreases. Thus, the horn 124 as well as the blade/coupler may be shaped and dimensioned so as to amplify blade motion and provide ultrasonic vibration in resonance with the rest of the acoustic system, which produces the maximum back and forth motion of the end of the acoustical mounting horn 124 close to the blade 200. A motion from 20 to 25 microns at the ultrasonic transducer assembly 114 may be amplified by the horn 124 into blade movement of about 40 to 100 microns.

When power is applied to the ultrasonic instrument 110 by operation of the foot pedal 30 or other switch arrangement, the control system 20 may, for example, cause the blade 200 to vibrate longitudinally at approximately 55.5 kHz, and the amount of longitudinal movement will vary proportionately with the amount of driving power (current) applied, as adjustably selected by the user. When relatively high cutting power is applied, the blade 200 may be designed to move longitudinally in the range of about 40 to 100 microns at the ultrasonic vibrational rate. Such ultrasonic vibration of the blade 200 will generate heat as the blade contacts tissue, i.e., the acceleration of the blade 200 through the tissue converts the mechanical energy of the moving blade 200 to thermal energy in a very narrow and localized area. This localized heat creates a narrow zone of coagulation, which will reduce or eliminate bleeding in small vessels, such as those less than one millimeter in diameter. The cutting efficiency of the blade 200, as well as the degree of hemostasis, will vary with the level of driving power applied, the cutting rate or force applied by the surgeon to the blade, the nature of the tissue type and the vascularity of the tissue.

As can be seen in FIG. 2, the ultrasonic instrument 110 is supported within the housing 102 by a tailpiece drive adapter 130 and a distal handpiece adapter 134. The tailpiece drive adapter 130 is rotatably supported within housing 102 by a proximal bearing 132 and is non-rotatably coupled to the output shaft 192 of the motor 190. See FIG. 2. The tailpiece drive adapter 130 may be pressed onto the housing 112 of the ultrasonic instrument 110 or, for example, be attached to the housing 112 by setscrews or adhesive. The distal handpiece adapter 134 may be pressed onto a distal end 113 of the handpiece housing 112 or be otherwise attached thereto by set screws or adhesive. The distal handpiece adapter 134 is rotatably supported in the housing 102 by a distal bearing 136 that is mounted within housing 102.

When power is applied to motor 190, motor 190 applies a "gross rotational motion" to the handpiece 110 to cause the ultrasonic surgical instrument 110 and blade 200 to rotate about central axis A-A. As used herein, the term "gross rotational motion" is to be distinguished from that "torsional ultrasonic motion" that may be achieved when employing a non-homogeneous formed ultrasonic blade. The term "gross rotational motion" instead encompasses rotational motion that is not solely generated by operation of the ultrasonic transducer assembly 114.

To provide the ultrasonic instrument 110 with power from the ultrasonic generator 12, a slip ring assembly 150 may be employed. As can be seen in FIG. 2, conductors 151, 152 are coupled to the ultrasonic transducer assembly 114 and extend through a hollow stem portion 132 of the tail piece drive adapter 130. The hollow stem portion 132 is attached to the drive shaft 192 of the motor 190 and is free to rotate within the slip ring assembly 150. A first inner contact 154 is attached to the hollow stem portion 132 for rotational travel therewith about axis A-A. The first inner contact 154 is positioned for rotational contact with a fixed outer contact 156 within the slip ring assembly 150. The contacts 154, 156 may be provided in the form of concentrically arranged rings. Conductors 157, 158 are coupled to the fixed outer contact 156 and form generator cable 14. Conductors 191 and 193 are attached to the motor and form motor cable 74 and conductors 195, 197 are attached to encoder 194 and form encoder cable 70. Rotation of the motor shaft 192 results in the rotation of the tailpiece drive adapter 130 and the ultrasonic instrument 110 attached thereto about axis A-A. Rotation of the motor drive shaft 192 also results in the rotation of the inner contact 154. Ultrasonic signals from the ultrasonic generator 12 are transferred to the inner contact 154 by virtue of contact or "electrical communication" between the inner contact 154 and the outer contact 156. Those signals are transmitted to the ultrasonic transducer assembly 114 by conductors 151, 152. In other alternative embodiments, the slip ring assembly may employ use of conventional pogo pins that engage concentric ring contacts. Other slip ring arrangements could also be employed.

Various embodiments also include a distal nosepiece 160 that may be removably attached to the distal end 103 of the housing 102 by fasteners 161. See FIG. 5. One or more shim members 162 may be positioned between the distal end 103 and the nosepiece 160 to facilitate coaxial attachment between the housing 102 and the nosepiece 160. The nosepiece 160 may be fabricated from, for example, stainless steel or polycarbonate. In various embodiments, the distal end 202 of the blade 200 extends through a hollow coupler segment 210 that is journaled within an inner sheath seal 212. Inner sheath seal 212 may comprise, for example, polytetrafluoroethylene (PTFE"), and serve to establish a substantially fluid-tight and/or airtight seal between the coupler segment 210 and the nosepiece 160. Also in the embodiment of FIG. 4, an inner sheath 220 may be attached to the hollow coupler segment 210 by, for example, welding or the hollow coupler segment 210 may comprise an integral portion of the inner sheath 220. In one embodiment, a blade pin/torquing member 216 may extend transversely through the blade member 200 and the hollow coupler segment 210 to facilitate movement of the inner sheath 220 with the blade member 200. One or more vented silicone bushings 214 may be journaled around the blade 200 to acoustically isolate the blade 200 from the inner sheath 220. The blade member 200 may have a proximal end 201 that is internally threaded and adapted to removably engage a threaded portion of the coupler 126. To facilitate tightening of the blade 200 to the coupler 126, a tightening hole 108 (FIG. 2) may be provided through the housing 102 to enable a tool (e.g., Allen wrench) to be inserted therethrough into a hole 131 in the tail piece drive adapter 130 to prevent the rotation of the ultrasonic surgical instrument 110 and coupler 126 attached thereto.

Once the blade 200 has been screwed onto the coupler 126, the user may remove the Allen wrench or other tool from holes 108, 131 and insert a threaded plug (not shown) into hole 108 to prevent fluids/debris from entering the housing 102 therethrough.

Figure 4:
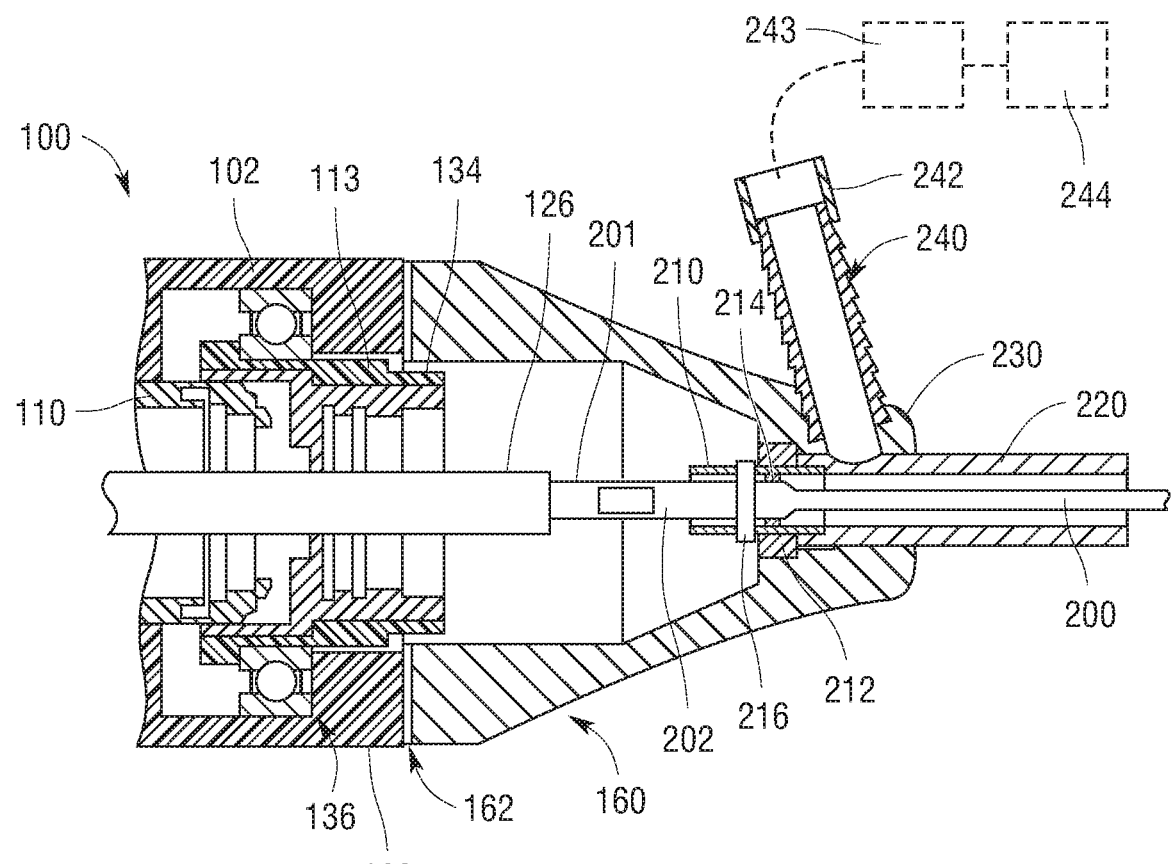
FIG. 4 is a cross-sectional view of a portion of a non-limiting nosepiece embodiment.
Figure 5:
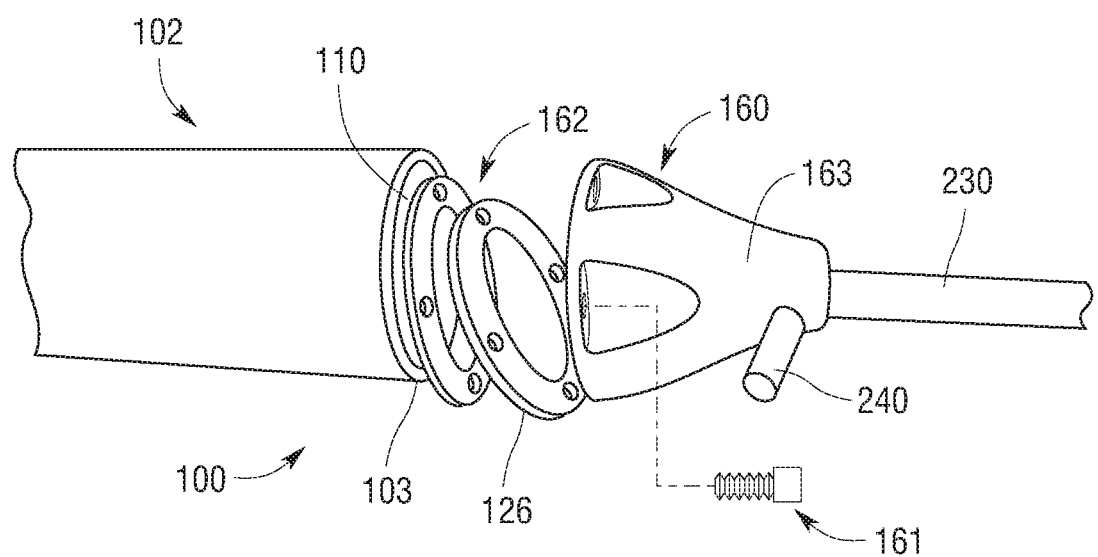
FIG. 5 is a partial exploded assembly view of a non-limiting nosepiece embodiment.

Also in various embodiments, an outer sheath 230 may be coaxially aligned with the inner sheath 220 and blade member 200 and be attached to a distal end 163 of nosepiece 160 by, for example, welding, brazing, overmolding or pressfit. As can be seen in FIG. 4, a suction port 240 may be attached to the nosepiece 160 to communicate with the hollow outer sheath 230. A flexible tube 242 may be attached to the suction port 240 and communicate with a collection receptacle 243 that is coupled to a source of vacuum, generally depicted as 244. Thus, the outer sheath 230 forms a suction path extending around the inner sheath 220 that begins at a distal tip of the outer sheath 230 and goes out through the suction port 240. Those of ordinary skill in the art will appreciate that alternate suction paths are also possible. In addition, in alternative embodiments, the inner sheath 220 is omitted.

Various embodiments of the surgical system 10 provide the ability to selectively apply ultrasonic axial motion to the blade 200 and gross rotational motion to the blade 200 as well. If desired, the clinician may simply activate the ultrasonic transducer assembly 114 without activating the motor 190. In such cases, the instrument 100 may be used in ultrasonic mode simply as an ultrasonic instrument. Frequency ranges for longitudinal ultrasonic motion may be on the order of, for example, 30-80 kHz. Similarly, the clinician may desire to active the motor 190 without activating the ultrasonic transducer assembly 114. Thus, gross rotational motion will be applied to the blade 200 in the rotation mode, without the application of longitudinal ultrasonic motion thereto. Gross rotational speeds may be, for example, on the order of 1-6000 rpm. In other applications, the clinician may desire to use the instrument 100 in the ultrasonics and rotational modes wherein the blade 200 will experience longitudinal ultrasonic motion from the transducer assembly 114 and gross rotational motion from the motor. Oscillatory motion of, for example, 2 to 10 revolutions per cycle (720 to 3600 degrees) or continuous unidirectional rotation may be achieved. Those of ordinary skill in the art will readily appreciate that various embodiments of the surgical system 10 may be affectively employed in connection with arthroscopic as well as other surgical applications.

At least one non-limiting embodiment may further include a control arrangement 170 on the housing 102. See FIG. 2. The control arrangement 170 may communicate with the control module 24 by multi-conductor cable 171. The control arrangement 170 may include a first button 172 for activating/deactivating a "dual" mode that includes the "ultrasonic mode" and "rotational mode". In such arrangements, the control module 24 may be pre-programmed to provide a pre-set amount of gross rotational motion to the blade 200. The control arrangement 170 may further include a second button 174 for activating/deactivating the rotational mode without activating the ultrasonics mode to thereby cut without hemostasis. The control arrangement 170 may also include a third button 176 for activating/deactivating a "coagulation mode" wherein the motor 190 drives to a pre-set rotational orientation and then "parks" or deactivates, thereby exposing the ultrasonic blade surface at the distal end of the outer sheath 240 as will be discussed in further detail below. Also in this mode, the ultrasonic transducer assembly 114 may be powered to provide spot coagulation or in an alternative embodiment, the clinician may simply activate a spot coagulation button 77 which activates the ultrasonic transducer assembly 114 for a preset time period of, for example, five seconds. The control arrangement may further include a button 178 to switch between ultrasonics and rotational modes. In accordance with various non-limiting embodiments, any combinations of the aforementioned functions/modes may be combined and controlled by one or more buttons without departing from the spirit and scope of the various non-limiting embodiments disclosed herein as well as their equivalent structures.

Those of ordinary skill in the art will understand that the housing member 102 and the mounting adapters 130 and 134 may be configured to operably support various different types and shapes of ultrasonic handpieces therein that may be independently used apart from the surgical instrument 100. Thus, the control system 20 and instrument 100 may be provided in "kit form" without the ultrasonic handpiece 110 to enable the purchaser to install their existing ultrasonic handpiece therein without departing from the spirit and scope of the various non-limiting embodiments disclosed herein as well as their respective equivalent structures.

Figure 6:
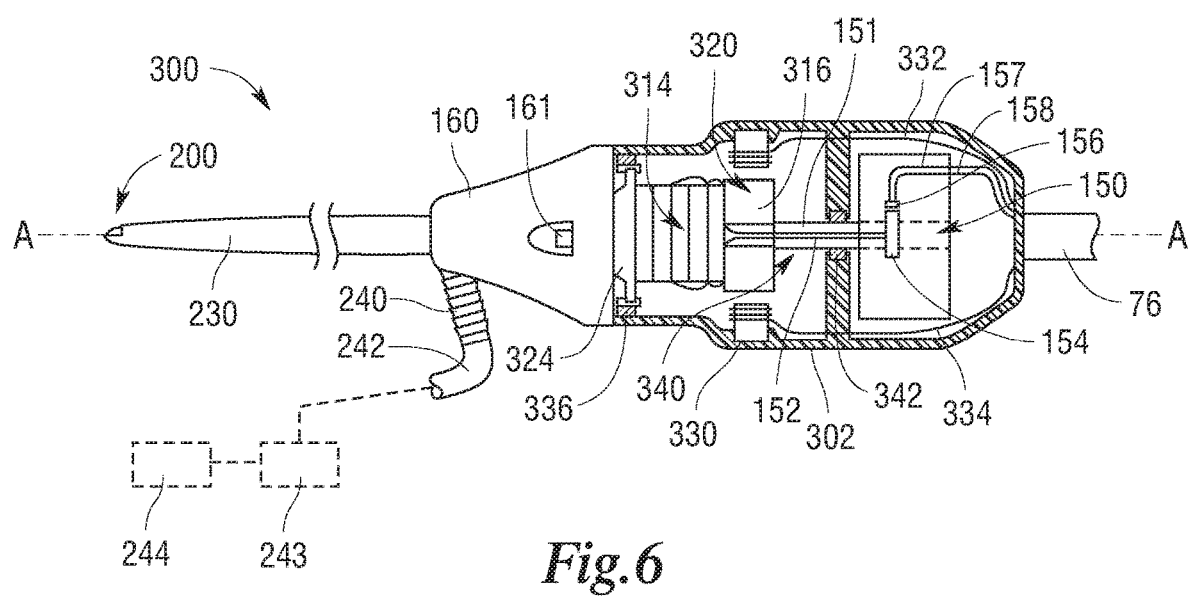
FIG. 6 is a partial cross-sectional view of a non-limiting embodiment of a surgical instrument handpiece.
Figure 7:
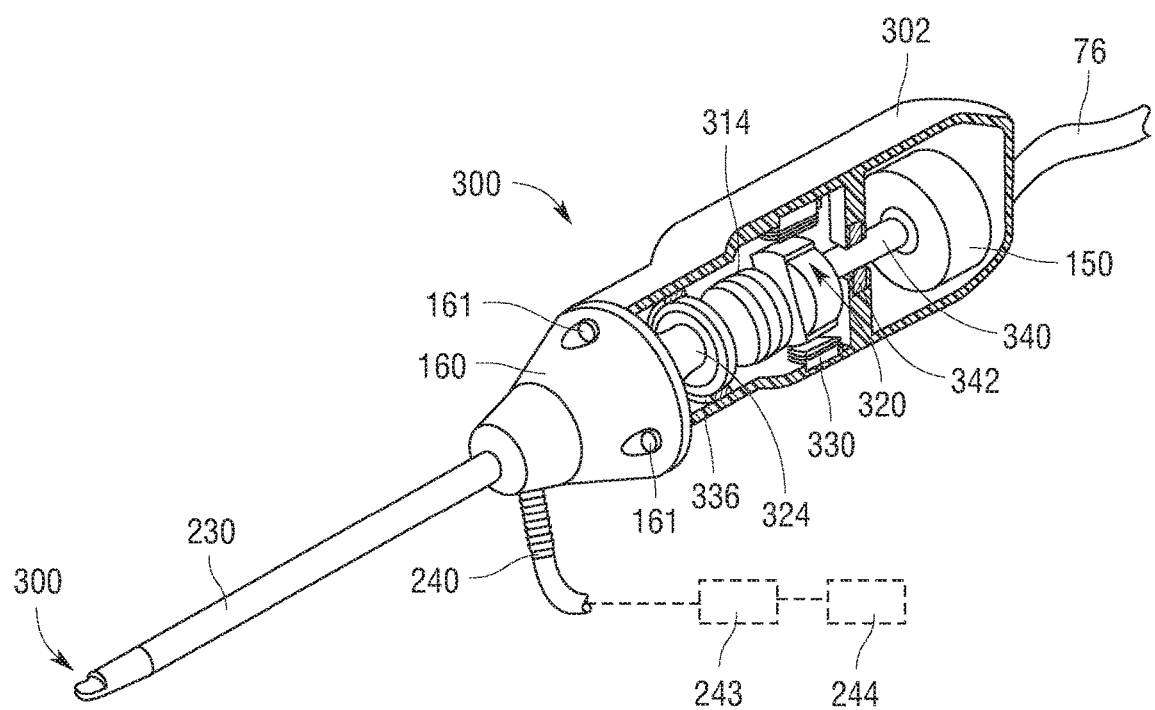
FIG. 7 is a perspective view of the non-limiting surgical instrument handpiece embodiment of FIG. 6.

FIGS. 6 and 7 illustrate another surgical instrument 300 wherein like numbers previously used to describe the various embodiments discussed above are used to designate like components. In these embodiments, the surgical instrument 300 includes a housing 302 that houses a transducer assembly 314 that is attached to an ultrasonic horn 324. The ultrasonic horn 324 may be coupled to the proximal end 201 of the blade 200 in the manner described above. The ultrasonic horn 324 may be rotatably supported within the housing 302 by a distal bearing 336. A nosepiece 160 may be attached to the housing 302 by fasteners 161 in the manner described above.

In this embodiment, the ultrasonic transducer assembly 314 has magnets 316 embedded or otherwise attached thereto to form an integral motor rotor, generally designated as 320. A motor stator ring 330 is mounted within the housing 302 as shown. Conductors 332, 334 are attached to the motor stator ring 330 and pass through the common sheath 76 to be attached to the motor cable 33 in the control system 20 as described above. A hollow shaft 340 extends through the motor rotor 320 to form a passage for conductors 151, 152. Conductors 151, 152 are coupled to the ultrasonic transducer assembly 314 and an inner contact 154. The inner contact 154 is attached to a portion of the hollow shaft 340 that rotatably extends into a slip ring assembly 150 that is also supported within the housing 302. The hollow shaft 340 is rotatably supported within the housing 302 by a proximal bearing 342. The slip ring assembly 150 is fixed (i.e., non-rotatable) within the housing 302 and includes a fixed outer contact 156 that is coupled to conductors 157, 158 that form generator cable 14 as was described above. When power is supplied to the motor stator 330, the rotor 320 and the integral ultrasonic transducer 314 are caused to rotate about axis A-A. Ultrasonic signals from the ultrasonic generator 12 are transferred to the inner contact 154 by virtue of rotating contact or electrical communication between the inner contact 154 and the outer contact 156. Those signals are transmitted to the ultrasonic transducer assembly 314 by conductors 151, 152. The surgical instrument 300 may include a control arrangement of the type described above and be used in the various modes described above. A suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the blade to tissue as will be further discussed below.

Figure 8:
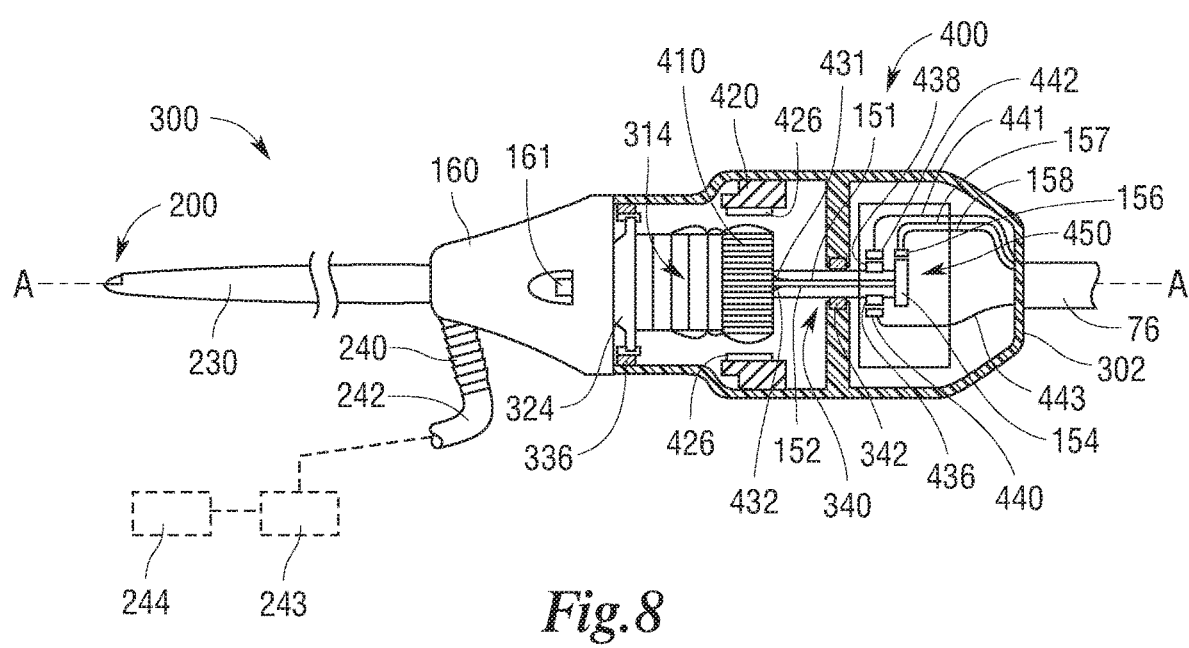
FIG. 8 is a partial cross-sectional view of another non-limiting surgical instrument handpiece embodiment.

FIG. 8 illustrates another surgical instrument 400 wherein like numbers previously used to describe the various embodiments discussed above are used to designate like components. In these embodiments, the surgical instrument 400 includes a housing 302 that houses an ultrasonic transducer assembly 314 that is attached to an ultrasonic horn 324. The ultrasonic horn 324 may be coupled to the proximal end 201 of the blade 200 in the manner described above. The ultrasonic horn 324 may be rotatably supported within the housing 302 by a distal bearing 336. A nosepiece 160 may be attached to the housing 302 in the manner described above.

In this embodiment, a brushed motor 410 is integrally attached to the ultrasonic transducer assembly 314. As used herein "integrally attached" means directly attached to or otherwise formed with the ultrasonic transducer assembly 314 for travel therewith. The term "integrally attached" as used with reference to the attachment of the brushed motor 410 to the ultrasonic transducer assembly 314 does not encompass those configurations wherein the ultrasonic transducer assembly is attached to the motor via a driven shaft arrangement. Also in this embodiment, magnets 426 are provided in a stator ring 420 that is fixed within the housing 302. Conductors 432, 434 extend through a hollow shaft 340 that is attached to the brushed motor 410. The hollow shaft 340 is rotatably supported within the housing 302 by proximal bearing 342. The motor conductor 432 is attached to a first inner motor contact 436 and the motor conductor 434 is attached to a second inner motor contact 438. The first and second inner motor contacts 436, 438 are supported on the portion of the hollow shaft 340 that extends into a slip ring assembly, generally designated as 450. The slip ring assembly 450 is fixed (i.e., non-rotatable) within the housing 302 and includes a first outer motor contact 440 that is coupled to conductor 441 and a second outer motor contact 442 that is coupled to conductor 443. The conductors 441, 443 form motor cable 74 as was described above. When the clinician desires to apply gross rotational motion to the ultrasonic transducer assembly 314 and ultimately to the blade 200, the clinician causes power to be supplied to the brushed motor 410 from the motor drive 26.

Also in this embodiment, conductors 151, 152 are attached to the ultrasonic transducer assembly 314 and extend through the hollow shaft 340 to be coupled to inner transducer contact 154 that is attached to the hollow shaft 340. The slip ring assembly 450 includes a fixed outer transducer contact 156 that is coupled to conductors 157, 158 that form generator cable 14 as was described above. When power is supplied to the brushed motor 410, the motor 410, ultrasonic transducer assembly 314, and motor shaft 340 are caused to rotate about axis A-A. Ultrasonic signals from the ultrasonic generator 12 are transferred to the inner contact 154 by virtue of rotational sliding contact or electrical communication between the inner contact 154 and the outer contact 156. Those signals are transmitted to the ultrasonic transducer assembly 314 by conductors 151, 152. The surgical instrument 400 may include a control arrangement of the type described above and be used in the various modes described above. It will be understood that the instrument 400 may be used in rotation mode, ultrasonic mode, rotation and ultrasonic mode ("duel mode") or coagulation mode as described above. A suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the blade to tissue as will be further discussed below.

FIGS. 9-13 illustrate another surgical instrument 500 wherein like numbers previously used to describe the various embodiments discussed above are used to designate like components. In these embodiments, the surgical instrument 500 includes a housing 302 that houses a transducer assembly 530 that is attached to an ultrasonic horn 324. The ultrasonic horn 324 may be coupled to the proximal end 201 of the blade 200 in the manner described above. The ultrasonic horn 324 may be rotatably supported within the housing 302 by a distal bearing 336. A nosepiece 160 may be attached to the housing 302 in the manner described above.

This embodiment includes a motor 510 that may comprise a stepper motor of the type and construction described above and may have an encoder portion associated therewith that communicates with the control module 24 as was described above. The motor 510 may receive power from the motor drive 26 through conductors 511, 512 that comprise motor cable 74 that extends through the common sheath 76. The motor 510 has a hollow motor shaft 520 attached thereto that extends through a slip ring assembly 150. The hollow drive shaft 520 is rotatably supported within the housing 302 by a proximal bearing 342. The slip ring assembly 150 is fixed (i.e., non-rotatable) within the housing 302 and includes a fixed outer contact 156 that is coupled to conductors 157, 158 that form generator cable 14 as was described above. An inner contact 154 is mounted on the hollow drive shaft 520 and is in electrical contact or communication with outer contact 156. Conductors 151, 152 are attached to the inner contact 154 and extend through the hollow drive shaft 520 to be coupled to the ultrasonic transducer assembly 530.

Figure 9:
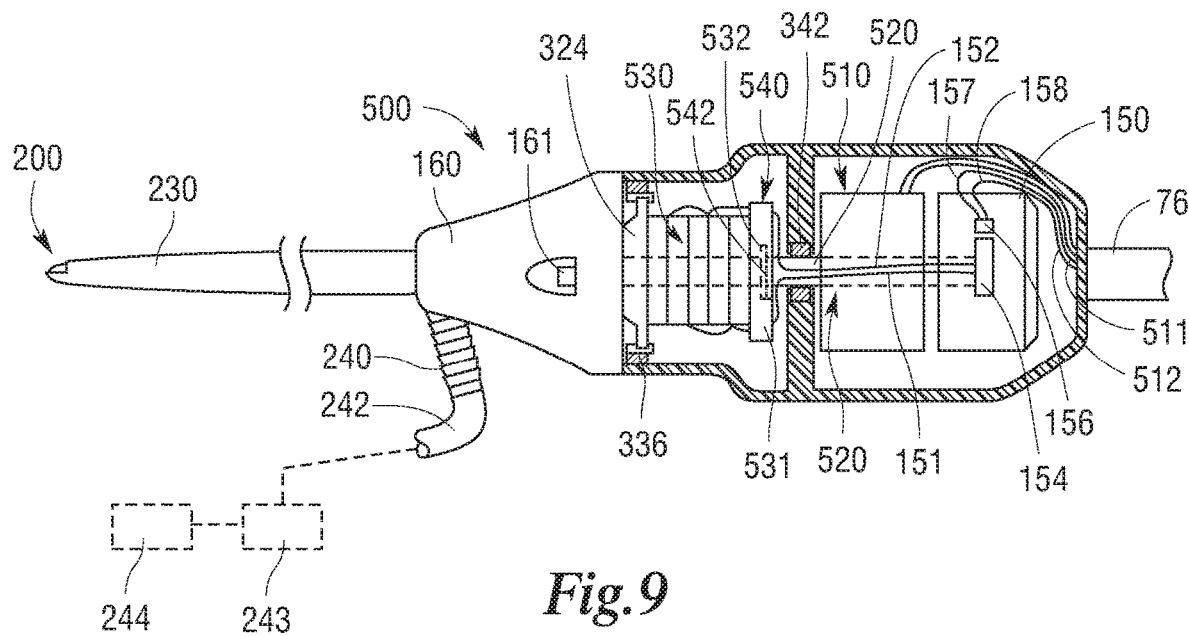
FIG. 9 is a partial cross-sectional view of another non-limiting surgical instrument handpiece embodiment.
Figure 10:
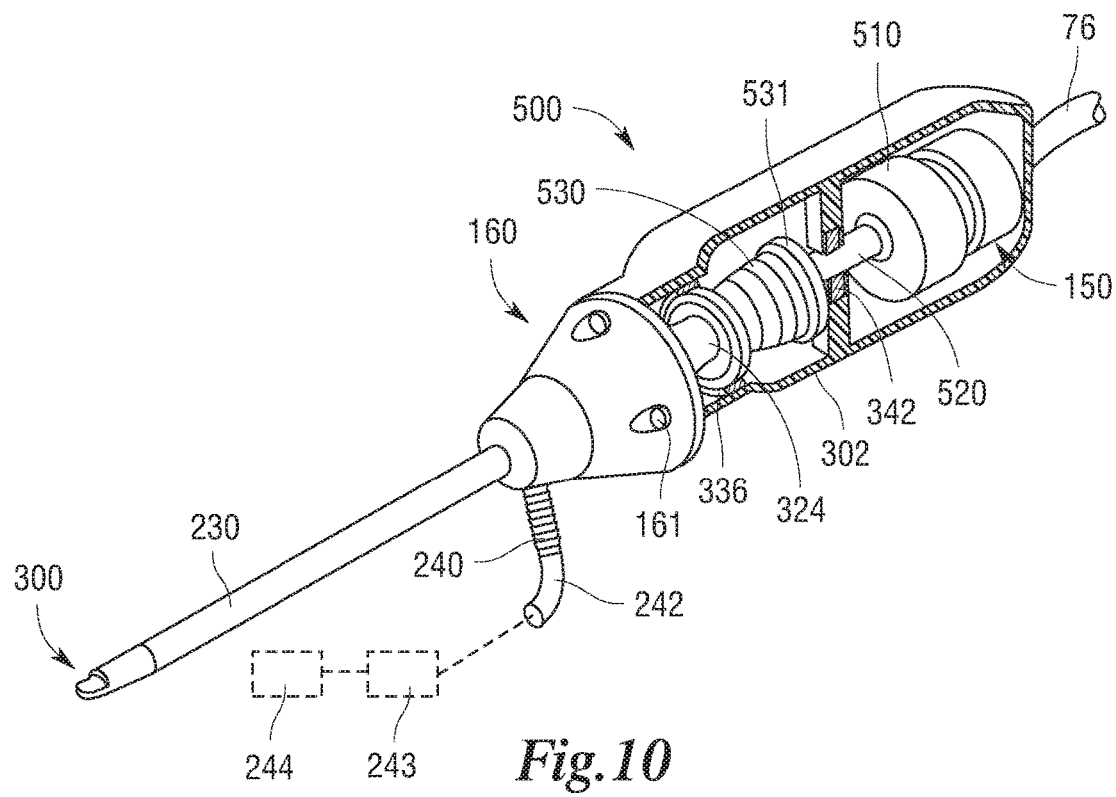
FIG. 10 is a perspective view of the surgical instrument handpiece embodiment depicted in FIG. 9.
Figure 11:
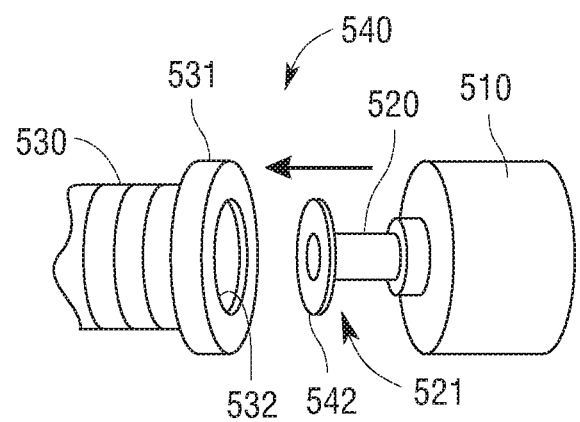
FIG. 11 is a partial exploded assembly view of a non-limiting coupling assembly embodiment for coupling a motor to a transducer assembly.
Figures 12, 13:
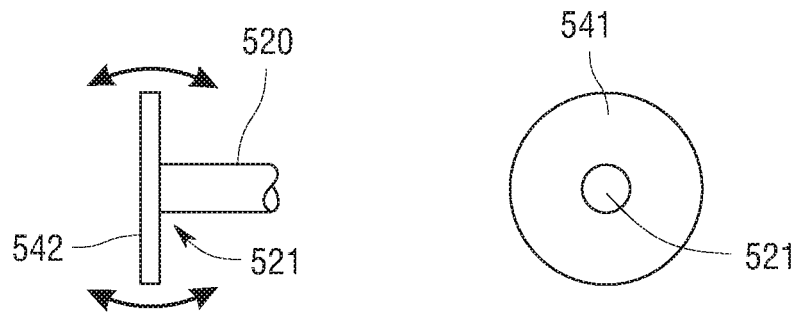
FIG. 12 is a side view of a thin plate member and drive shaft arrangement of a non-limiting coupling assembly embodiment.
FIG. 13 is an end view of the non-limiting thin plate member embodiment of FIG. 12.

In various embodiments, to facilitate ease of assembly and also to acoustically isolate the motor from the ultrasonic transducer assembly 530, the hollow drive shaft 520 may be detachably coupled to the ultrasonic transducer stack 530 by a coupling assembly, generally designated as 540. As can be seen in FIGS. 9, 11, and 12, the coupling assembly 540 may include a thin plate member 542 that is attached to a distal end 521 of the hollow drive shaft 520. The thin plate member 542 may be fabricated from a material that has a relatively low stiffness in the axial direction and a high stiffness in rotation. See FIG. 12. For example, the thin plate member 542 may be fabricated from 0.008 inch thick Aluminum 7075-T651 and be attached to the distal end 521 of the hollow drive shaft 520 by, for example, by a press fit or brazing. The coupling assembly 540 may further include a proximal end mass or flange portion 531 of the ultrasonic transducer assembly 530. The proximal end mass 531 may comprise, for example, a flange manufactured from stainless steel which is attached to the ultrasonic transducer assembly 530 by, for example, a bolted or other connection. As can be seen in FIG. 11, the end mass 531 has a hole 532 sized to receive the thin plate member 542 therein. In various embodiments, the thin plate member 542 may be sized to be pressed into the hole 532 such that rotation of the thin plate member 542 about axis A-A will cause the ultrasonic transducer assembly 530 to rotate about axis A-A. In other embodiments, a separate fastener plate (not shown) or snap rings (not shown) or snap features (not shown) may be provided to retain the thin plate member 542 in non-rotatable engagement with the end mass 531 of the ultrasonic transducer assembly 530. Such arrangements serve to minimize the transmission of acoustic vibrations to the motor from the ultrasonic transducer assembly.

Figures 14, 15:
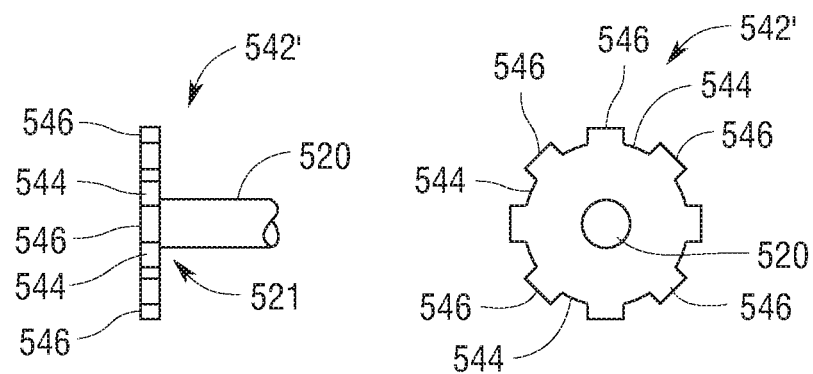
FIG. 14 is a side view of a non-limiting thin plate member and drive shaft arrangement of another non-limiting coupling assembly embodiment.
FIG. 15 is an end view of the non-limiting thin plate member embodiment of FIG. 14.

FIGS. 14 and 15 illustrate an alternative thin plate member 542' that may be employed. In this embodiment, the thin plate member 542' has a plurality of radial notches 544 provided therein to form radial tabs 546. The hole 532 would be formed with notches (not shown) to accommodate the radial tabs 546 therein. Such arrangement may reduce the moment force applied to the shaft 520. By employing the thin plate members 542, 542' the amount of acoustic vibrations that are transferred from the ultrasonic transducer assembly 530 to the drive shaft 520 may be minimized.

When power is supplied to the motor 510, the drive shaft 520 rotates bout axis A-A which also causes the transducer assembly 530 to rotate about axis A-A. When the clinician desires to power the ultrasonic transducer assembly 530, power is supplied form the ultrasonic generator 12 to the fixed contact 156 in the slip ring assembly 150. Power is transmitted to the ultrasonic transducer assembly 530 by virtue of rotational sliding contact or electrical communication between the inner contact 154 and the outer contact 156. Those signals are transmitted to the ultrasonic transducer assembly 530 by conductors 151, 152. The surgical instrument 500 may include a control arrangement of the type described above and be used in the various modes described above. It will be understood that the instrument 400 may be used in rotation mode, ultrasonic mode, rotation and ultrasonic mode ("duel mode") or coagulation mode as described above. A suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the blade to tissue as will be further discussed below.

Figure 16:
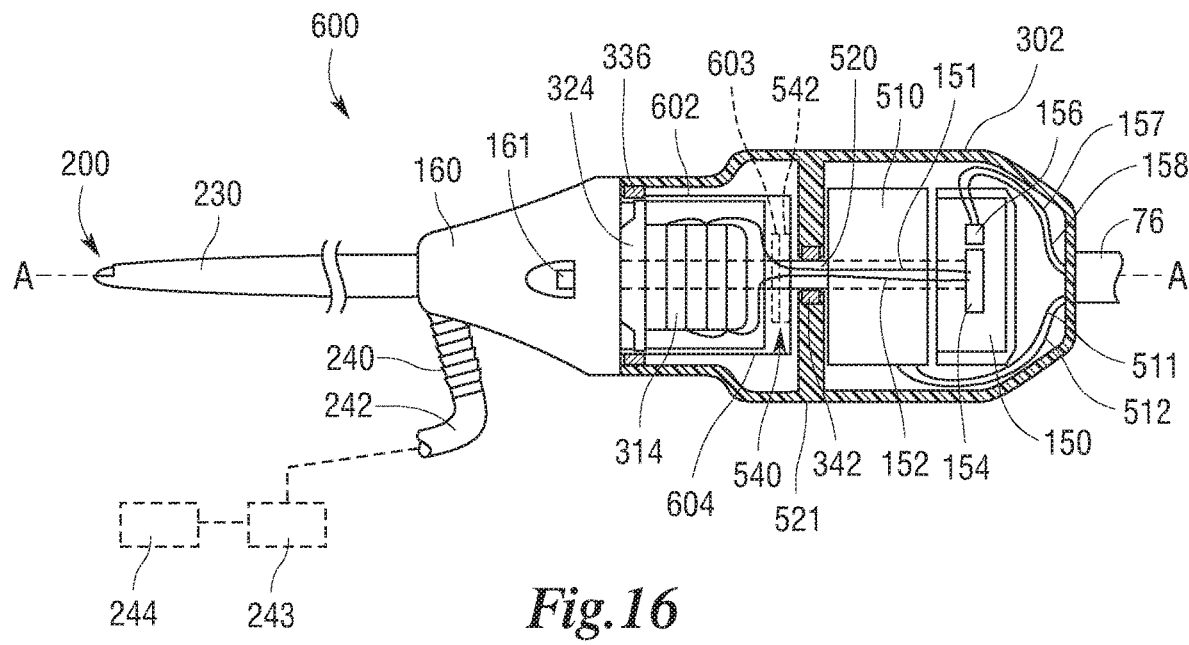
FIG. 16 is a partial cross-sectional view of another non-limiting surgical instrument handpiece embodiment.

FIG. 16 illustrates another surgical instrument 600 wherein like numbers previously used to describe the various embodiments discussed above are used to designate like components. In these embodiments, the surgical instrument 600 includes a housing 302 that houses a transducer assembly 314 that is attached to an ultrasonic horn 324. In this embodiment, the transducer assembly 314 and the ultrasonic horn 324 are attached to a PZT housing 602 that is rotatably supported within the housing 302 by a distal bearing 336. The ultrasonic horn 324 may be coupled to the proximal end of the blade 200 in the manner described above. A nosepiece 160 may be attached to the housing 302 by fasteners 161 in the manner described above.

This embodiment includes a motor 510 that may comprise a stepper motor of the type and construction described above. The motor 510 may have an encoder associated therewith that communicates with the control module 24 (FIG. 1) as was described above. The motor 510 may receive power from the motor drive 26 (FIG. 1) through conductors 511, 512 that comprise motor cable 74 that extends through the common sheath 76. The motor 510 has a hollow motor shaft 520 attached thereto that extends through a slip ring assembly 150. The hollow drive shaft 520 is rotatably supported within the housing 302 by a proximal bearing 342.

The slip ring assembly 150 is fixed (i.e., non-rotatable) within the housing 302 and includes a fixed outer contact 156 that is coupled to conductors 157, 158 that form generator cable 14 as was described above. An inner contact 154 is mounted on the rotatable hollow drive shaft 520 and is in electrical contact or communication with outer contact 156. Conductors 151, 152 are attached to the inner contact 154 and extend through the hollow drive shaft 520 to be coupled to the ultrasonic transducer assembly 314. In various embodiments, to facilitate ease of assembly and also acoustically isolate the motor 510 from the ultrasonic transducer assembly 314, the hollow drive shaft 520 may be detachably coupled to the PZT housing 602 by a coupling assembly, generally designated as 540. The coupling assembly 540 may include a thin plate member 542 that is attached to a distal end 521 of the hollow drive shaft 520. As discussed above, the thin plate member 542 may be fabricated from a material that has a relatively low stiffness in the axial direction and a high stiffness in rotation. The PZT housing 602 has a proximal end portion 604 that has a hole 603 sized to receive the thin plate member 542 therein. In various embodiments, the thin plate member 542 may be sized to be pressed into the hole 603 such that rotation of the thin plate member 542 about axis A-A will cause the PZT housing 602 and ultrasonic transducer assembly 314 and ultrasonic horn 324 to rotate about axis A-A. In other embodiments, a separate fastener plate (not shown) or snap rings (not shown) or snap features (not shown) may be provided to retain the thin plate member 542 in non-rotatable engagement with the proximal end portion 604 of the PZT housing 602. This embodiment could also employ the thin plate member 542' as was discussed above.

When power is supplied to the motor 510, the drive shaft 520 rotates about axis A-A which also causes the PZT housing 602 and ultrasonic transducer assembly 314 to rotate about axis A-A. When the clinician desires to power the ultrasonic transducer assembly 314, power is supplied from the ultrasonic generator 12 to the fixed contact 156 in the slip ring assembly 150. Power is transmitted to the ultrasonic transducer assembly 314 by virtue of rotational sliding contact or electrical communication between the inner contact 154 and the outer contact 156. Those signals are transmitted to the ultrasonic transducer assembly 314 by conductors 151, 152. The surgical instrument 500 may include a control arrangement of the type described above and be used in the various modes described above. It will be understood that the instrument 400 may be used in rotation mode, ultrasonic mode, rotation and ultrasonic mode ("duel mode") or coagulation mode as described above. A suction may be applied between the blade 200 and outer sheath 230 through port 240. A collection receptacle 243 and source of suction 240 may be attached to the port 240 by tube 242. The distal end of the blade is exposed through a window in the distal end of the outer sheath 230 to expose the blade to tissue as will be further discussed below.

In an effort to reduce the overall size of the housing 302 employed in each of the instruments 300, 400, 500, and 600, the ultrasonic transducer assemblies employed in each of those respective instruments could be replaced with a half wave transducer that is physically shorter in length.

Ultrasonic Blade and Sheath Embodiments

Current arthroscopic tools include punches, reciprocating shavers, and radio frequency (RF) powered devices. Mechanical devices such as punches and shavers tend to create minimal tissue damage, but can sometimes leave behind ragged cut lines which are not desirable. RF powered blades can leave behind smoother cut lines and also ablate large volumes of soft tissue. However, such devices can create more tissue damage than pure mechanical instruments. The various non-limiting surgical instruments embodiments described above provide a host of advantages over conventional RF powered surgical instruments as well as conventional mechanical shavers that employ a rotating tissue cutting member. As will be discussed in further detail below, additional advantages may be realized by employing the unique and novel blade and sheath configurations of various non-limiting embodiments.

Figure 19:
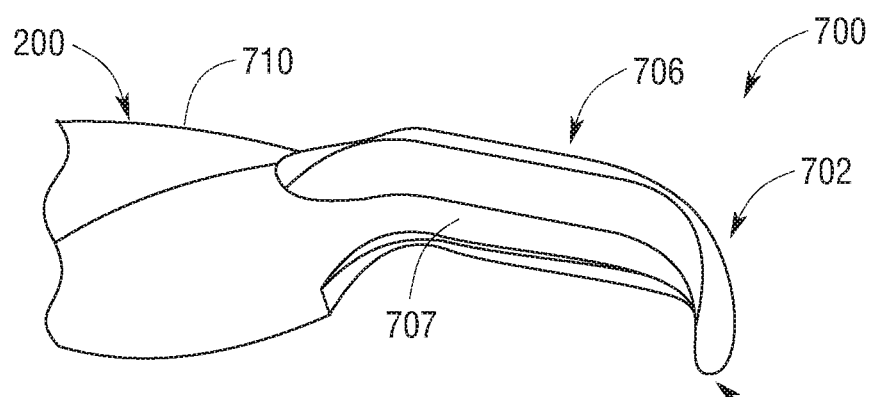
FIG. 19 is a partial bottom perspective view of the blade of FIGS. 17 and 18.
Figure 20:
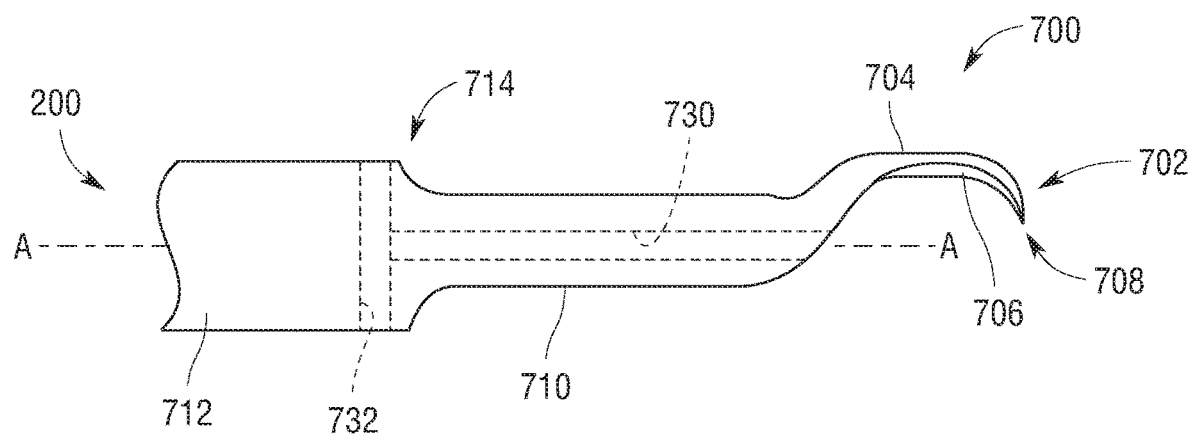
FIG. 20 is a side view of a portion of another non-limiting blade embodiment.

FIGS. 17-21 illustrate one form of blade 200 and outer sheath 230 that may be employed in connection with the various surgical instruments described above. As can be seen in those Figures, the blade 200 may have a distal end portion 700 and the outer sheath 230 may have a distal end portion 720. The blade 200 may be fabricated from, for example, titanium and the outer sheath 230 may be fabricated from, for example, Poly ether ether ketone ("PEEK"), Ultem®, or stainless steel. As was discussed above, the blade 200 may have a waveguide or proximal end portion that is configured to be threadably or otherwise attached to an ultrasonic horn 324 (FIGS. 6-10 and 16) in a known manner. The distal end portion 700 of the blade 200 may have a curved tip portion 702 formed thereon. The curved tip 702 may have an arcuate top segment 704 that has a cutting edge 706 formed on each lateral side 705. The cutting edges 706 may terminate distally in a common, substantially pointed distal end 708. The pointed distal end 708 may be relatively blunted or the pointed distal end 708 may have a relatively sharpened point. As can be seen in FIG. 20, the pointed distal end 708 may curve inwardly to about the central axis A-A of the blade. As can be seen in FIG. 19, in various embodiments, the cutting edges 706 may not intersect each other but may be separated by a center portion 707. As can be seen in FIG. 20, the blade 200 may have a reduced neck portion 710 that protrudes distally from a waveguide or proximal blade portion 712. A node 714 may be established at the area where the neck portion 710 protrudes from the proximal portion 712.

Figure 17:
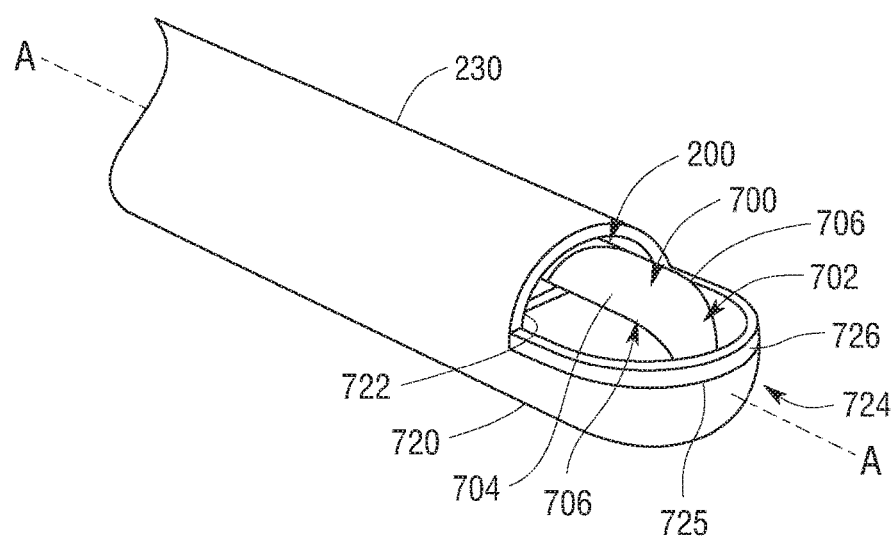
FIG. 17 is a partial perspective view of a non-limiting outer sheath and blade embodiment.
Figure 18:
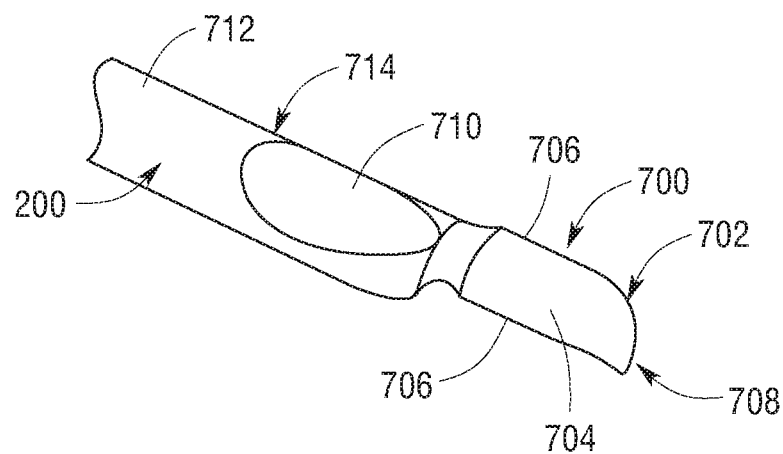
FIG. 18 is a partial perspective view of the non-limiting blade embodiment depicted in FIG. 17.

As can be seen in FIG. 17, the outer sheath 230 also has a distal end portion 720 that has a window or opening 722 formed therein to expose the distal end portion 700 of the blade 200. As can be further seen in FIG. 17, the outer sheath 230 may comprise a hollow cylinder that has a substantially blunted end 724. In various embodiments, the window 722 extends for one half of the circular cross-section of the sheath 230. Such window configuration forms an arcuate ledge 725 that extends around the blunted end 724. In various embodiments, the outer sheath 230 may be fabricated from, for example, Poly ether ether ketone ("PEEK"), Ultem®, or stainless steel. To prevent metal-to-metal contact between the cutting edges 706 on the distal end portion 700 of the blade 200 and the ledge 725, a polymer fender 726 may be attached by, for example, adhesive or a T-slot around the ledge 724. See FIG. 17. Fender 726 may be fabricated from, for example, Teflon®, silicone or other reduced or "low friction" material. The fender 726 may be sized to produce an interference fit of, for example, 0.005 inches with the cutting edges 706 and the pointed distal end 708.

In use, as the blade 200 is rotated about axis A-A within the outer sheath 230 and introduced to tissue, the tissue is drawn into the window 722 by means of the suction applied between the inner sheath 220 (FIG. 4), and the outer sheath 230 as was described above. The tissue drawn into the window 722 is then cut as the cutting edges 706 are rotated past the fender 726 and the cut tissue may pass between the inner sheath 220 and outer sheath 230 and out through the suction port 240 (FIGS. 4, 6-10, and 16) to the collection receptacle 243 (FIGS. 4, 6-10, and 16).

Figure 21:
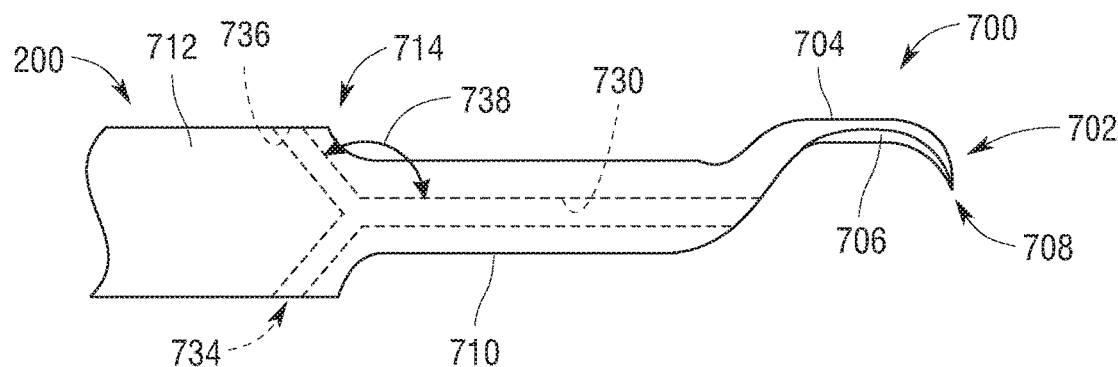
FIG. 21 is a side view of a portion of another non-limiting blade embodiment.

In another embodiment, an axial suction passage 730 may be provided through the neck portion 710 of the blade 200. See FIG. 20. The axial suction passage 730 may communicate with a transverse suction passage 732 in the area of node 714. Thus, the cut tissue may pass through the passages 730, 732 and out between the inner sheath 220 and outer sheath 230 and out through the suction port 240 (FIGS. 4, 6-10, and 16) to the collection receptacle 243 (FIGS. 4, 6-10, and 16). FIG. 21 depicts an alternative embodiment wherein two exit passages 734, 736 communicate with the axial passage 730 and extend at an angle therefrom. In various embodiments, the exit passages 734,736 may extend from the axial passage 730 at an angle 738 of, for example, forty-five (45) degrees. Such arrangement may serve to reduce impedance and power losses during ultrasonic activation which might have otherwise resulted from water being drawn in through the window 722 in the outer sheath 230.

In use, the clinician may elect to rotate the blade 200 within the outer sheath 230 without applying ultrasonic motion thereto. The clinician may also elect to apply ultrasonic motion to the rotating blade or the clinician may wish apply ultrasonic motion to a parked (non-rotating) blade to use the portion of the blade exposed in the window 722 to coagulate tissue.

Figure 22:
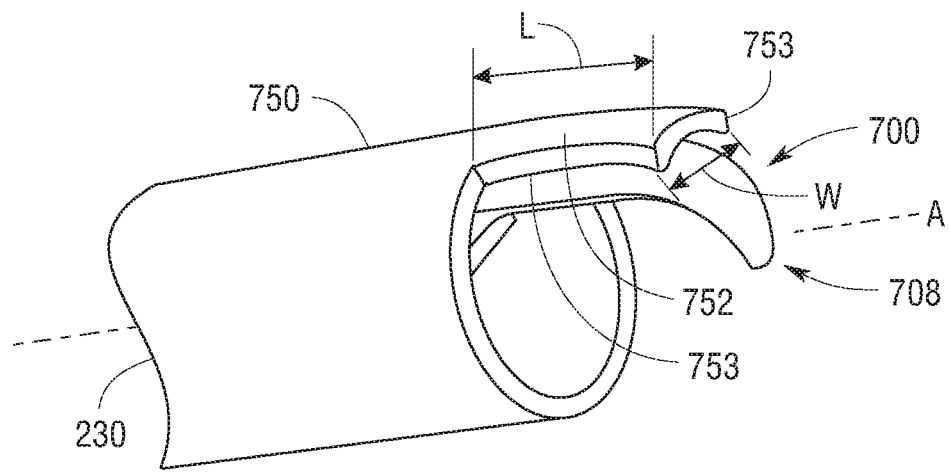
FIG. 22 is a partial perspective view of a distal end of another non-limiting outer sheath and blade arrangement.

FIG. 22 illustrates use of blade 200 in connection with an outer sheath 230 that has a distal end portion 750 that includes a distally protruding nose segment 752. In various embodiments, the nose segment 752 may have an arcuate width "W" that comprises approximately ten (10) to thirty (30) percent of the circumference of the distal end portion 750 of the outer sheath 230. The nose segment 752 may protrude distally from the end of the distal end portion 750 of the sheath 230 a length "L" that may be approximately 0.25 inches, for example. In alternative embodiments, a low friction fender or guard (not shown) may be applied to the sides 753 of the nose segment 752 if desired. These embodiments may operate in a similar manner to the previous embodiment. However, this embodiment has the added ability to cut tissue with the exposed tip. As with the other embodiments, the clinician may apply gross rotational motion to the blade 200 without ultrasonic motion or with ultrasonic motion. In another alternative method of use, the exposed tip 708 and partially exposed cutting edges 706 may be used to cut tissue when the blade is not being rotated or vibrated.

Figure 23:
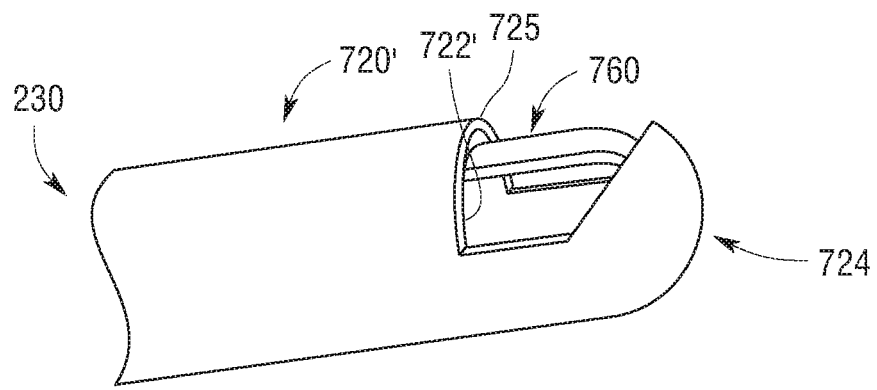
FIG. 23 is a partial perspective view of a distal end of another non-limiting outer sheath and blade arrangement.
Figure 23A:
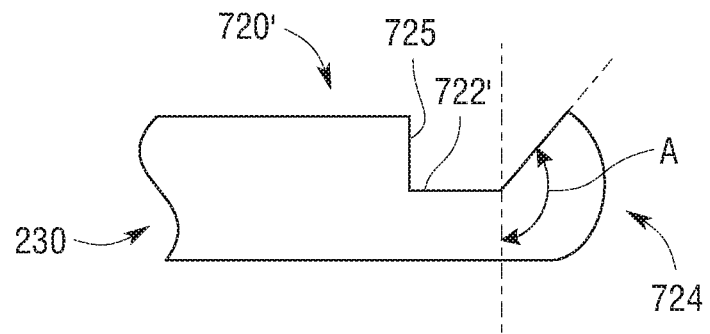
FIG. 23A is a side view of a portion of the non-limiting outer sheath embodiment depicted in FIG. 23.
Figure 24:
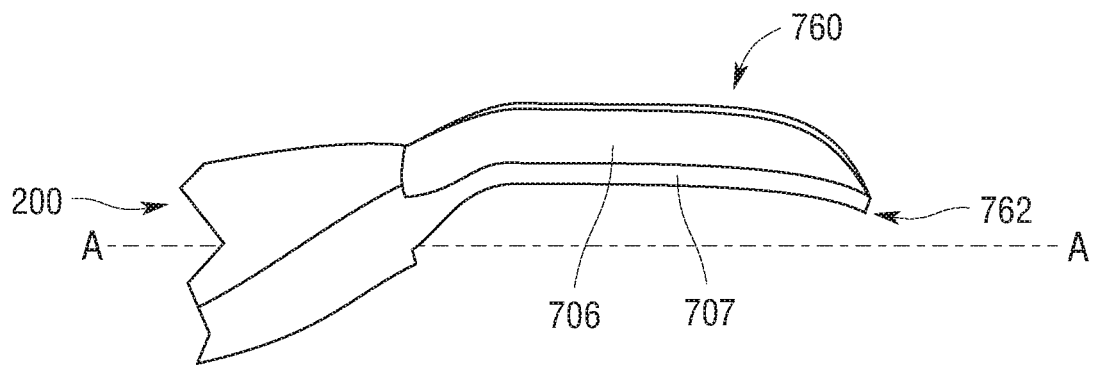
FIG. 24 is a side view of a portion of another non-limiting blade embodiment.

FIGS. 23-24 illustrate another non-limiting blade and outer sheath embodiment. In this embodiment, the blade 200 has a distal end portion 760 that is substantially similar to the distal end portion 700 of the blade configuration described above. However, the distal blade portion 760 does not hook inwardly to the same degree such that the blade tip 762 does not intersect the central axis A-A. See FIG. 24. As can be seen in FIG. 23, the window 722' in the distal end portion 720 of the outer sheath 230 does not extend the entire distance from an end wall 725 to the blunt tip 724. Thus, in this embodiment, the blunt tip 724 comprises a nose that extends more than 90° but less than 180° (i.e., angle "A" in FIG. 23A is greater than 90° but less than) 180°.

Figure 25:
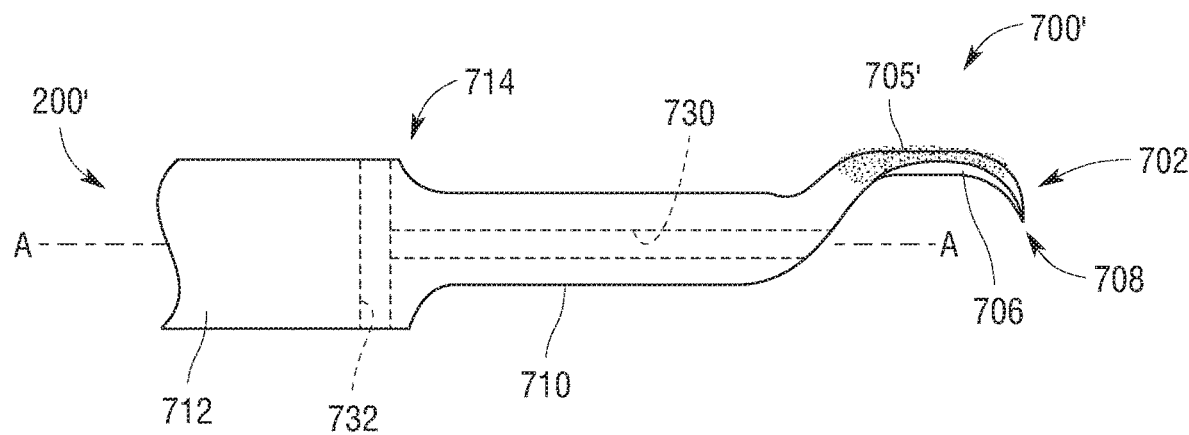
FIG. 25 is a side view of a portion of another non-limiting blade embodiment.
Figure 26:
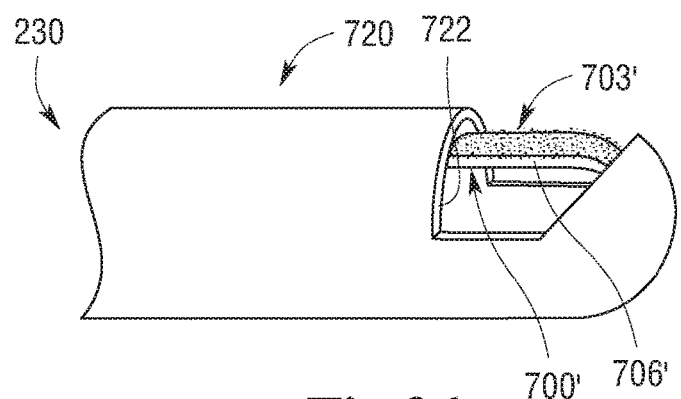
FIG. 26 is a partial perspective view the non-limiting blade embodiment of FIG. 25 within a distal end of another non-limiting outer sheath embodiment.
Figure 27:
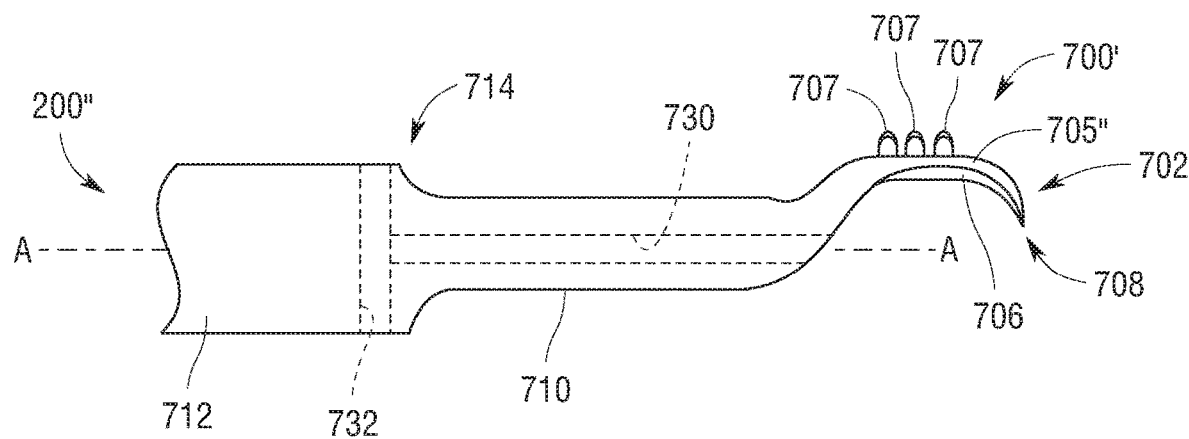
FIG. 27 is a side view of a portion of another non-limiting blade embodiment.
Figure 28:
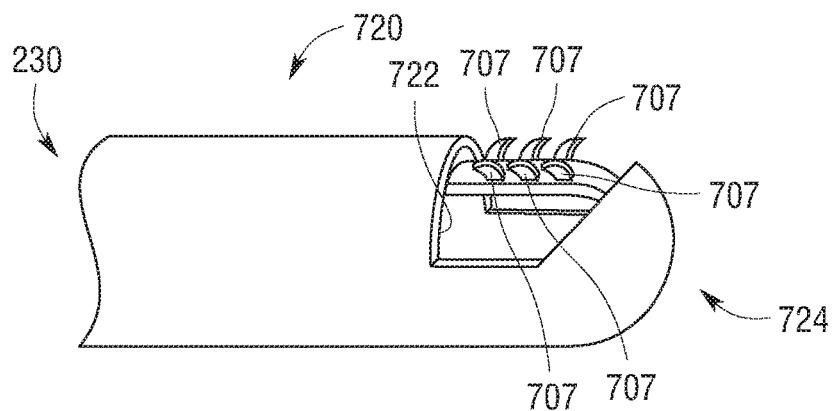
FIG. 28 is a partial perspective view the non-limiting blade embodiment of FIG. 27 within a distal end of another non-limiting outer sheath embodiment.
Figure 29:
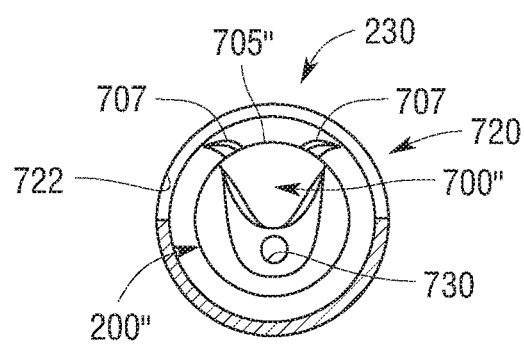
FIG. 29 is a partial cross-sectional end view of the non-limiting blade and outer sheath embodiments of FIG. 28.

FIGS. 25 and 26 depict another non-limiting blade embodiment. In this embodiment, the blade 200' may be substantially similar to blade 200 or any of the other blades described herein. In this embodiment, the distal end 700' has a roughened upper surface 705'. Such roughened surface 705' creates higher friction forces between the distal end portion 700' of the blade 200' and the tissue to draw the tissue into the window 722' in the distal end portion 720' of the outer sheath 230 (FIG. 26). By pulling more tissue into the window 722, the leading cutting edge 706' of the blade 200' may have a higher likelihood of cutting the tissue cleanly. In various embodiments, for example, the roughened surface may be formed by knurling or the upper surface may be coated with a hard material such as diamond or the like FIGS. 27-29 illustrate another non-limiting blade embodiment. In this embodiment, the blade 200" may be substantially similar to blade 200 described herein. In this embodiment, the distal end 700" has a series of radially extending cutting teeth 707 protruding outward from upper surface 705" for pulling and cutting tissue as the blade 200" is rotated within the outer sheath 230.

FIGS. 30, 31, and 32A-D illustrate another non-limiting blade and outer sheath embodiment. During use of various instruments that employ a rotatable blade within an outer sheath, it has been experienced that the tissue may get "kicked out" of the sheath window as the blade rotates therein. This can lead to reduced cutting speeds as tissue is not adequately captured and held between the cutting edges. The blade 800 of this embodiment addresses such potential shortcomings.

Figure 30:
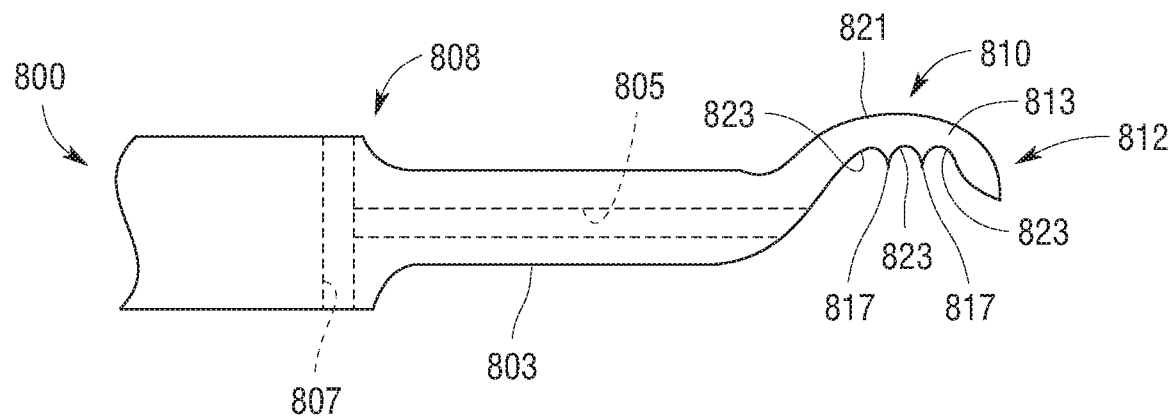
FIG. 30 is a side view of a portion of another non-limiting blade embodiment.
Figure 31:
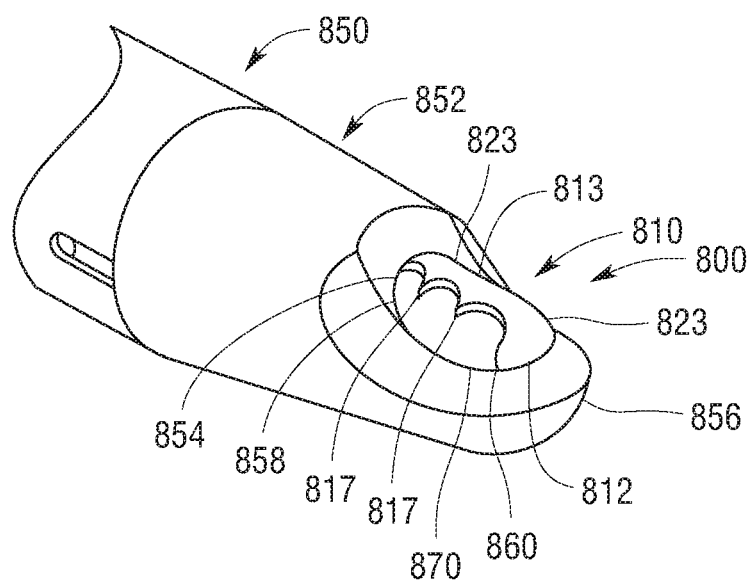
FIG. 31 is a partial perspective view of the non-limiting blade embodiment of FIG. 30 within a distal end of another non-limiting outer sheath embodiment.

As can be seen in FIG. 30, the blade 800 may be substantially the same as blade 200 except for the differences noted herein. In particular, the blade 800 may include a neck portion 803 that that terminates in a distal end portion 810. The distal end portion 810 may have a somewhat curved tip 812. A series of teeth 817 may be provided on at least one lateral side 813 or 815 of the distal end portion 810. In the embodiment depicted in FIGS. 32A-D, teeth 817 and 819 are formed on lateral sides 813, 815, respectively, of the distal end portion 810. The distal end portion 810 further has a somewhat domed top portion 821. In the embodiment shown in FIGS. 30-32D, the teeth 817 comprise relatively sharp points that define a series of arcuate openings 823 therebetween. Teeth 819 also comprise relatively sharp points that have a series of arcuate openings 825 therebetween. As shown in FIG. 30, an axial suction passage 805 may be provided through the neck portion 803 of the blade 800. The axial suction passage 805 may communicate with a transverse suction passage 807 in the area of node 808. Thus, the cut tissue may pass through the passages 805, 807 and out between the inner sheath (not shown) and outer sheath 850 and out through a suction port to a collection receptacle in the manner described hereinabove. Other suction path arrangements may also be successfully employed.

The outer sheath 850 may be substantially similar to the outer sheath 230 described above and have a distal sheath tip 852 attached thereto that has a window or opening 854 formed therein to expose the distal end portion 810 of the blade 800. See FIG. 31. The outer sheath 850 may comprise a hollow cylinder fabricated from for example, stainless steel. In various embodiments, the window 854 extends for approximately one half of the circular cross-section of the sheath 850 and forms a blade opening 858 therein. The distal sheath tip 852 may be fabricated from metal such as, for example, stainless steel such that a relatively sharp cutting edge 860 extends around the blade opening 858. For the purpose of explanation, the sharp cutting edge 860 has a first lateral cutting edge portion 862 and a second lateral cutting edge portion 864.

Figure 32A:
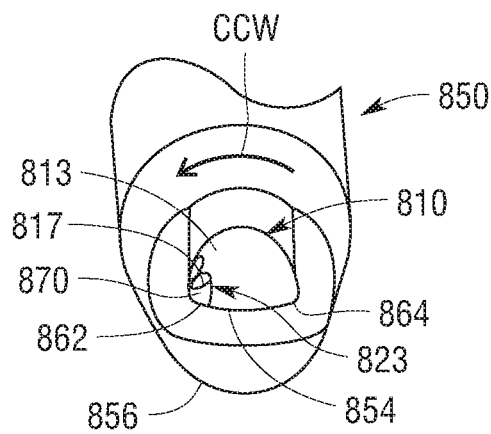
FIG. 32A illustrates a first rotational position of the non-limiting blade embodiment of FIGS. 30 and 31 within the outer sheath embodiment of FIG. 31.
Figure 32B:
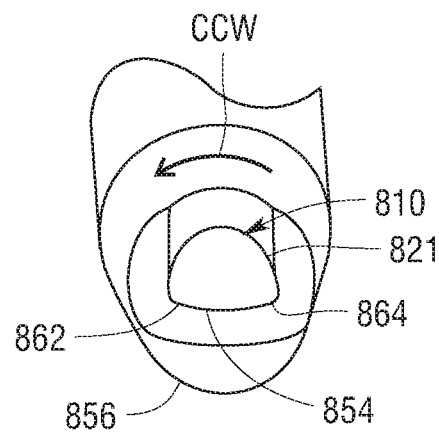
FIG. 32B illustrates a second rotational position of the non-limiting blade embodiment of FIGS. 30 and 31 within the outer sheath embodiment of FIG. 31.
Figure 32C:
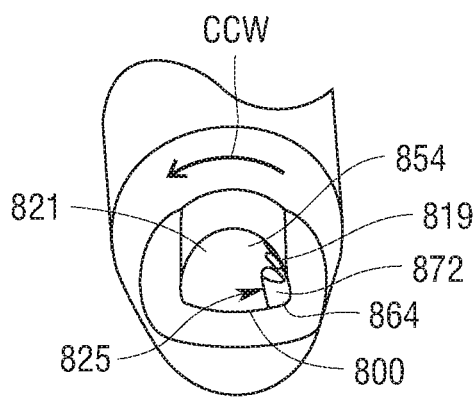
FIG. 32C illustrates a third rotational position of the blade embodiment of FIGS. 30 and 31 within the outer sheath embodiment of FIG. 31.
Figure 32D:
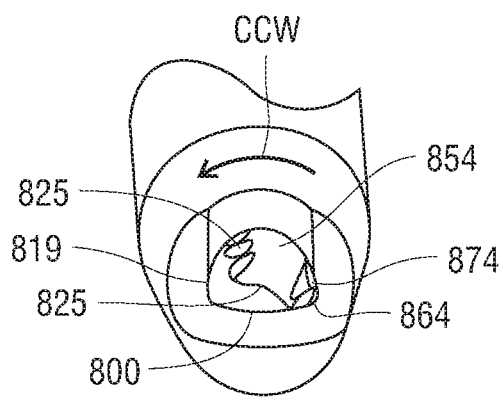
FIG. 32D illustrates a fourth rotational position of the blade embodiment of FIGS. 30 and 31 within the outer sheath embodiment of FIG. 31.

FIGS. 32A-D illustrate a sequential rotation of the blade 800 within the outer sheath 850. Turning to FIG. 32A first, the blade 800 is shown being rotated in a counter clockwise "CCW" direction. As shown in that Figure, the cutting teeth 817 on the first lateral side 813 of the blade 800 are positioned to shear tissue (not shown) between the teeth 817 and the first lateral cutting edge portion 862 of the cutting edge 860. When in that position, the arcuate openings 823 between the teeth 817 are exposed to collectively form a first lateral suction path 870 between the blade 800 and the distal sheath tip 852 to enable the tissue to be drawn therein by the suction being applied through the suction passage 805 (FIG. 30). As the rotational sequence continues, the domed upper portion 821 of the blade 800 covers the opening 854 in the distal sheath tip 852 such that there are no exposed suction paths for tissue to enter into the opening 854. As the blade continues through its rotation, FIG. 32C illustrates that the arcuate openings 825 between teeth 819 collectively form a second lateral suction path 872 between the second lateral cutting edge portion 864 and the blade 800 to enable tissue to be drawn therein. As the blade 800 continues to rotate in the CCW direction, a third suction path 874 is exposed to enable tissue to be further drawn into opening 854. Thus, such arrangement permits a sequential opening of suction paths from one lateral side of the blade opening 858 to the other to facilitate better tissue cutting. In use, the clinician may elect to rotate the blade 800 within the outer sheath 850 without applying ultrasonic motion thereto. The clinician may also elect to apply ultrasonic motion to the rotating blade or the clinician may wish apply ultrasonic motion to a parked (non-rotating) blade to use the portion of the blade exposed in the opening 854 to coagulate tissue.

Figure 33:
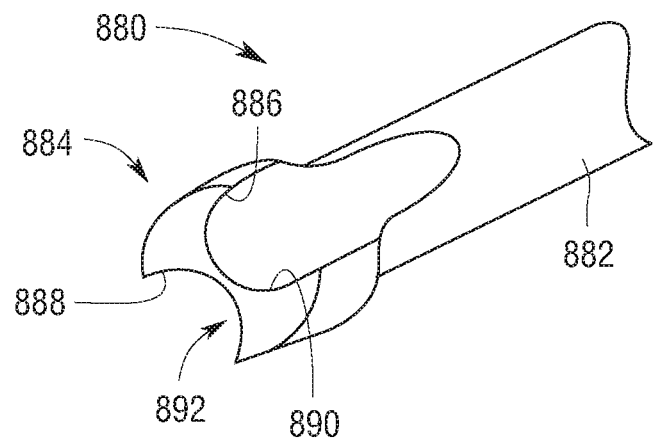
FIG. 33 is a perspective view of a portion of another non-limiting blade embodiment.
Figure 34:
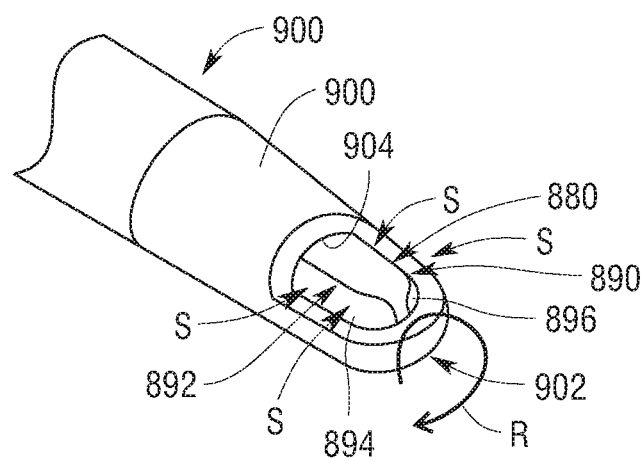
FIG. 34 is a partial perspective view of the blade embodiment of FIG. 33 within a non-limiting outer sheath embodiment.
Figure 34A:
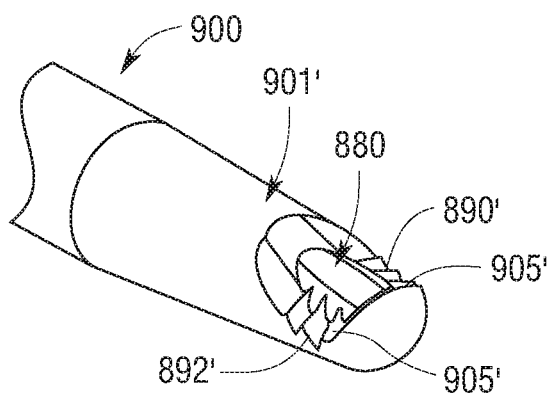
FIG. 34A is a partial perspective view of another non-limiting blade and outer sheath embodiment.

FIGS. 33 and 34 illustrate another blade embodiment 880 that may be substantially the same as blade 200 except for the differences noted below. In particular, the blade 880 may include a waveguide or proximal portion 882 that that terminates in a distal tissue cutting portion 884. The proximal portion 882 of the blade 880 may be configured to be threadably or otherwise attached to an ultrasonic horn of any of the various embodiments discussed above. The distal tissue cutting portion 884 may have opposed arcuate channels 886, 888 formed therein. The first arcuate channel 886 may define a first cutting edge 890 and the second arcuate channel 888 may define a second cutting edge 892. This blade embodiment may be used in connection with any of the outer sheath configurations described above. In the depicted embodiment, hollow outer sheath 900 is employed which may be similar to sheath 230 for example and include a distal sheath tip 901 that has rounded or blunted nose portion 902 and a window 904. The hollow outer sheath 900 may be fabricated from, for example, stainless steel and the distal sheath tip 901 may be fabricated from metal such as, for example, stainless steel. The window 904 forms an arcuate cutting edge 906 that cooperates with the cutting edges 890, 892 on the blade 880 to shear off tissue as the blade 880 is rotated within the outer sheath 900 in the various manners described above. In at least one embodiment, the proximal portion 882 of blade 880 may be sized relative to the hollow outer sheath 900 such that a clearance is provided therebetween to enable a suction to be applied thereto in the manner described above, for example. As can be seen in FIG. 34, as the blade 880 rotates (represented by arrow "R") the arcuate channels 886, 886 define openings 894, 896 between the distal end 884 of the blade 880 and the walls of the distal sheath tip 901 to enable tissue to be drawn therein by the suction (represented by arrows "S") applied to the area between the inner wall of the outer sheath 900 and the neck 882 of the blade 800. It will also be appreciated that the blade 880 may be rotated in a counter clockwise or clockwise direction or be selectively oscillated between such rotational directions and still effectively cut tissue drawn therein. FIG. 34A depicts an alternative sheath tip embodiment 901' that is fabricated from a metal material such as, for example, stainless steel that has a series of serrated cutting teeth 905' formed on each cutting edge 890', 892'.

Figure 35:
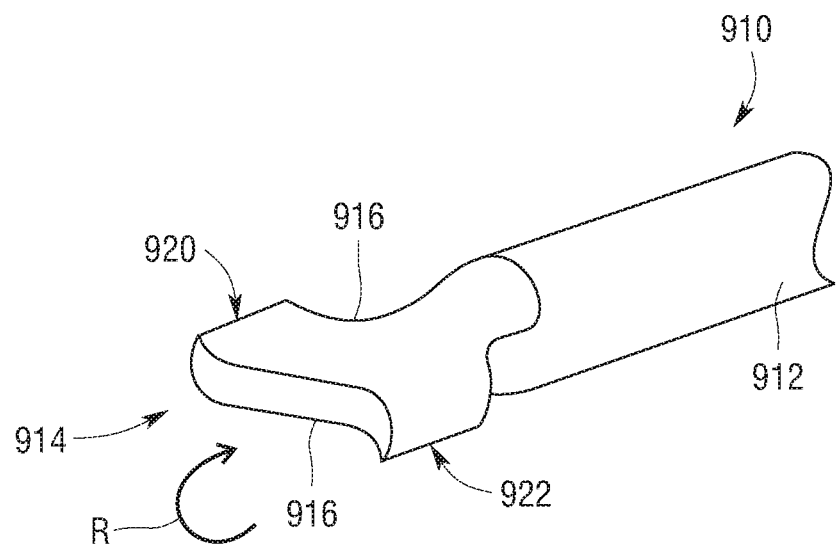
FIG. 35 is a perspective view of a portion of another non-limiting blade embodiment.

FIG. 35 depicts another blade embodiment 910 that may be substantially the same as blade 200 except for the differences noted below. In particular, the blade 910 may include a waveguide or proximal portion 912 that that terminates in a distal tissue cutting portion 914. The proximal portion 912 of the blade 910 may be configured to be threadably or otherwise attached to an ultrasonic horn of any of the various embodiments discussed above. The distal tissue cutting portion 914 may have opposed channels 916 formed therein that cooperate to define a first cutting edge 920 and a second cutting edge 922. This blade embodiment may be used in connection with any of the various outer sheath configurations described above and is designed to only rotate in a single direction "R" for tissue cutting purposes. As with the above-described embodiment, the arcuate channels 916 define openings between the tissue cutting portion 914 of the blade 910 and the inner walls of the distal sheath tip to enable tissue to be drawn therein as suction is applied to the area between the proximal portion 912 an the inner wall of the outer sheath.

Figure 36:
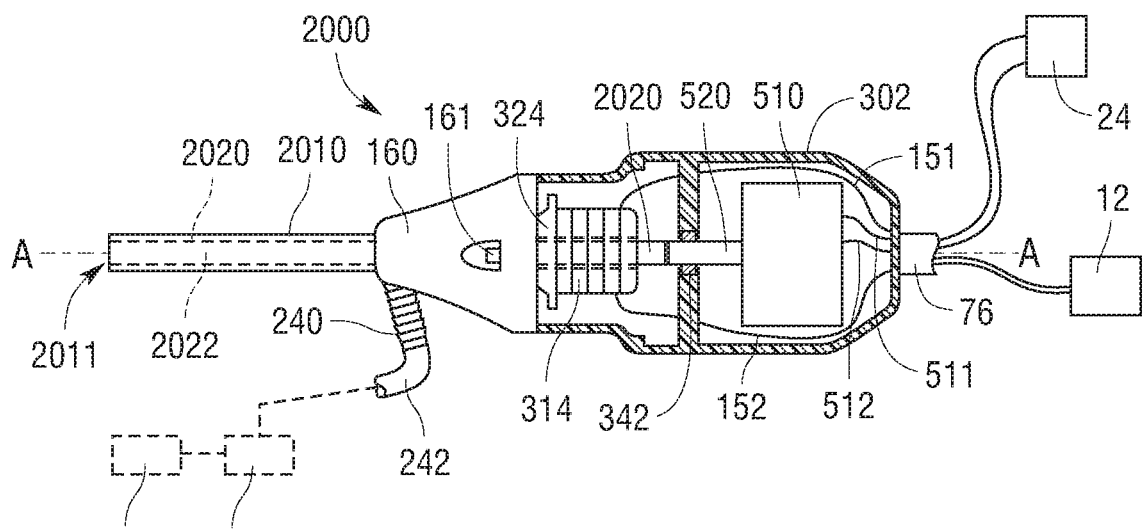
FIG. 36 is a partial cross-sectional view of another non-limiting ultrasonic surgical instrument embodiment.

FIG. 36 illustrates another surgical instrument 2000 wherein like numbers previously used to describe the various embodiments discussed above are used to designate like components. In these embodiments, the surgical instrument 2000 includes a housing 302 that houses an ultrasonic transducer assembly 314 that is attached to an ultrasonic horn 324. In this embodiment, the ultrasonic transducer assembly 314 and the ultrasonic horn 324 may be non-rotatably supported within the housing 302 in a known manner. Electrical control signals may be supplied to the ultrasonic transducer assembly 314 from an ultrasonic generator 12 by conductors 151, 152. Activation of the ultrasonic generator 12 will cause the ultrasonic transducer assembly 314 to apply ultrasonic motion to the ultrasonic horn 324. In this embodiment, a hollow outer sheath 2010 is coupled to the ultrasonic horn 324 for receiving ultrasonic motion therefrom. For example, in various embodiments, the outer sheath 2010 may be coupled to the ultrasonic horn 324 by a threaded connection or other suitable fastening arrangement.

This embodiment includes a rotatable blade 2020 that is rotatably supported within the outer sheath 2010 and is coupled to a motor 510 supported within the housing 302. The motor 510 may, for example, comprise a stepper motor of the type and construction described above. The motor 510 may have an encoder associated therewith that communicates with a control module 24 (FIG. 1) as was described above. The blade 2020 may have a hollow distal portion 2022 and a solid proximal portion 2024. See FIG. 36A. The solid proximal portion 2024 may be attached to the motor drive shaft 520 by a threaded or other suitable connection. The motor drive shaft 520 may be rotatably supported within the housing 302 by a proximal bearing 342. When control signals are supplied to the motor 510, the drive shaft 520 rotates about axis A-A which also causes the blade 2020 to rotate about axis A-A within the outer sheath 2010.

Figure 36A:
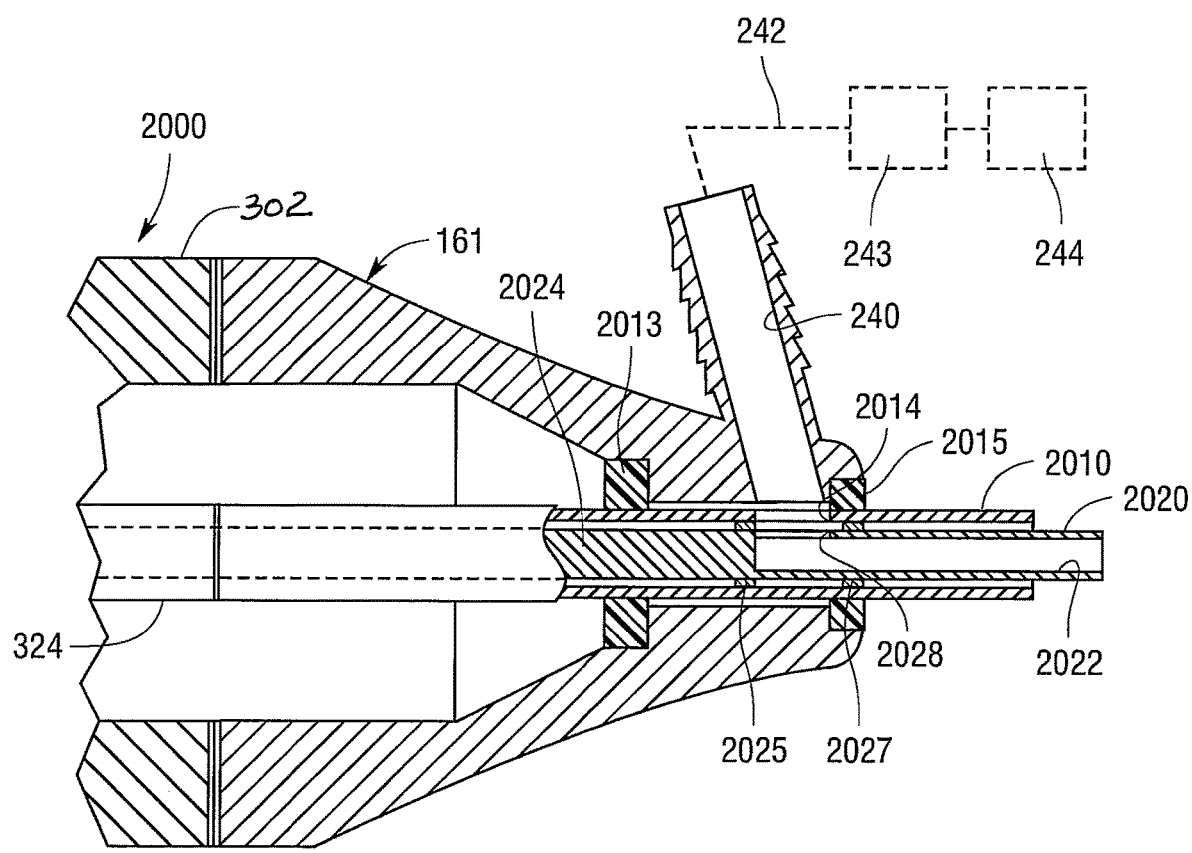
FIG. 36A is a partial cross-sectional view of a nosepiece portion of another non-limiting surgical instrument embodiment of the present invention.

As can be further seen in FIG. 36A, the hollow outer sheath 2010 is supported within a hollow nosepiece 160 that has a suction port 240 therein. A flexible tube 242 may be attached to the suction port 240 and communicate with a collection receptacle 243 that is coupled to a source of suction, generally depicted as 244. The hollow sheath 2010 may be supported within the nosepiece 160 by a proximal seal 2013 and a distal seal 2015 which are located on each side of the suction port 240 as shown in FIG. 36A and which serve to establish fluid tight seals therebetween. The hollow sheath 2010 is provided with at least one proximal sheath opening 2014 in registration with the suction port 240 between the proximal seal 2013 and the distal seal 2015. In addition, the hollow distal portion 2022 of the blade 2020 is rotatably supported within the hollow sheath 2010 by at least a proximal blade seal 2025 and a distal blade seal 2027. At least one blade discharge port 2028 may be provided through the hollow portion 2022 of the blade 2020 between the proximal blade seal 2025 and the distal blade seal 2027 to discharge into the at least one proximal sheath opening 2014.

Figure 37:
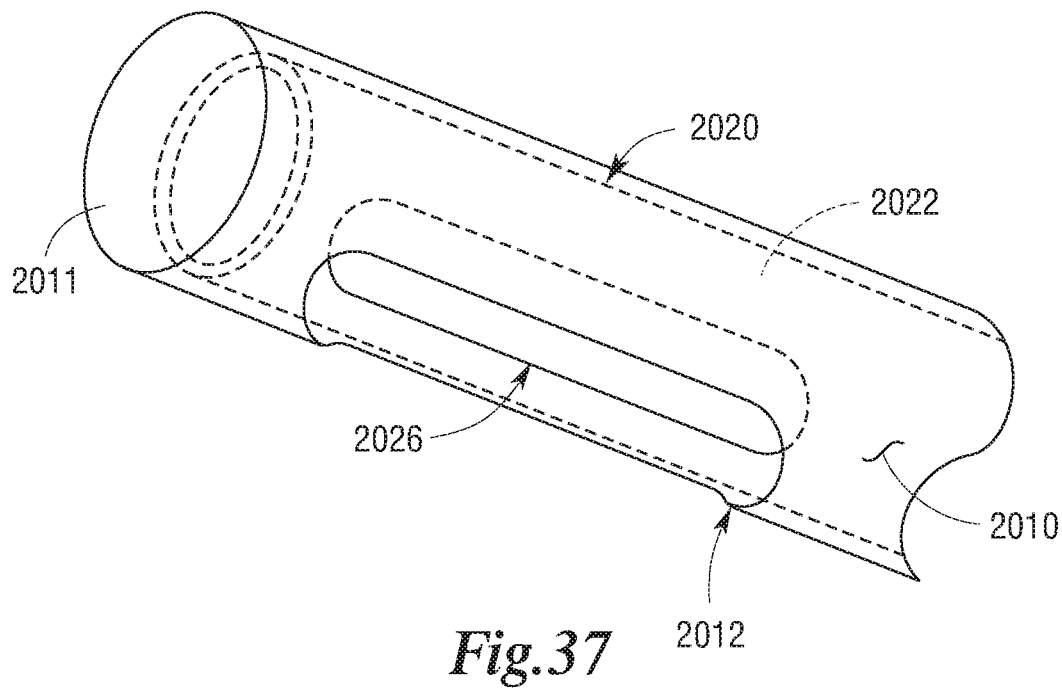
FIG. 37 is a partial perspective view of a distal end of the non-limiting outer sheath and blade arrangement of FIG. 36.
Figure 38:
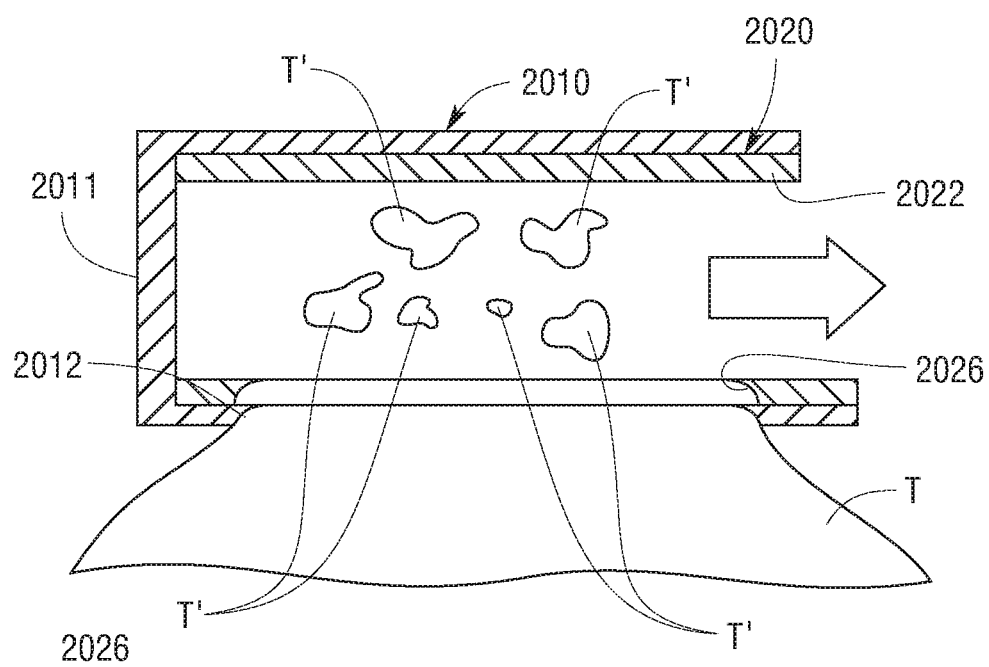
FIG. 38 is a cross-sectional view of distal portions of the outer sheath and blade embodiments depicted in FIG. 37 cutting tissue.

Also in various embodiments, a distal end portion 2011 of the hollow outer sheath is closed and at least one opening or window 2012 is provided therein to expose a distal tissue cutting portion 2025 of the blade 2020. In at least one embodiment window 2012 comprises an elongated slot and the distal tissue cutting portion also comprises an elongated slot 2026 in the blade 2020 (FIGS. 37 and 38). Thus, suction may be applied from the suction source 244 into the hollow portion of blade 2020 through the port 240, the proximal sheath opening 2014 and the blade discharge port 2028. As the distal openings 2026, 2012 coincide, tissue "T" may be drawn into the hollow distal portion 2022 of blade 2020 as shown in FIG. 38. The severed portions of tissue "T" may pass through the hollow distal portion 2022 of blade 2020 and out through openings 2028, 2014 and into the collection receptacle 243.

In use, the clinician may activate the rotating blade 2020 to cut and evacuate tissue. When a bleeder is encountered, the clinician may activate the ultrasonic transducer assembly 314 to send ultrasonic motions to the outer sheath 2010 for coagulation purposes. For example, spinal fusion surgeries require the removal of disc material due to a variety of disease states. Often times this material is toughened and requires quite a bit of force with conventional instrumentation to break up the disc and remove its fragments. Once the disc material is removed, the end plates must be scraped to reveal fresh surfaces to promote fusion of the plates to the cage. The plates must also be shaped to provide a good fit with the type of cage being used. Conventional instrumentation generally requires high forces from the surgeon very close to critical structures. In other embodiments, the motor may be coupled to rotate the ultrasonic transducer assembly and the blade may be attached to the ultrasonic transducer assembly as was described above so that the blade rotates and may have ultrasonic motion applied thereto.

Figure 44:
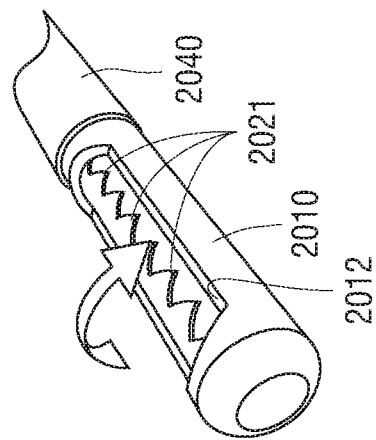
FIG. 44 is another partial perspective view of the retractable safety sheath embodiment illustrated in FIGS. 41-43 with the safety sheath retracted to an open position.
Figure 43:
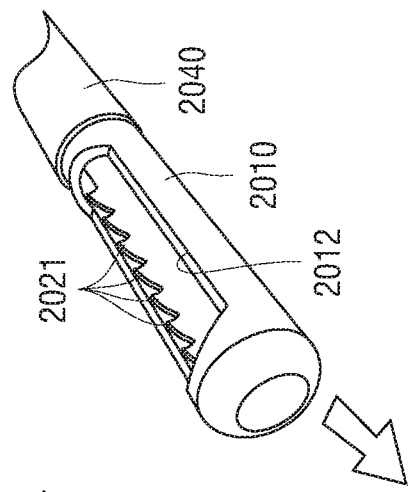
FIG. 43 is another partial perspective view of the retractable safety sheath embodiment illustrated in FIGS. 41 and 42 with the safety sheath retracted to an open position.
Figure 42:
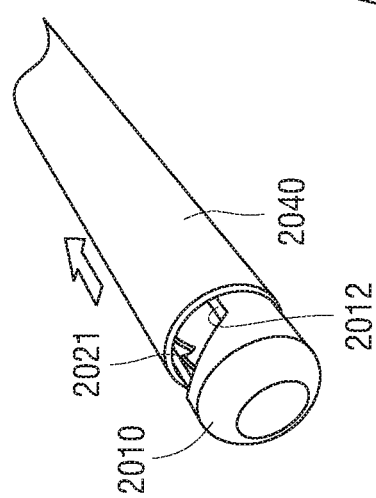
FIG. 42 is a partial perspective view of the retractable safety sheath embodiment illustrated in FIG. 41 starting to be retracted from a closed position.
Figure 45:
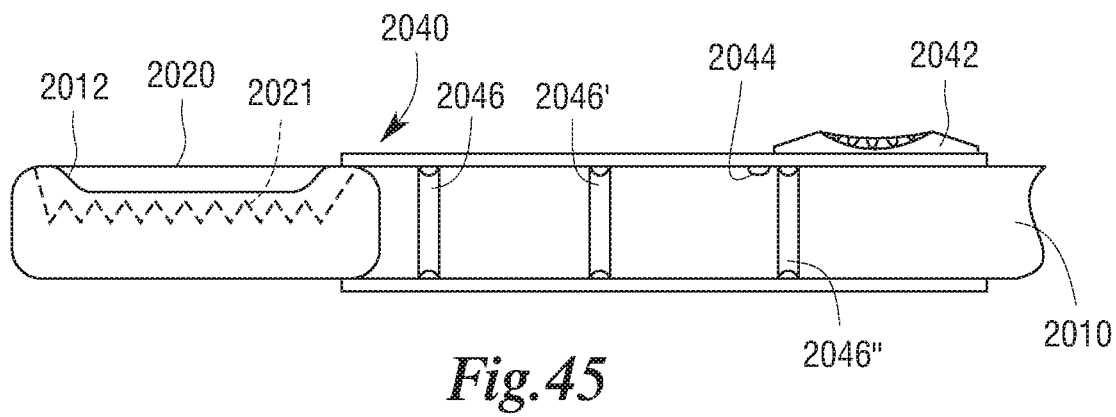
FIG. 45 is a side elevational view of a portion of the outer sheath and safety sheath embodiments illustrated in FIGS. 41-44 with the safety sheath shown in cross-section in an open position.
Figure 46:
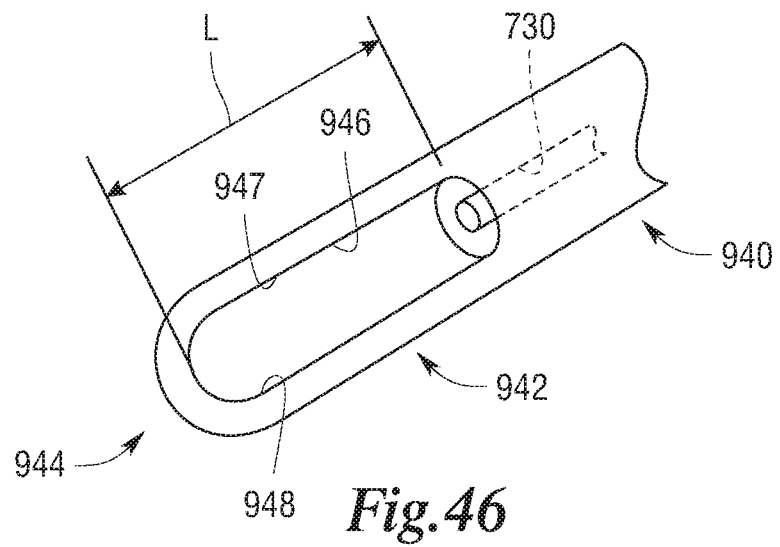
FIG. 46 is a perspective view of a portion of another non-limiting blade embodiment.

Use of the above-described surgical instrument 2000 may be particularly advantageous when performing, for example, a discectomy as shown in FIGS. 39 and 40. As can be seen in those drawings, the outer sheath 2010 may be inserted into the disc "D". The rotating blade 2020 may be used to shave off small pieces of disc and suction them out. Such arrangement eliminates the need for repeated insertion/removal of surgical tools. The device may also be employed to prepare the vertebrae endplates. In the embodiment depicted in FIGS. 41-45, the rotatable cutting blade 2020 has a series of serrated teeth 2021 formed on at least one side of the distal opening 2026 to further assist with the cutting of tissue drawn in through the opening 2012 in the outer sheath 2010. Also in this embodiment, a retractable safety shield 2040 is movably mounted on the outer sheath 2010 and is selectively movable from a closed position substantially covering the opening 2012 in the outer sheath 2010 to an open position exposing the opening 2012 (FIGS. 43 and 44). Such arrangement covers the teeth 2021 on the blade 2020 during insertion and removal of the outer sheath 2010 adjacent vital nerves and other critical tissues. To facilitate movement of the safety sheath 2040 on the outer sheath 2010, a thumb control tab 2042 (FIGS. 41 and 45) may be formed on the proximal end of the safety sheath 2040 to enable the clinician to apply sliding actuation forces thereto. In addition, in various embodiments, a retainer protrusion 2044 may be formed on the safety sheath 2040 to engage at least one detent or groove 2046 provided in the outer sheath 2010 to retain the safety sheath 2040 in a corresponding open or closed position. For example, one detent or groove 2046 may correspond to a closed position (wherein the safety sheath 2040 covers the opening 2012) and another detent or groove 2046' may correspond to a partially opened position (wherein a portion of the opening 2012 is exposed) and another detent or groove 2046" may correspond to a fully opened position (wherein the opening 2012 is fully exposed).

Figure 47:
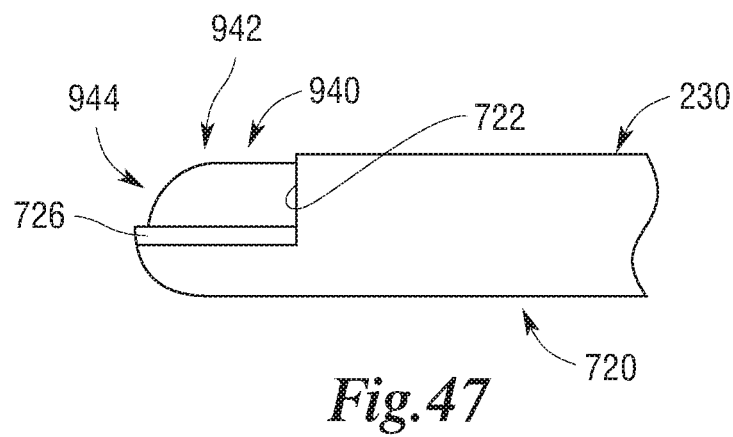
FIG. 47 is a side view of a portion of another hollow outer sheath and blade arrangement of another non-limiting embodiment.

FIGS. 46-51 illustrate a blade 940 that has a nearly straight distal tissue cutting portion 942. Such blade configuration may reduce potential impedance and power increases when the blade 940 is used in an aqueous environment when compared to the impedance and power requirements of various other blade configurations when used in that environment. That is, such relatively straighter blade designs may require less power to operate in an aqueous environment. The blade 940 may have a round or blunted distal end 944 and a groove 946 that forms cutting edges 947, 948 for cutting tissue when the blade 940 is used in connection with an outer sheath 230 as described above. The groove may have a length "L" of, for example, one (1) inch. The blade 942 may also have a suction passage 730 of the type and construction described above. As shown in FIG. 47, a low friction fender or pad 726 of the type and construction described above may be employed around the exposed distal end portion 720 of the outer sheath 230. FIGS. 48-51 depict alternative cross-sectional shapes of a blade 940 where differently shaped grooves 946 are employed.

Figure 53:
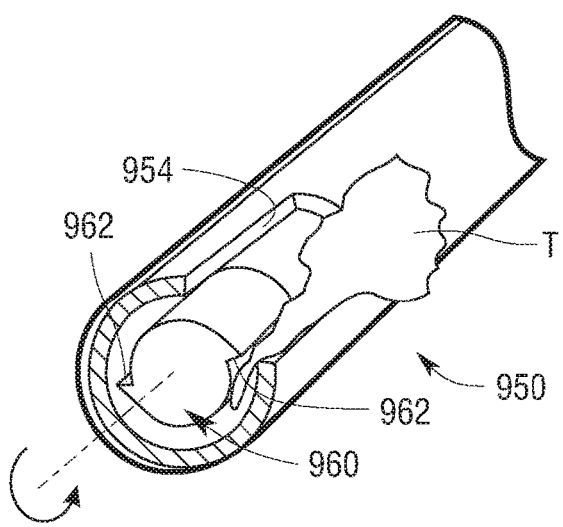
FIG. 53 is another partial cross-sectional view of the outer sheath and blade embodiment of FIG. 52 interacting with body tissue.
Figure 54:
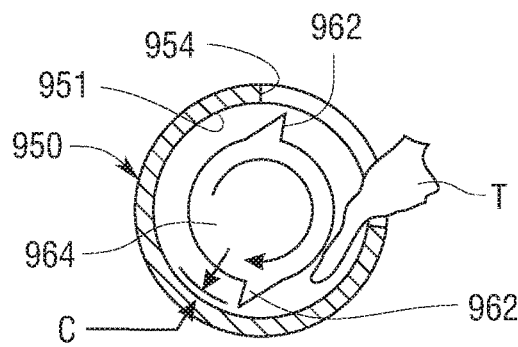
FIG. 54 is an end cross-sectional view of the outer sheath and blade arrangement depicted in FIGS. 52 and 53 interacting with body tissue.
Figure 55:
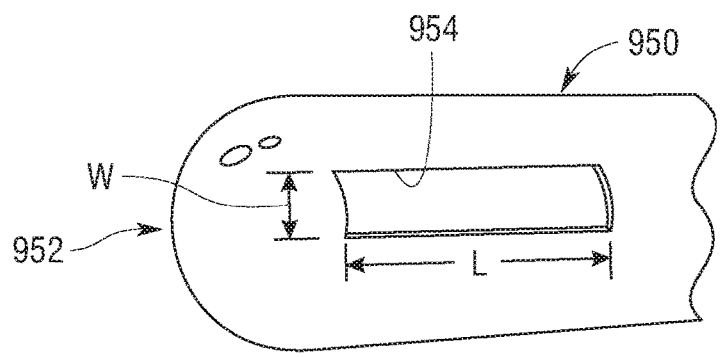
FIG. 55 is a partial perspective view of another non-limiting outer sheath embodiment.

FIGS. 52-55 depict another non-limiting blade and sheath embodiment. This embodiment employs a hollow outer sheath 950 that may be attached to the nosepiece or the ultrasonic transducer assembly of any of the surgical instruments described above by any suitable fastening method or connection arrangement. As can be seen in FIG. 55, the outer sheath 950 has a closed rounded or blunted nose portion 952 and an elongated rectangular-shaped window or opening 954. In one embodiment, for example, the rectangular-shaped window 954 has a width "W" that is approximately one-fourth of the circumference of the hollow outer sheath 950 and a length of approximately 0.25 inches. The sheath 950 may be fabricated from, for example, stainless steel.

Figure 52:
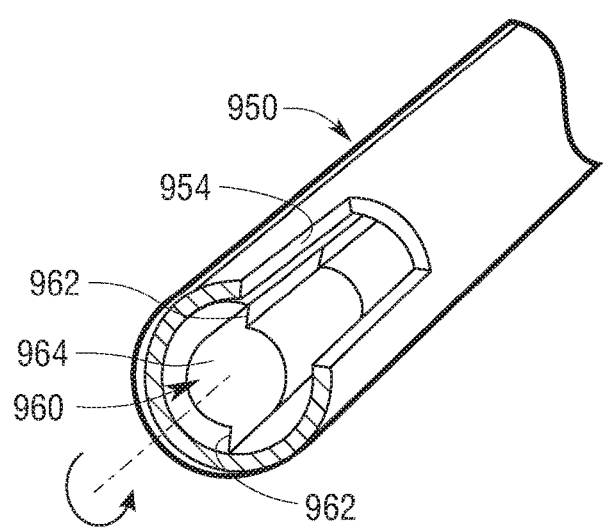
FIG. 52 is a partial cross-sectional view of another non-limiting outer sheath and blade embodiment.

This embodiment also employs a blade 960 that can be used in connection with any of the surgical instrument embodiments described above or others. For example, a waveguide or proximal portion of the blade may be configured for attachment to the instrument's ultrasonic horn or motor drive shaft by a threaded or other connection. As can be seen in FIGS. 52-54, the blade 960 has a pair of radially-opposed sharpened cutting edges 962 formed thereon that serve to cut tissue "T" that is drawn into the window 954 of the outer sheath 950. In various embodiments, the blade 960 may be fabricated from, for example, Titanium and be sized relative to the outer sheath 950 such that a clearance "C" is provided between the inner wall 951 of the outer sheath 950 and the tips of the radially opposed sharpened cutting edges 962. See FIG. 54. In some embodiments, for example, the clearance "C" may be approximately 0.001 inches. In this embodiment, the blade 960 may be fabricated from, for example, Titanium and have a flattened distal end 964. In use, when gross rotary motion is applied to the blade 960 in any of the various manners described above and suction is applied within the hollow outer sheath 950, the tissue "T" is drawn in through the window 954 and trapped between the blade 960 and the inner wall 951 of the outer sheath 950. This action isolates the tissue "T" long enough to cut when, for example, the device is employed in an aqueous environment as will be discussed in further detail below. In some embodiments, the cutting edges 962 may be serrated. In other embodiments the cutting edges 962 are not serrated.

Figure 56:
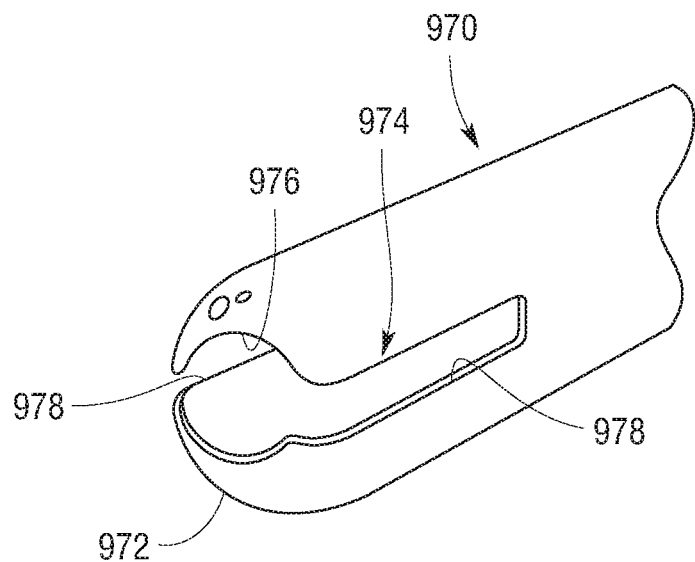
FIG. 56 is a partial perspective view of another non-limiting outer sheath embodiment.
Figure 57:
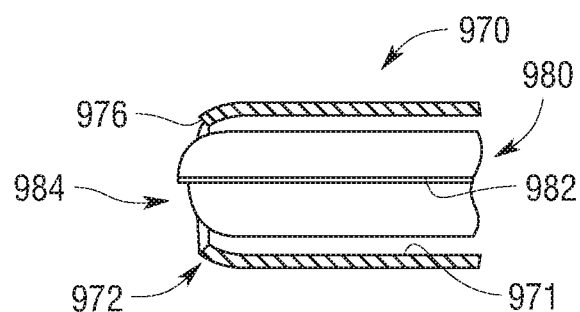
FIG. 57 is a partial cross-sectional view of the outer sheath embodiment of FIG. 56 supporting another non-limiting blade embodiment.

FIG. 57 depicts another non-limiting blade and sheath embodiment. This embodiment employs a hollow outer sheath 970 that may be attached to the nosepiece or ultrasonic transducer assembly of any of the various instruments described above. As can be seen in FIG. 56, the outer sheath 970 has a rounded or blunted nose portion 972 and an elongated window or opening 974 that forms a blade access hole 976 in the nose portion 972 and two radially-opposed lateral window portions 978. In one embodiment, for example, wherein the outer diameter of the outer sheath 970 is approximately 0.157 inches, the diameter of the blade access hole 976 may be approximately 0.125 inches. The lateral window portions 978 may each have a width "W" of approximately 0.090 inches and a length "L" of approximately 0.25 inches. Other window sizes/configurations may be employed. The sheath 970 may be fabricated from, for example, stainless steel.

This embodiment also employs a blade 980 that has a waveguide or proximal portion that is configured for attachment to the ultrasonic horn or motor drive shaft of any of the various surgical instrument embodiments described above 324 by a threaded or other suitable connection. In various embodiments, the blade 980 may be substantially the same as blade 960 described above (with radially-opposed sharpened cutting edges 982), except that blade 980 has a rounded/substantially blunted distal tip portion 984 that protrudes out through the blade access hole 976 in the outer sheath 970. See FIG. 57. In various embodiments, the blade 980 may be fabricated from, for example, Titanium and be sized relative to the outer sheath 970 such that a clearance is provided between the inner wall 971 of the outer sheath 970 and the tips of the radially opposed sharpened cutting edges 962. In some embodiments, for example, the clearance may be approximately 0.001 inches. In use, when gross rotary motion is applied to the blade 980 in any of the various manners described above and suction is applied within the hollow outer sheath 970, the tissue is drawn in through the window portions 978 and trapped between the blade 980 and the inner wall 971 of the outer sheath 970. This action isolates the tissue long enough to cut when, for example, the device is employed in an aqueous environment as will be discussed in further detail below. Also, in this embodiment, when the blade 980 is ultrasonically powered, the clinician can use the exposed distal tip portion 984 for spot ablation of fibrous tissue or for spot coagulation purposes. In some embodiments, the cutting edges 982 may be serrated. In other embodiments the cutting edges 982 are not serrated.

Figure 58:
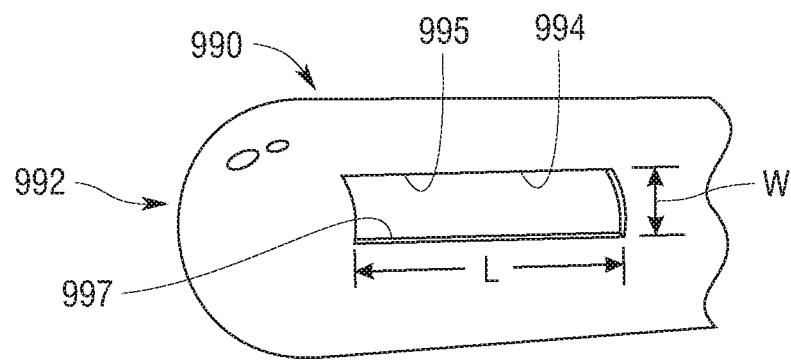
FIG. 58 is a partial perspective view of another non-limiting outer sheath embodiment.
Figure 59:
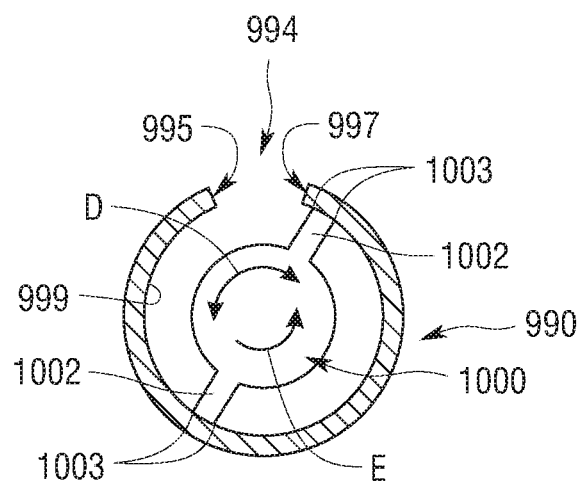
FIG. 59 is a cross-sectional view of another non-limiting outer sheath and blade embodiment.
Figure 60:
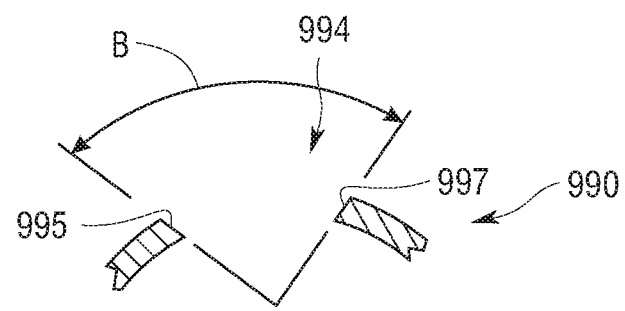
FIG. 60 illustrates an angle between the cutting edges formed on a non-limiting outer sheath embodiment.

FIG. 59 depicts another non-limiting blade and sheath embodiment. This embodiment employs a hollow outer sheath 990 that may be attached to the nosepiece or ultrasonic transducer assembly of any of the above-described surgical instruments by any suitable fastening method or connection arrangement. As can be seen in FIG. 58, the outer sheath 990 has a closed rounded or blunted nose portion 992 and an elongated rectangular-shaped window or opening 994. In one embodiment, for example, the rectangular-shaped window 994 has a width "W" that is approximately 0.100 inches and a length of approximately 0.25 inches. The sheath 990 may be fabricated from, for example, a polyamide or similar material that does not result in the heating of a blade 1000 from contact therewith. The window 994 may be defined by sharp edges 995, 997. As can be seen in FIG. 60, edges 995, 997 may be provided with an angle "B" therebetween. In some embodiments, angle "B" may be approximately 110 degrees.

These embodiments also employ a blade 1000 that has a waveguide or proximal portion that is configured for attachment to the ultrasonic horn or motor drive shaft of any of the above-described surgical instruments or others by a threaded or other suitable connection arrangement. As can be seen in FIG. 59, the blade 1000 may have a pair of radially-opposed sharpened cutting portions 1002 formed thereon that serve to cut tissue that is drawn into the window 994 in the outer sheath 990. In various embodiments, the blade 1000 may be fabricated from, for example, Titanium. The cutting portions 1002 of the blade 1000 may have sharp cutting corners 1003 formed thereon. In some embodiments, the cutting corners 1003 may be serrated. In other embodiments the cutting corners 1003 are not serrated. The cutting portions 1002 may be sized relative to the outer sheath 990 to establish a tissue shearing action between the cutting corners 1003 and the sharp edges 995, 996 of the window opening 994 as the blade 1000 is rotated or oscillated back and forth within the outer sheath 990. The blade 1000 may be sized relative to the outer sheath 990 to create a slip fit therebetween that otherwise prevents tissue from becoming trapped between those two components. The blade 990 could rotate back and forth (arrow "D") or rotate in a single direction (arrow "E") and if desire be ultrasonically activated as well as was discussed above. See FIG. 59. In use, when gross rotary motion is applied to the blade 1000 in any of the various manners described above and suction is applied within the hollow outer sheath 990, the tissue "T" is drawn in through the window 994 and trapped between the blade 1000 and the inner wall 999 of the outer sheath 990. This action isolates the tissue long enough to cut when, for example, the device is employed in an aqueous environment as will be discussed in further detail below.

Figure 61:
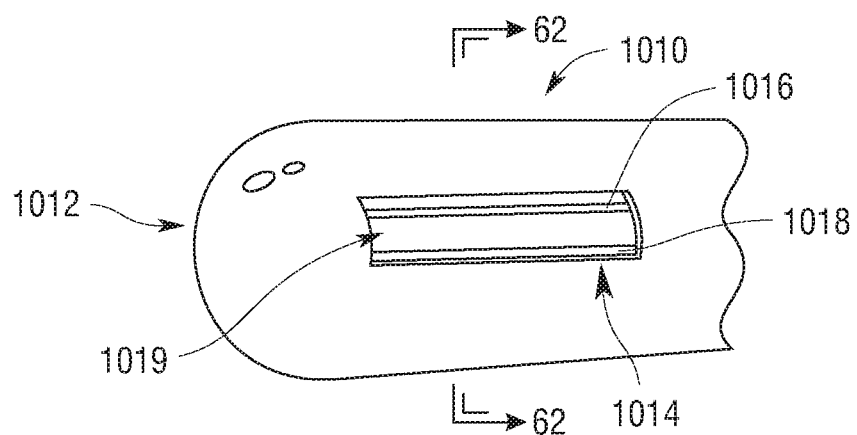
FIG. 61 is a perspective view of another non-limiting outer sheath embodiment.
Figure 62:
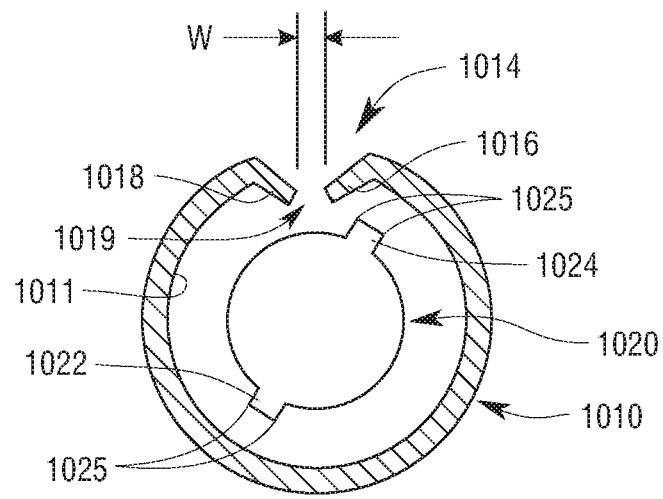
FIG. 62 is a cross-sectional view of the outer sheath and blade embodiment of FIG. 61.

FIG. 62 depicts another non-limiting blade and sheath embodiment. This embodiment employs a hollow outer sheath 1010 that may be attached to the nosepiece or ultrasonic transducer assembly of any of the above described surgical instruments by any suitable fastening method or connection arrangement. As can be seen in FIG. 61, the outer sheath 1010 may have a closed rounded or blunted nose portion 1012 and an elongated rectangular-shaped window or opening 1014. In one embodiment, for example, the window 1014 has a first coined or depressed edge 1016 and a second coined or depressed edge 1018 to define an opening 1019 that may have a width W" that is approximately 0.100 inches. Window 1014 may have a length of approximately 0.25 inches. The sheath 1010 may be fabricated from, for example, stainless steel These embodiments also employ a blade 1020 that has a waveguide or proximal portion that is configured for attachment to the ultrasonic horn or motor drive shaft of any of the above-described surgical instruments or others by a threaded or other suitable connection. As can be seen in FIG. 62, the blade 1020 may have a pair of radially-opposed sharpened cutting portions 1022, 1024 formed thereon. The blade 1020 may be fabricated from, for example, Titanium and have relative sharp cutting corners 1025 formed on each cutting portions 1022, 1024. In some embodiments, the cutting corners 1025 may be serrated. In other embodiments the cutting corners 1025 are not serrated. The cutting portions 1022, 1024 may be sized relative to the outer sheath 1010 to establish a tissue shearing action between the depressed edges 1016, 1018 and the cutting corners 1025 as the blade 1020 is rotated or oscillated within the outer sheath 1010. Such arrangement forms a relatively small localized area to lessen contact issues between the blade and the outer sheath by also facilitates a scissoring effect on the tissue. In use, when gross rotary motion is applied to the blade 1020 in any of the various manners described above and suction is applied within the hollow outer sheath 1010, the tissue is drawn in through the opening 1019 and trapped between the blade 1020 and the inner wall 1011 of the outer sheath 1010. This action isolates the tissue long enough to cut when, for example, the device is employed in an aqueous environment as will be discussed in further detail below.

Figure 63:
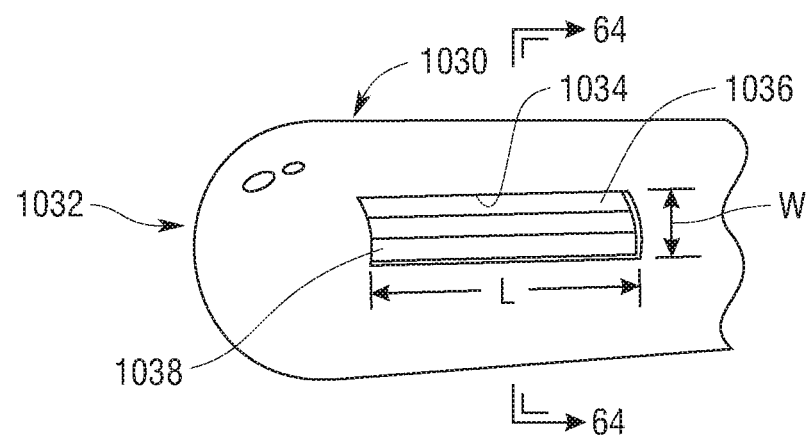
FIG. 63 is a perspective view of another non-limiting outer sheath embodiment.
Figure 64:
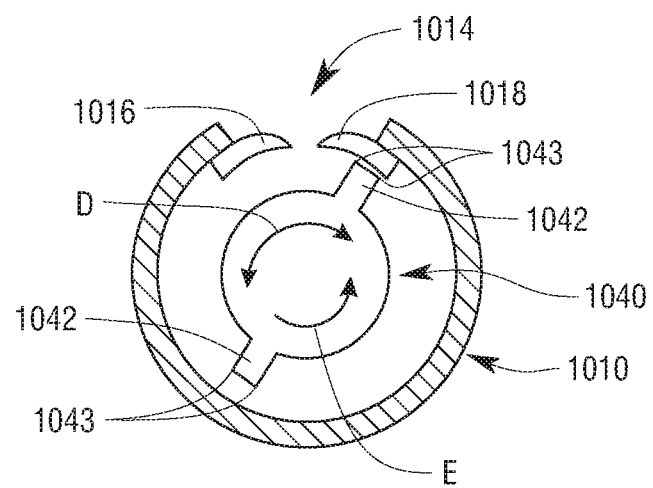
FIG. 64 is a cross-sectional view of the outer sheath and blade embodiment of FIG. 63.

FIG. 64 depicts another non-limiting blade and sheath embodiment. This embodiment employs a hollow outer sheath 1030 that may be attached to the nosepiece or ultrasonic transducer assembly of any of the above-described surgical instruments. As can be seen in FIG. 63, the outer sheath 1030 may have a closed rounded or blunted nose portion 1032 and an elongated rectangular-shaped window or opening 1034. This embodiment may further include a pair of sharpened cutting inserts 1036, 1038. The cutting inserts 1036, 1038 may be fabricated from, for example, hardened stainless steel and be attached within the hollow sheath 1030 by, for example, welding. Window 1034 may have a width W" that is approximately 0.100 inches and a length of approximately 0.25 inches. The sheath 1030 may be fabricated from, for example, stainless steel.

These embodiments also employ a blade 1040 that has a waveguide or proximal portion that is configured for attachment to the ultrasonic horn or motor drive shaft of any of the surgical instruments described herein or others by a threaded or other suitable connection. As can be seen in FIG. 64, the blade 1040 has a pair of radially-opposed cutting portions 1042 formed thereon that have relatively sharp cutting corners 1043. In some embodiments, the cutting corners 1043 may be serrated. In other embodiments the cutting corners 1043 are not serrated. In various embodiments, the blade 1040 may be fabricated from, for example, Titanium and be sized relative to the cutting inserts 1036, 1038 to establish a tissue shearing action between the sharp cutting corners 1043 and the cutting portions 1042 as the blade 1020 is rotated or oscillated within the hollow outer sheath 1030. The outer diameter of the blade 1020 is smaller than the inner diameter of the outer sheath 1030 to provide clearance for the blade 1040 during operation. The only instance of contact would be between the cutting portions 1042 of the blade 1040 and the inserts 1036, 1038 along the window opening 1034 wherein the tissue is pulled in by the suction.

Figure 65:
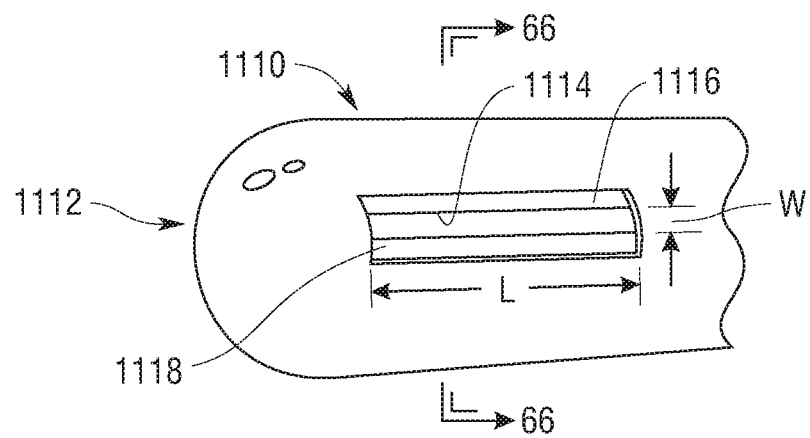
FIG. 65 is a perspective view of another non-limiting outer sheath embodiment.
Figure 66:
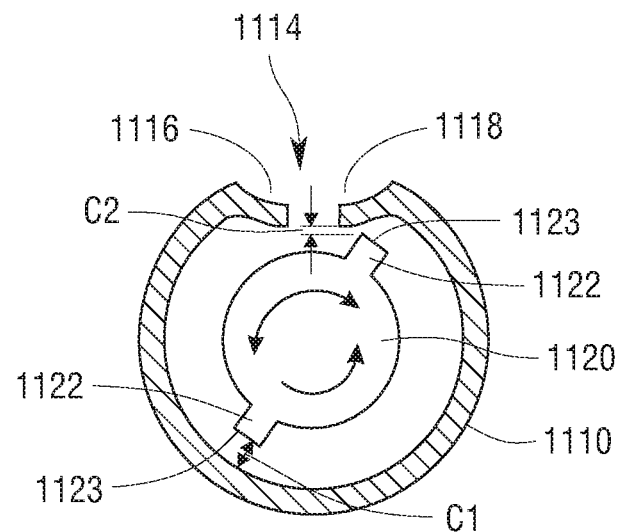
FIG. 66 is a cross-sectional view of the outer sheath and blade embodiment of FIG. 65.

FIG. 66 depicts another non-limiting blade and sheath embodiment. This embodiment employs a hollow outer sheath 1110 that may be attached to the nosepiece or ultrasonic transducer assembly of any of the surgical instruments described above by any suitable fastening method or connection arrangement. As can be seen in FIG. 65, the outer sheath 1110 may have a closed rounded or blunted nose portion 1112 and an elongated rectangular-shaped window or opening 1114. In this embodiment, the lateral edge portions 1116, 1118 of the window 1114 are coined or depressed inward. Window 1014 may have a width W" that is approximately 0.10 inches and a length of approximately 0.25 inches.

These embodiments also employ a blade 1120 that has a waveguide or proximal portion that is configured for attachment to the ultrasonic horn or motor drive shaft of any of the surgical instrument embodiments described above or others by a threaded or other suitable connection arrangement. As can be seen in FIG. 66, the blade 1120 has a pair of radially-opposed cutting portions 1122 formed thereon that have relatively sharp cutting corners 1023. In some embodiments, the cutting corners 1023 may be serrated. In other embodiments the cutting corners 1023 are not serrated. In various embodiments, the blade 1020 may be fabricated from, for example, Titanium and be sized relative to the depressed edges 1116, 1118 to establish a tissue shearing action between the sharp cutting corners 1023 and the cutting portions 1122 as the blade 1120 is rotated or oscillated. Such arrangement defines a larger clearance C1 between the cutting portions 1122 of the blade 1120 and the inner wall 1111 of the sheath 1110. To form a tissue shearing action between the lateral edges 1116, 1118 and the cutting portions 1122, a clearance C2 that is less than C1 is provided.

Figure 67:
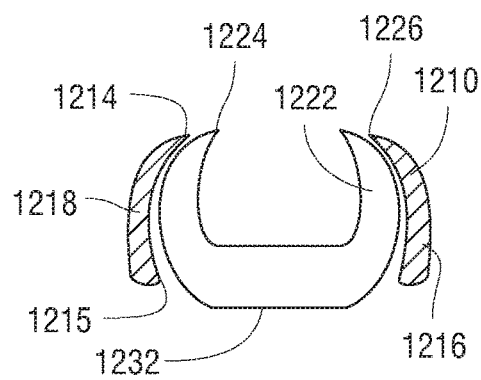
FIG. 67 is a cross-sectional end view of another non-limiting outer sheath and blade arrangement.
Figure 68:
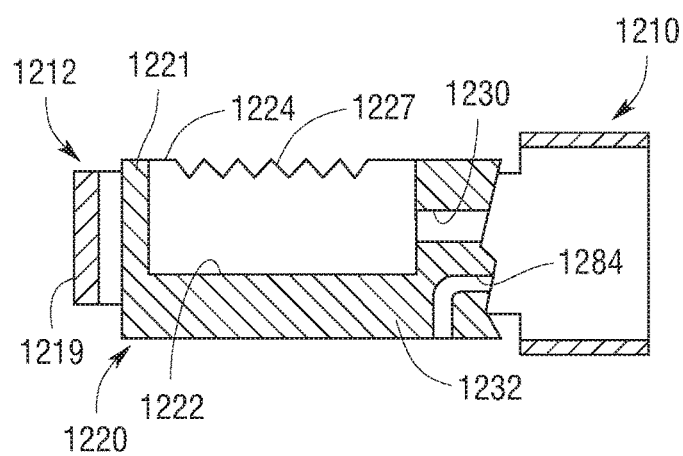
FIG. 68 is a partial side cross-sectional view of the outer sheath and blade arrangement of FIG. 67.
Figure 69:
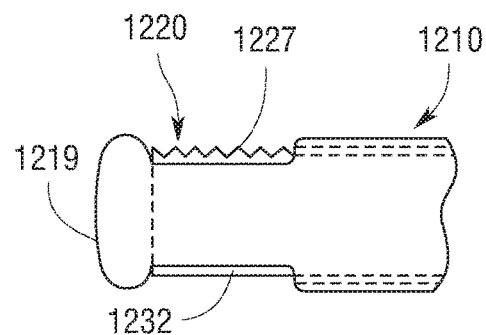
FIG. 69 is a partial side view of a distal end portion of the outer sheath and blade arrangement of FIGS. 67 and 68.

FIGS. 67-69 depict another non-limiting blade and sheath embodiment. This embodiment employs a hollow outer sheath 1210 that may be attached to the nosepiece or ultrasonic transducer assembly of any of the surgical instruments described above. The hollow outer sheath 1210 has a distal nose portion 1212 that includes an upper opening 1214 and a lower opening 1215 that serve to define arcuate lateral side portions 1216, 1218. The distal nose portion 1212 may further have a closed end 1219 that extends between the lateral side portions 1216, 1218.

This embodiment further comprises a blade 1220 that has a waveguide or proximal portion that is configured for attachment to the ultrasonic transducer assembly of any of the surgical instruments described above. The blade 1220 further has a distal end portion 1221 that has a cavity 1222 that serves to define a pair of arcuate cutting portions 1224, 1226 that extend above the arcuate lateral side portions 1216, 1218 of the hollow sheath 1210. One, both or neither of the cutting portions 1224, 1226 may have serrated teeth 1227. In the embodiment depicted in FIG. 67, the cavity 1222 has a cross-sectional shape that roughly resembles a flat bottom "C". However, the cavity 1222 may have other cross-sectional shapes. At least one suction passage 1230 may be provided through the blade 1220 as shown. The suction passage may communicate with a source of suction (not shown).

In various embodiments, the blade 1220 may be fabricated from, for example, Titanium and be sized relative to the distal nose portion 1212 of the hollow sheath 1210 such that the bottom portion 1232 of the blade 1220 extends downward beyond the lateral sides 1216, 1218 of the nose portion 1212. Likewise, the cutting edges of the arcuate side portions 1224, 1226 extend above the lateral sides 1216, 1218 as shown in FIG. 67. The exposed bottom portion 1232 of the blade 1220 may be used, for example, to coagulate tissue, while the cutting edges 1224, 1226 may be used to cut and sever tissue.

Figure 70:
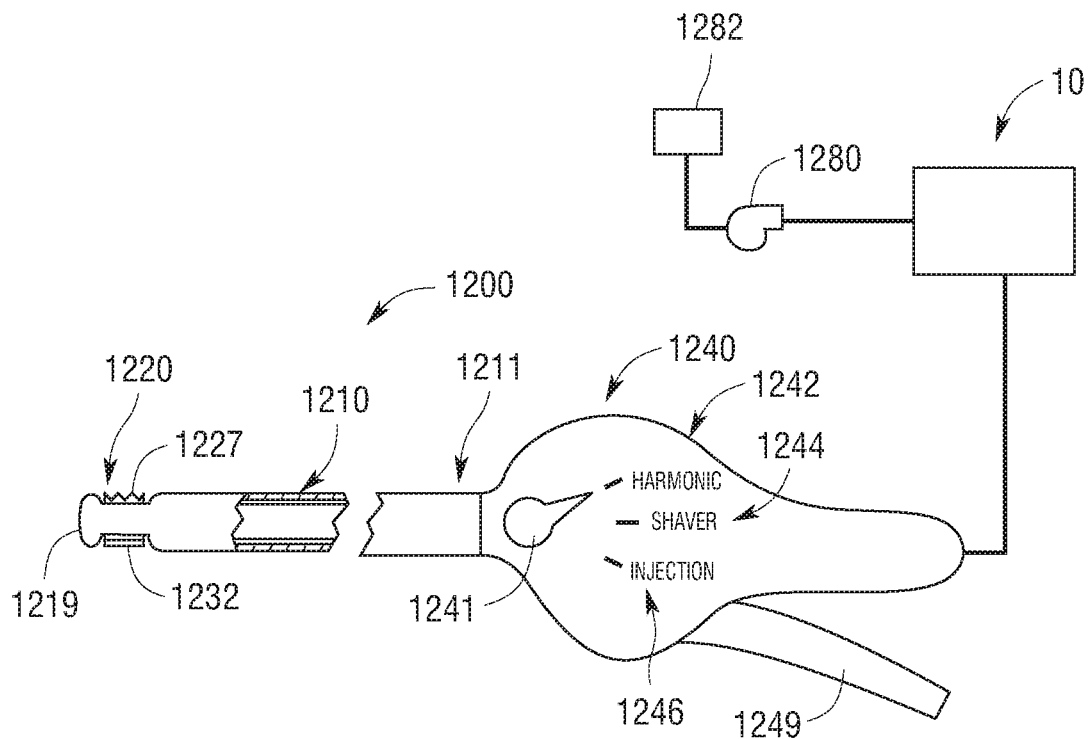
FIG. 70 is a side view of a non-limiting handpiece housing embodiment attached to the outer sheath and blade arrangement of FIGS. 67-69.
Figure 71:
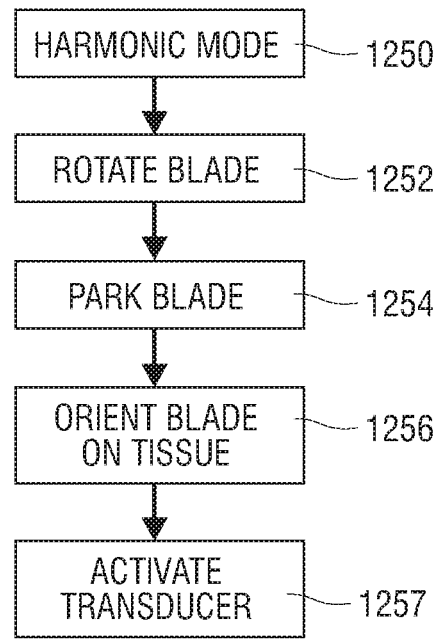
FIG. 71 depicts a method of using the surgical instrument embodiment of FIG. 70.

The proximal end 1211 of the hollow sheath 1210 protrudes from a handle housing 1240 as shown in FIG. 70. The handle housing 1240 houses an ultrasonic transducer assembly, a motor, and a slip ring assembly as was described above and is coupled to a control system 10. The handle housing 1240 may include a selector switch 1241 which enables the clinician to switch between a first "ultrasonic" mode 1242, a second "shaver" mode 1244, and a third "injection" mode 1246. The switching mechanism 1241 communicates with the control system 10 to automatically orient the blade 1220 in a desired rotational orientation. For example, to employ the device 1200 in the ultrasonic mode 1242, the clinician switches the selector switch 1241 to the ultrasonic mode position 1242 (depicted as action 1250 in FIG. 71). When in the first ultrasonic configuration 1242, the motor will rotate the blade 1220 to the position shown in FIGS. 67 and 68 (depicted as action 1252 in FIG. 71) and then park it in that position to expose the bottom portion 1232 of the blade 1220 through the hollow sheath 1210 (depicted as action 1254 in FIG. 71). When in that position, the ultrasonic transducer assembly is activated to enable the bottom portion 1232 to be used to achieve hemostasis (depicted as action 1257 in FIG. 71). More particularly, when in the ultrasonic mode 1242, the clinician may orient the bottom portion 1232 against the tissue that is bleeding and then apply firm pressure to the tissue (depicted as action 1256 in FIG. 71) with the exposed portion 1232 of the blade 1220. The clinician then activates the ultrasonic transducer assembly to achieve hemostasis (depicted as action 1258 in FIG. 71). In alternative embodiments, the device 1200 may be provided with a series of switches/buttons as was described above that communicate with a control system such that activation of one switch may initiate rotation. Activation of another switch may initiate rotatable oscillation and activation of another switch may, in cooperation with the control system rotate the blade to the ultrasonic position and park it and thereafter activate the ultrasonic transducer assembly or in still other embodiments, the ultrasonic transducer assembly may be activated by yet another separate switch. All of such alternative arrangements are within the scope of the various non-limiting embodiments disclosed herein and their respective equivalent structures.

Figure 72:
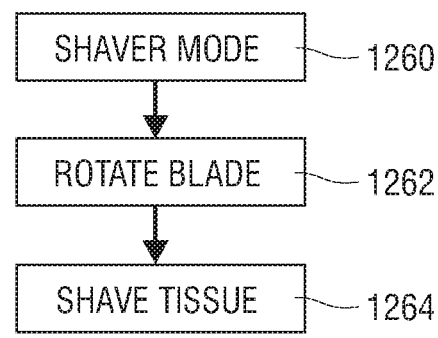
FIG. 72 depicts another method of using the surgical instrument embodiment of FIG. 70.

FIG. 72 illustrates use of the device 1200 when in the shaver mode 1244. In particular, the selector switch 1241 is moved to the shaver position 1242 (depicted as action 1260 in FIG. 72). When in that position, the motor continuously rotates the blade 1220 within the hollow outer sheath 1210 (depicted as action 1262 in FIG. 72). In other embodiments, the motor may rotatably oscillate the blade 1220 back and forth within the outer sheath 1210 or in other embodiments, the selector switch may be movable to yet another position wherein the rotatable oscillation is initiated. In either case, the clinician may then contact tissue with the rotating or oscillating blade (1220) to cause the tissue to be shaved and evacuated through the suction passage 1230 (depicted as action 1264 in FIG. 72).

Figure 73:
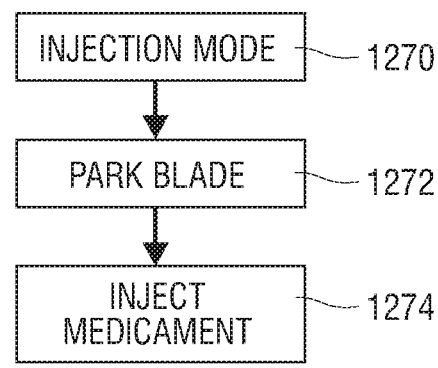
FIG. 73 depicts another method of using the surgical instrument embodiment of FIG. 70.

FIG. 73 illustrates use of the device 1200 when in the injection mode 1246. In particular, the selector switch 1241 is moved to the injection position 1246 (depicted as action 1270 in FIG. 73). When in that position, the blade 1220 is retained in a parked position (depicted as action 1272 in FIG. 73). The clinician may then orient the blade in a desired position and then inject the desired medicament (depicted as action 1274 in FIG. 73). One form of medicament that may be injected for example may comprise a cell generating drug sold under the trademark "Carticel". However, other drugs and medicaments could be employed. The injection action may be accomplished by orienting the blade 1220 to a position within the outer sheath 1210 such that a medicament passage 1284 extending through the blade 1220 is exposed through the outer sheath 1210 to enable medicament to be advantageously applied to the adjacent site. The medicament may then be injected by activating a pump 1280 that communicates with a source of the medicament 1282. See FIG. 70. In various embodiments, the device 1200 may have an injection trigger 1249 that communicates with the pump 1280 such that activation of the injection trigger 1249 will cause the pump 1280 to inject the medicament out through the passage 1284 (FIG. 68). In alternative embodiments, the medicament may be manually injected by, for example, a syringe into a port (not shown) that communicates with medicament passage 1284 in blade 1220.

FIGS. 74-77 depict another non-limiting surgical instrument embodiment 1300. The device 1300 may include any one of the handpiece devices 300, 400, 500 described above. For example, the device 1300 may include a handpiece 300 that incorporates the difference noted below. The handpiece 300 includes a blade 200 that has a waveguide or proximal portion that is coupled to an ultrasonic transducer assembly that, when activated, applies ultrasonic motion to the blade 200. The blade 200 may also be rotated by the motor arrangement contained within the handpiece 300 as described above. The blade 200 may extend through an inner sheath 1320 that protrudes from the handpiece 300. The blade 200 is free to be selectively vibrated and rotated within the inner sheath 1320. One or more seal members 1322 may be provided between the blade 200 and the inner sheath 1320 to prevent fluids and tissue from entering the area between the inner sheath 1320 and the blade 200. The seal members 1322 may be fabricated from, for example, silastic silicone.

Figures 76, 77:
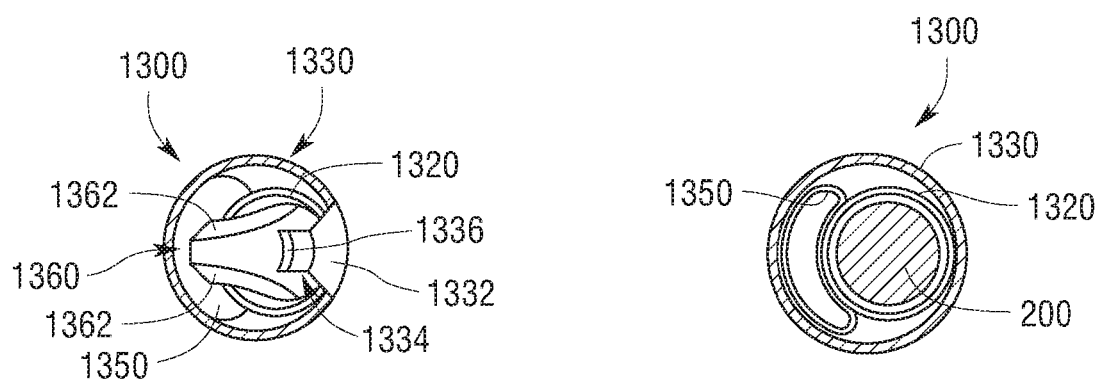
FIG. 76 is an end view of the outer sheath and blade arrangement of FIG. 75.
FIG. 77 is a cross-sectional end view of the sheath and blade arrangement of FIGS. 75 and 76.

The device 1300 may further include an outer sheath 1330 that is movably received on the inner sheath 1320. The outer sheath 1330 may be sized relative to the inner sheath 1320 such that a suction tube 1350 may extend between a portion of the inner sheath 1320 and a portion of the outer sheath 1330. The suction tube 1350 may communicate with a source of suction generally depicted as 1352. See FIG. 74. As can be seen in FIGS. 74-77, the outer sheath 1330 may include a swing arm portion 1332 that protrudes distally from a distal end portion 1331 of the outer sheath 1330. The swing arm 1332 may be relatively straight (FIG. 75) or it may have a slightly curved distal end 1334 (FIG. 76). As can be seen in FIG. 76, the distal end 1334 may have a sharpened cutting surface 1336 thereon. As can also be seen in FIGS. 74-76, in some embodiments, the blade 200 may have a curved blade tip 1360 that has a pair of lateral cutting edges 1362 formed thereon. In other embodiments, the blade tip 1360 may be straight. In some embodiments, the blade 200 may be rotated in the various manners discussed above. In other embodiments, the blade 200 may not rotate. In such embodiments, for example, the clinician may choose not to activate the motor for rotating the blade or the handpiece may comprise a handpiece that does not include a motor for rotating the blade.

Figure 74:
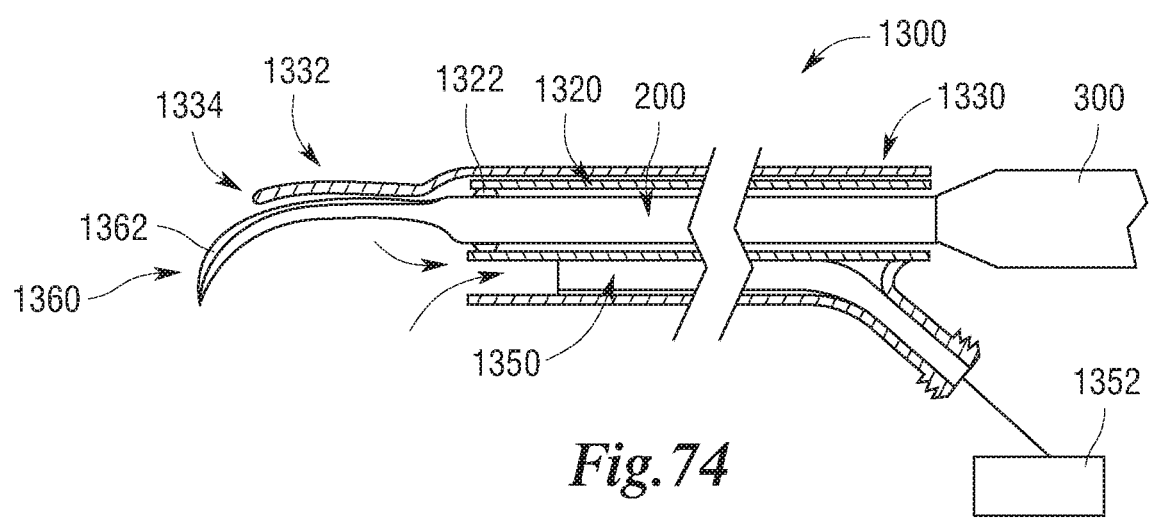
FIG. 74 is a partial side cross-sectional view of another non-limiting surgical instrument embodiment.
Figure 75:
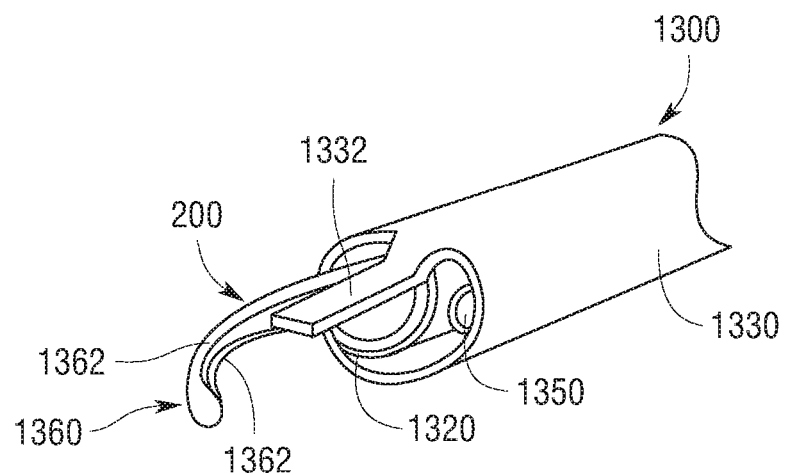
FIG. 75 is a perspective view of a portion of the outer sheath and blade arrangement employed with the surgical instrument embodiment depicted in FIG. 74.

In use, the swing arm portion 1332 may cover portions of the distal end 1360 of the blade 200. In one mode of use, the outer sheath 1330 is retained in position wherein the swing arm portion 1332 covers the back side of the blade 200 as shown in FIG. 74. Such arrangement leaves the curved blade tip 1360 exposed. When in such position, for example, the curved blade tip 1360 could be employed to transect tissue, such as the meniscus. In a second mode of operation, the swing arm portion 1332 is moving.

In the embodiment depicted in FIGS. 74-77, a suction tube 1350 is employed to draw loose tissue towards the blade tip 1360 and also remove small sections of transected tissue during cutting. In other embodiments, suction could occur in the annular space between the sheaths 1320, 1330. In still other embodiments, the blade 200 may have a suction path (not shown) extending therethrough which ultimately communicates with a source of suction as was described above. Such suction path would most likely exit the blade 200 at the node at the proximal end. In still other embodiments, no suction is employed.

In some embodiments, the swing arm portion 1332 may be permanently retained in position against the blade 200. In still other embodiments, a lubricious or low friction pad (not shown) may be mounted to the swing arm portion 1332 such that the pad contacts the blade 200. In other embodiments, a 0.002"-0.010" clearance may be provided between the swing arm portion 1332 and the blade 200. In other embodiments, the swing arm portion 1332 extends around the length of the curved portion of the blade 200 so that the entire blade 200 is covered from the back side.

The various non-limiting embodiments described hereinabove may be effectively employed in a connection with a variety of different surgical applications and are particularly well-suited for cutting and coagulating tissue in the aqueous environment of arthroscopic surgery. In such applications, however, if fluid passes between the blade or waveguide and the inner sheath, the fluid may enter the housing and damage the components therein. Various sealing arrangements are known for use with ultrasonically powered surgical instruments. For example, U.S. Pat. Nos. 5,935,144 and 5,944,737, the disclosures of which are each herein incorporated by reference in their respective entireties, each disclose various sealing arrangement for use with ultrasonic surgical instruments in the traditional environment of laparoscopic surgery and open surgery (i.e., non-aqueous environments). However, various non-limiting embodiments discussed below employ improved sealing arrangements that may be better suited for use in aqueous environments.

Figure 78:
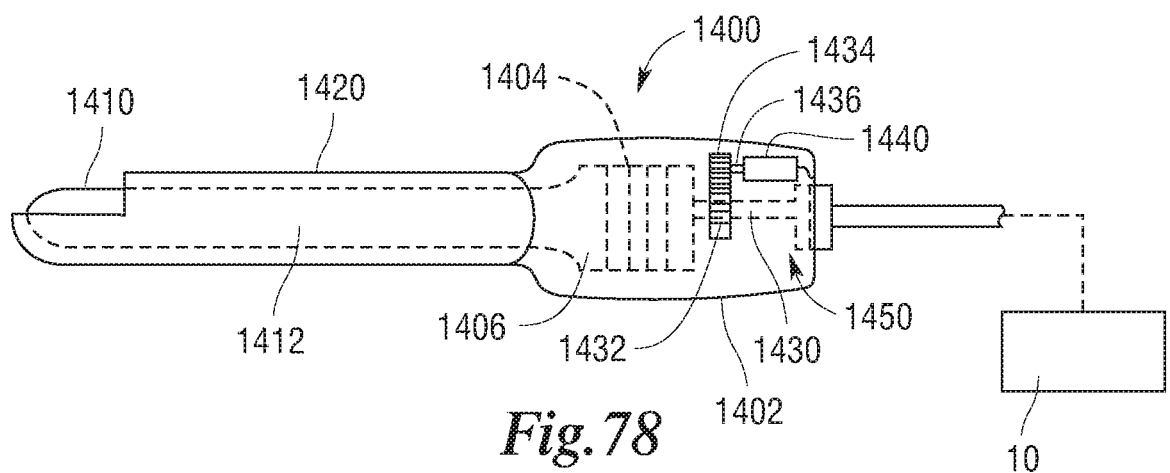
FIG. 78 is a side view of another non-limiting ultrasonic surgical instrument embodiment.

More particularly and with reference to FIG. 78, there is shown an ultrasonic device 1400 that includes a housing 1402 that rotatably supports an ultrasonic transducer assembly 1404 therein. For example, the ultrasonic transducer assembly 1404 may be rotatably supported within the housing 1402 by a series of bearings (not shown). An ultrasonic horn 1406 may be coupled to the ultrasonic transducer assembly 1404 and an ultrasonic implement 1410 is attached thereto by conventional means which may typically comprise a threaded arrangement. As used herein, the term "ultrasonic implement" may encompass any one of the blade and cutting member embodiments described herein. The portion of the ultrasonic implement 1410 that is coupled to the ultrasonic horn 1406 may be referred to as a waveguide portion 1412. The waveguide 1412 may comprise an integral portion of the ultrasonic implement 1410 or it may comprise a separate component attached thereto by, for example, a threaded connection. In the embodiment depicted in FIG. 78, the ultrasonic implement 1410 extends through a hollow outer sheath 1420. The outer sheath 1420 and the distal end of the ultrasonic implement 1410 may be configured in any one of the various blade and sheath configurations described hereinabove as well as others.

As can also be seen in FIG. 78, a proximal shaft 1430 is attached to the ultrasonic transducer assembly 1404. Attached to the proximal shaft 1430 is a driven gear 1432 that is in meshing engagement with a drive gear 1434 coupled to an out put shaft 1436 of a motor 1440. Ultrasonic electrical signals and the motor control signals may be supplied from the control system 10 through a slip ring assembly 1450 of the type and construction described above. The device 1400 may further comprise the various control button arrangements described above, so that the device may be used in an ultrasonic mode, a non-ultrasonic mode (e.g., rotational shaving mode) and a combination of such modes. Unlike the various instruments described above, the motor 1440 is not coaxially aligned with the ultrasonic transducer assembly.

Figure 79:
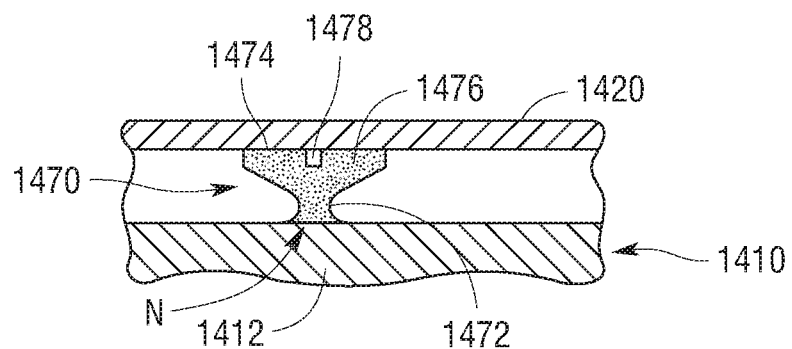
FIG. 79 is a partial cross-sectional view of a non-limiting seal embodiment between a hollow sheath and a waveguide portion of an ultrasonic implement embodiment.

FIG. 79 depicts a non-limiting embodiment of a seal assembly 1470 that may be employed between in the waveguide or proximal portion 1412 of the ultrasonic implement 1410 and the outer sheath 1420. The seal 1470 comprises an annular member that may be fabricated from silicon or other materials such as, for example, Ultem® and is over molded or otherwise sealingly attached to the waveguide 1412 at a node "N". The seal 1470 may have a first annular seal portion 1472 that is molded onto the waveguide 1412 at a node "N" and two axial seal portions 1474, 1476 that extend axially in opposite axial directions beyond the first annular seal portion 1472 and which are separated by a groove 1478. The groove 1478 may enable the two axial seal portions 1474, 1476 to somewhat flex relative to each other in sealing contact with the outer sheath 1420. The narrower first annular seal portion 1472 may avoid excessive heat build-up while providing a wider contact area wherein the seal 1470 contacts the outer sheath 1420.

Figure 80:
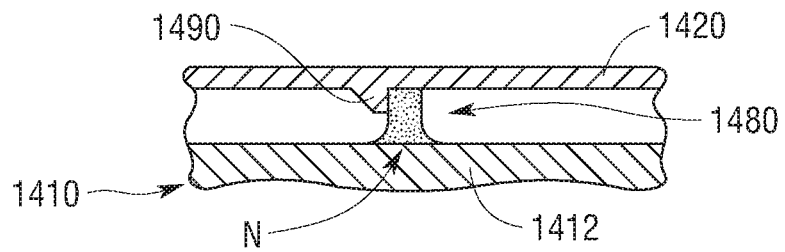
FIG. 80 is a partial cross-sectional view of another non-limiting seal embodiment between a hollow sheath and a waveguide portion of an ultrasonic implement embodiment.

FIG. 80 depicts anon-limiting embodiment of a seal 1480 that may be employed between in the waveguide or proximal portion 1412 of the ultrasonic implement 1410 and the outer sheath 1420. The seal 1480 comprises an annular member that may be fabricated from silicon or other materials, such as for example, Ultem® and is over molded or otherwise sealingly attached to the waveguide 1412 at a Node "N". The seal 1480 may be arranged to abut an inwardly-extending annular abutment ring 1490 formed on the outer sheath 1420. The seal 1480 is located distal with respect to the abutment ring 1490. When the fluid pressure builds up within the distal end of the outer sheath 1420, the seal 1480 is forced into the abutment ring 1490 thereby increasing the strength of the seal. The outer sheath 1420 may be fabricated from, for example, stainless steel.

Figure 81:
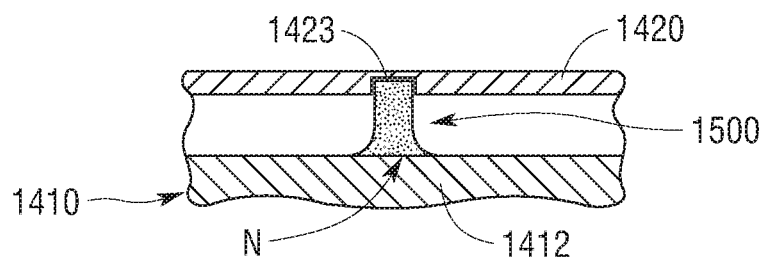
FIG. 81 is a partial cross-sectional view of another non-limiting seal embodiment between a hollow sheath and a waveguide portion of an ultrasonic implement embodiment.

FIG. 81 depicts a non-limiting embodiment of a seal 1500 that may be employed between in the waveguide portion 1412 of the blade 1410 and the outer sheath 1420. The seal 1500 comprises an annular member that may be fabricated from silicon or other materials, such as for example, Ultem® and is over molded or otherwise sealingly attached to the waveguide 1412 at a Node "N". The seal 1480 may be arranged to be received within an annular groove 1423 provided in the outer sheath 1420. The outer sheath 1420 may be fabricated from, for example, stainless steel.

Figure 82:
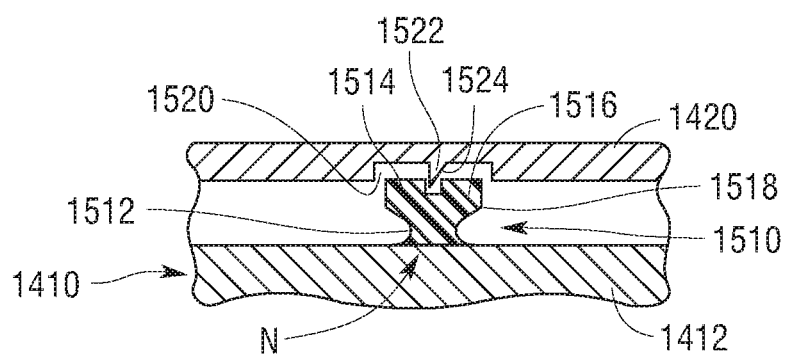
FIG. 82 is a partial cross-sectional view of another non-limiting seal embodiment between a hollow sheath and a waveguide portion of an ultrasonic implement embodiment.

FIG. 82 depicts a non-limiting embodiment of a seal 1510 that may be employed between in the waveguide or proximal portion 1412 of the ultrasonic implement 1410 and the outer sheath 1420. The seal 1510 comprises an annular member that may be fabricated from silicon or other materials such as, for example, Ultem® and is over molded or otherwise sealingly attached to the waveguide 1412 at a node "N". The seal 1510 may have an inner rim portion 1512 that is molded onto the waveguide 1412 at a node "N" and two axial seal portions 1514, 1516 that extend axially in opposite directions beyond the inner portion 1512 and which are separated by a groove 1518. The axial portions 1514, 1516 are sized to extend into a groove 1520 provided in the outer sheath 1420. As can be seen in FIG. 82, the groove 1520 has an inwardly protruding ring 1522 sized to extend into the groove 1518 in the seal 1510. In the illustrated embodiment, the ring 1522 has an angled ramp 1524 formed thereon that permits the seal 1510 to slide over it during assembly, then lock in place. The outer sheath 1420 may be fabricated from, for example, Ultem®.

Figure 83:
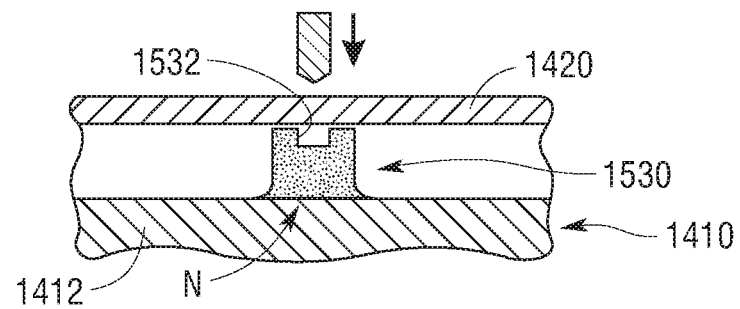
FIG. 83 is a partial cross-sectional view of another non-limiting seal embodiment between a hollow sheath and a waveguide portion of an ultrasonic implement embodiment, prior to being crimped in position.
Figure 84:
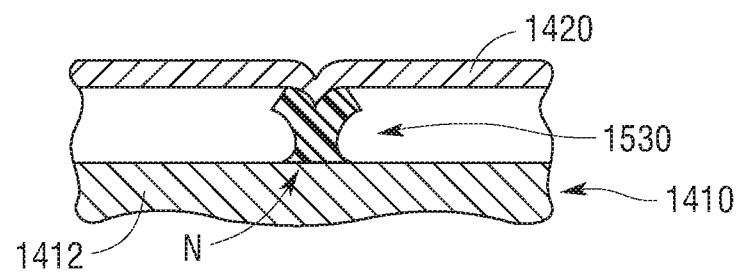
FIG. 84 is a partial cross-sectional view of the seal embodiment of FIG. 83 after being crimped in position.

FIGS. 83 and 84 depict a non-limiting embodiment of a seal 1530 that may be employed between in the waveguide or proximal portion 1412 of the ultrasonic implement 1410 and the outer sheath 1420. The seal 1530 comprises an annular member that may be fabricated from silicon or other materials such as, for example, Ultem® and is over molded or otherwise sealingly attached to the waveguide 1412 at a node "N". The seal 1530 may have a groove 1532 therein as shown in FIG. 83. The outer sheath 1420 is then crimped to thereby crush the seal 1530 as shown in FIG. 84. The outer sheath 1420 could be crimped evenly all the way around the circumference, or it could be crimpled in discrete locations. For example, four evenly spaced (e.g., at 90 degree intervals) crimps may be employed. In such embodiments, the outer sheath 1420 may be fabricated from, for example, stainless steel.

Figure 85:
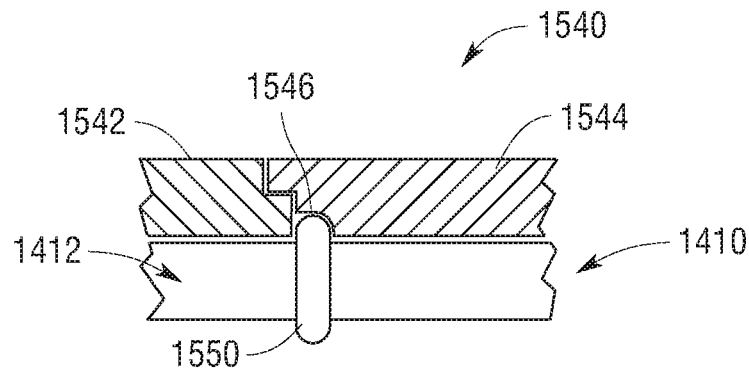
FIG. 85 is a partial cross-sectional view of another non-limiting seal embodiment between a two-piece hollow sheath and a waveguide portion of an ultrasonic implement embodiment.

FIG. 85 depicts a portion of an outer sheath 1540 that has a proximal axial portion 1542 and a distal axial section 1544 that are adapted to be interconnected together by, for example, welding, press fit, threading or snapping together. As can be seen in FIG. 85, the distal axial section 1544 has a groove portion 1546 sized to engage a portion of an annular seal 1550 that is over molded or otherwise sealingly installed on the waveguide or proximal portion 1412 of the ultrasonic implement 1410 at a node "N". Thus, when attached together, the proximal axial section 1542 and distal axial section 1544 serve to trap and compress a portion of the seal 1550 therebetween. In alternative embodiments, the groove portion 1546 may be provided in the proximal axial section 1542 or each section 1542, 1544 may have a groove segment therein that cooperate to accommodate the annular seal 1550 therein.

Figure 86:
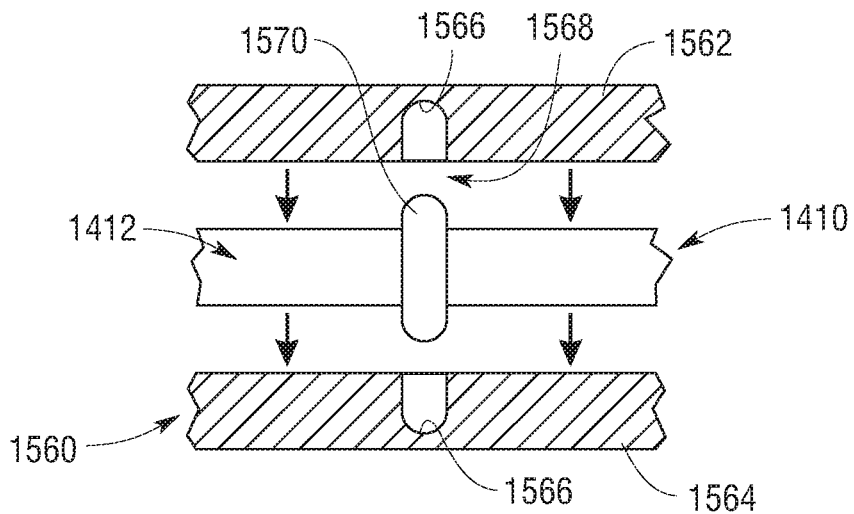
FIG. 86 is a partial cross-sectional exploded assembly view of another non-limiting seal embodiment between another two-piece hollow sheath and a waveguide portion of an ultrasonic implement embodiment.
Figure 87:
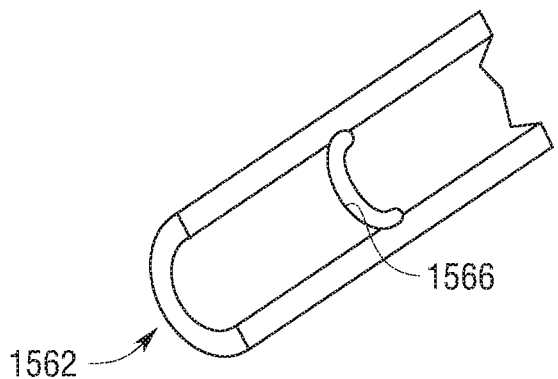
FIG. 87 is a partial perspective view of a portion of the two piece hollow sheath embodiment of FIG. 86.

FIG. 86 depicts a portion of an outer sheath, generally designated as 1560 that consists of two lateral halves 1562, 1564. Each lateral half 1562, 1564 has a semi-annular groove segment 1566 formed therein. See FIG. 87. The semi-annular groove segments 1566 form an annular groove 1568 sized to receive an annular seal 1570 that is over molded onto or otherwise attached to the waveguide or proximal portion 1412 when the lateral halves 1562, 1564 are joined together to form the hollow outer sheath 1560. By creating a two piece outer sheath 1560, the seal 1570 could have much greater interference with the outer sheath 1560, than it generally could have if the waveguide 1412 must be pushed down the outer sheath 1560 during the assembly process. The two outer sheath halves 1562, 1564 may be joined together by welding, snap fitting or other suitable methods. Thus, the seal 1570 may first be installed on the waveguide 1412. Thereafter, the two halves 1562, 1564 may be brought together around the wave guide 1412 such that the seal 1570 is trapped within the groove 1568. The halves 1562, 1564 are then fastened together in that position.

Figure 88:
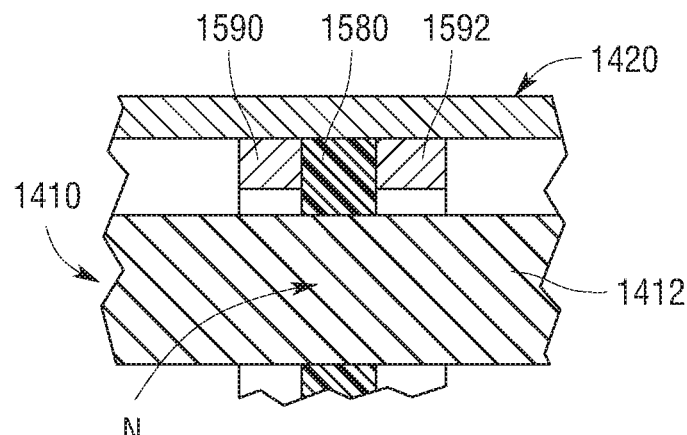
FIG. 88 is a partial cross-sectional view of another non-limiting seal embodiment between a hollow sheath and a waveguide portion of an ultrasonic implement embodiment.

FIG. 88 depicts a non-limiting embodiment of a seal 1580 that may be employed between in the waveguide portion 1412 of the ultrasonic implement and the outer sheath 1420. The seal 1580 comprises an annular member that may be fabricated from silicon or other materials such as, for example, Ultem® and is over molded or otherwise sealingly attached to the waveguide or proximal portion 1412 at a node "N". The seal 1580 may be held in place by a proximal ring 1590 and a distal ring 1592. The proximal ring 1590 may comprise an integral portion of the outer sheath 1420 or it could comprise a separate component that is pressed into the outer sheath 1420 or otherwise attached thereto. The distal ring 1592 may be glued, press fit or otherwise attached to the outer sheath 1420. The distal ring 1592, upon installation, may provide compression on the seal 1580. This would increase the force between the seal 1580 and the waveguide 1412, further decreasing fluid movement past the seal 1580. The rings 1590, 1592 may comprise split annular rings or rings with no splits therein. In addition, as can be seen in FIG. 88 the tings 1590, 1592 may be sized relative to the waveguide 1412 such that an amount of clearance "C" is provided therebetween.

Figure 89:
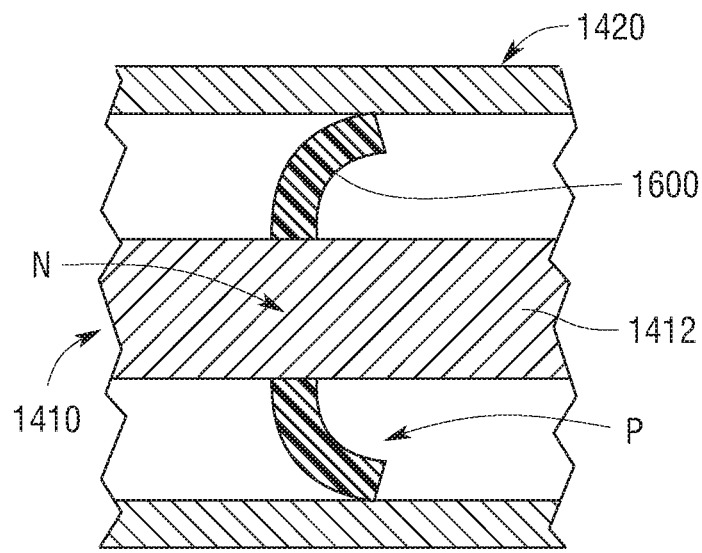
FIG. 89 is a partial cross-sectional view of another non-limiting seal embodiment between a hollow sheath and a waveguide portion of an ultrasonic implement embodiment.

FIG. 89 depicts a non-limiting embodiment of a seal 1600 that may be employed between in the waveguide or proximal portion 1412 of an ultrasonic implement 1410 and the outer sheath 1420. The seal 1600 comprises an annular member that may be fabricated from silicon or other materials such as, for example, Ultem® and is over molded or otherwise sealingly attached to the waveguide 1412 at a node "N". The seal 1600 may have an outer diameter that is greater than the inner diameter of the outer sheath 1420. The seal 1600 may further have a proximal side 1602 and a distal side 1604. When assembled, an outer portion of the proximal side 1602 of the seal 1600 sealingly contacts the inner wall 1421 of the outer sheath 1420. Thus, when fluid pressure "P" builds up on the distal side of the seal 1600, the seal 1600 is further urged into sealing contact with the outer sheath 1420, thereby creating a better seal between the waveguide 1412 and the outer sheath 1420.

Figure 90:
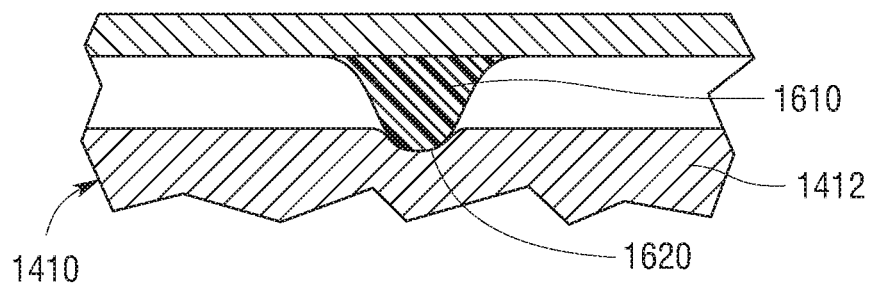
FIG. 90 is a partial cross-sectional view of another non-limiting seal embodiment between a hollow sheath and a waveguide portion of an ultrasonic implement embodiment.

FIG. 90 depicts a non-limiting embodiment of a seal 1610 that may be employed between in the waveguide or proximal portion 1412 of the blade and the outer sheath 1420. The seal 1610 comprises an annular member that may be fabricated from silicon or other materials such as, for example, Ultem® and is molded or otherwise attached to the outer sheath 1420 as shown. In this embodiment, an annular groove 1620 may be provided in the waveguide 1412 for receiving a portion of the seal 1610 therein. In alternative embodiments, no groove is provided. It will be further understood that the seals depicted in FIGS. 79-82 may likewise be attached to the outer sheath instead of the waveguide or proximal portion of the cutting blade or implement as illustrated without departing from the spirit and scope of the various non-limiting embodiments disclosed herein and their respective equivalents. In addition, it will be further understood that the various seal embodiments described herein may be effectively employed with any of the surgical instrument embodiments described above. That is, the various non-limiting seal arrangements disclosed herein and their respective equivalent structures may be effectively employed to achieve a seal between the ultrasonic blade or waveguide and the corresponding inner sheath. In those embodiments that employ an inner sheath and an outer sheath, but do not apply a suction therebetween, the various non-limiting seal arrangements disclosed herein and their respective equivalents may also be effectively employed to achieve a substantially fluid-tight seal between the inner and outer sheaths. In yet other non-limiting embodiments, the seal may be employed between an ultrasonic blade and an outer sheath wherein the ultrasonic blade does not engage in gross-rotational motion relative to the outer sheath. In such embodiments, the seal may be rigidly attached to the ultrasonic blade and the outer sheath. In still other non-limiting embodiments, the ultrasonic blade may oscillate within the outer sheath. For example the ultrasonic blade may oscillate through a 90 degree arc (45 degrees on each side of a central axis). In such embodiments, the seal may be rigidly attached to the outer sheath and ultrasonic blade by, for example, adhesive, crimping, etc. The seal material may comprise an elastic rubber material or the like that would accommodate twisting of the seal for a range of ±45 degrees. In such embodiments, the stretch experienced by the seal may help to return the blade to a neutral position of zero degrees (in alignment with the central axis).

Various of the above-described embodiments employ rotating blades that serve to shear off tissue between cutting edges formed on the blade and edges of the surrounding outer sheath. While such arrangements are very effective in cutting most tissues, tough tissue, such as tendon tissue for example, can be difficult to effectively cut because it can tend to "milk" between the blade and the outer sheath. Such problem is akin to problems encountered when scissors are used to cut through a tough material such as leather, for example. In short, the scissor blades separate and the material does not get cut. This phenomenon is graphically depicted in FIGS. 91A-D. As can be seen in those Figures, two cutting blades 1700 are employed to cut through tough tissue "T". As the blades 1700 move inward toward the tissue "T", the tissue "T" moves between the blades 1700 and causes them to separate.

In various blade and sheath embodiments disclosed herein, it may be advantageous to minimize the amount of clearance between the cutting portion of the outer sheath and the cutting edge(s) of the blades. For example, it may be desirable to maintain the amount of clearance between the cutting portion of the outer sheath and the cutting edge(s) on the blades within the range of 0.001" to 0.005". In other non-limiting embodiments, one cutting edge or portion is harder than the other cutting portion. For example, the cutting edge(s) on the blades may be harder than the cutting portion of the outer sheath or visa versa. The motor may then be activated with or without ultrasound to achieve a near zero clearance between the cutting edges/portion. In addition to such approaches or in place of such approaches, other embodiments may employ structure to bias at least a distal portion the blade in an "off-center" arrangement within the outer sheath while still facilitating the rotation of the blade therein. More particularly and with reference to FIGS. 92-93, there is shown a blade 200 of the type and construction described above, extending through an outer sheath assembly 3000. In the depicted embodiment, the outer sheath assembly 3000 is used in connection with a surgical instrument 3001 that may be constructed in any of the manners described above to selectively apply gross rotational motion to the blade 200 as well as to selectively apply ultrasonic motion thereto.

In the embodiment depicted in FIG. 93, the blade 200 extends axially through an inner sheath 3020 that is mounted within a portion of the instrument housing 3010. The outer sheath assembly 3000 is attached to the instrument housing 3010 and has a distal tip portion 3002 that has a window or opening 3004 therein. As discussed above, the window 3004 enables tissue to be drawn into a tip cavity 3006 formed within the distal tip portion 3002. Suction may be applied to the tip cavity 3006 through a suction port 3007 in the distal tip portion 3002 of the outer sheath assembly 3000 that communicates with a source of suction 244. In these embodiments, the blade 200 is somewhat flexible and may be fabricated from, for example, Titanium. In addition, the waveguide portion or proximal portion of blade 200 extends through a bushing 3030 that is mounted within the inner sheath 3020 in the location of node "N". In various embodiments, the inner sheath 3020 may be fabricated from material that is substantially rigid and resists bending. For example, the inner sheath 3020 may be fabricated from Ultem or similar materials. The bushing 3030 may be fabricated from, for example Ultem® and be non-rotatably retained within the inner sheath 3020 by, for example, stainless steel.

As can be seen in FIGS. 92A and 93, the waveguide or proximal portion 701 of blade 200 extends through a hole 3032 in the bushing 3030. The centerline CL-CL of the bushing hole 3032 is offset (i.e., not coaxial with) from the central axis A-A defined by the outer sheath 3000. The bushing hole 3032 is sized relative to the proximal portion 701 of the blade 200 to permit the proximal portion 701 to rotate freely therein, yet also serves to bias the distal end portion 700 of the blade 200 off the center axis A-A of the outer sheath 3000 such that the tissue cutting distal end 705 of the blade 200 is retained in rotatable contact with the cutting edge 3005 defined by the window opening 3004. In some embodiments, for example, the blade 200 may be biased off center a distance that can be as much as 0.030". Because the tissue cutting distal end 705 of the blade 200 is biased in such a manner, the distal end 705 resists forces encountered when cutting tough tissue which may otherwise cause cutting edges 706 on the distal end 705 to move away from the cutting edge 3005 of the window opening 3004.

Figure 94:
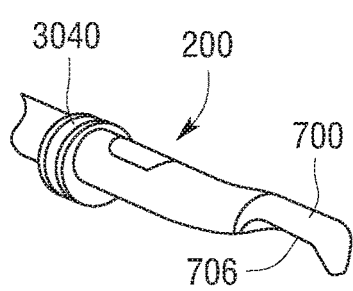
FIG. 94 is a perspective view of a portion of another non-limiting cutting blade and bushing embodiment.
Figure 95:
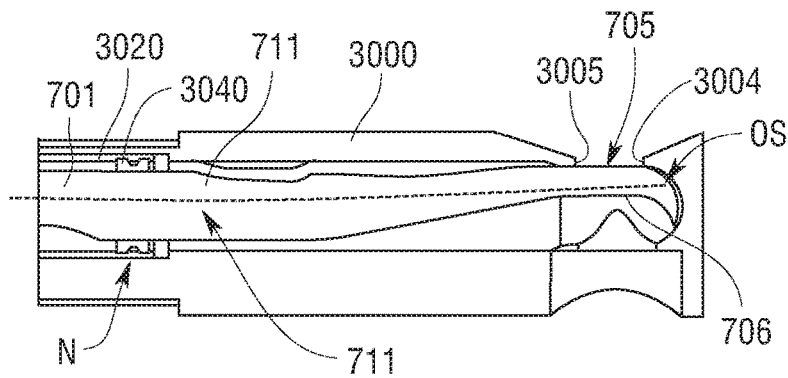
FIG. 95 is a cross-sectional view of a portion of the blade and bushing embodiment of FIG. 94 in a non-limiting surgical instrument embodiment.

FIGS. 94 and 95 illustrate another embodiment wherein a proximal portion 701 of the blade 200 coaxially extends through a bushing 3040 that may be fabricated from, for example, silastic silicone or Ultem® and be retained within the inner sheath 3020 by, for example, a slip fit. As with the above embodiment, the bushing 3040 may be located at the node "N" along the waveguide or proximal portion of the blade 200. However, in this embodiment, the distal portion 711 (i.e., the portion of the blade 200 that extends distally from the bushing 3040) is bent slightly to bias the tissue cutting distal end 705 of the blade 200 into the cutting edge 3005 of the window opening 3004. For example, the distal portion 711 of the blade 200 may be bent approximately 0.030 inches off-center (distance OS in FIG. 95). Such arrangement causes the tissue cutting distal end 705 of the blade 200 to resist forces when cutting tough tissue which may otherwise cause cutting edges 706 on the blade 200 to move away from the cutting edge 3005 of the window opening 3004.

Figure 96:
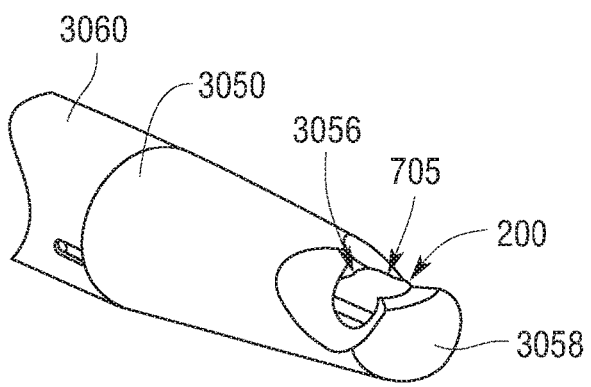
FIG. 96 is a partial perspective view of a portion of a non-limiting blade and outer sheath embodiment.
Figure 97:
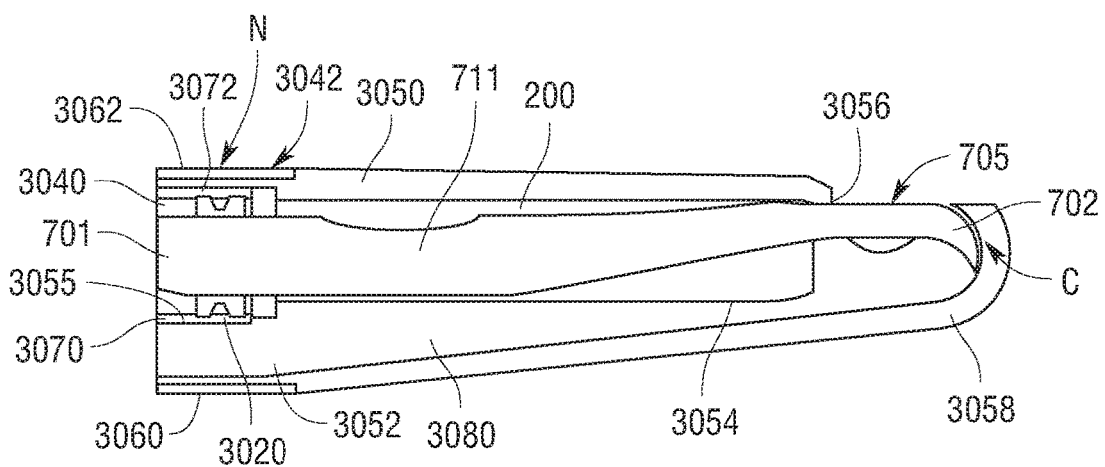
FIG. 97 is a cross-sectional view of the blade and outer sheath arrangement of FIG. 96.

FIGS. 96-97 depict another non-limiting outer sheath 3040 and blade 200 embodiment. In this embodiment, a distal outer sheath tip 3050 is employed. The distal outer sheath tip 3050 may be fabricated from metal such as, for example, stainless steel and have a proximal bearing portion 3052 that extends into an open distal end 3062 of the outer sheath 3060. The outer sheath 3060 may be fabricated from, for example, stainless steel and may be attached to the distal outer sheath tip 3050 by fasteners, adhesive, etc. The proximal end 3062 of the outer sheath 3060 is attached to a portion of an instrument housing as was described above. The instrument may comprise many of the various instrument embodiments described in detail above that supplies gross rotational motion to the blade 200 as well as ultrasonic motions thereto.

The waveguide or proximal portion 701 of the blade 200 may be attached to an ultrasonic horn (not shown) and extend through an inner sheath 3070 in the various manners described above. The proximal portion 701 of the blade 200 may be rotatably supported within the inner sheath 3070 by a bushing 3040 as was described above. A distal portion 711 of the blade 200 rotatably extends through a lumen 3054 in the distal outer sheath tip 3050. See FIG. 97. A window 3056 is formed in the distal outer sheath tip 3050 to expose the tissue cutting distal end 705 of the blade 200. As with various embodiments described above, the window 3056 may define at least one cutting edge 3057 that interacts with the rotating tissue cutting distal end 705 of blade 200 to cut tissue drawn into the window 3056. In this embodiment, the outer diameter "OD" of the tissue cutting distal end portion 705 of the blade 200 at the point wherein the distal end 705 of the blade 200 protrudes distally into the window opening 3056 is greater than the inner diameter "ID" of the lumen 3054. In some embodiments, for example, the inner lumen diameter "ID" may be approximately 0.140" and the blade "OD" may be approximately 0.150". Such arrangement results in an interference between the tissue cutting distal end 705 of the blade 200 and the distal outer sheath tip 3050. In such arrangement, the distal portion 711 of the blade 200 essentially comprises a cantilevered beam which results in the tissue cutting distal end 705 of the blade 200 being pushed downward (FIG. 97) by the distal outer sheath tip 3050.

In the embodiments depicted in FIGS. 92-97, it may be desirable to provide an amount of clearance between the distal end 3058 of the distal outer sheath tip 3050 and the curved tip portion 702 of the blade 200. This clearance "C" is illustrated in FIG. 97. Such clearance allows unimpeded ultrasonic motion of the blade 200. However, it may be desirable to minimize such clearance "C" to reduce suction loses around the curved tip portion 702 which may hamper the device's ability to cut tissue.

Figure 98:
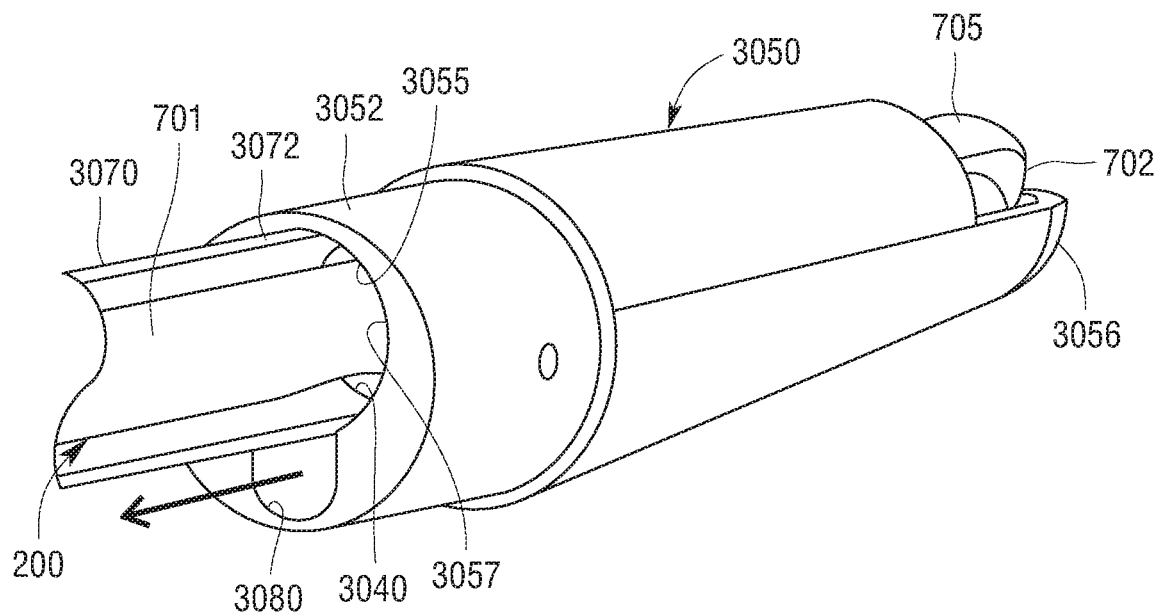
FIG. 98 is a partial rear perspective view of a portion of the outer sheath and blade arrangement of FIG. 97.
Figure 99:
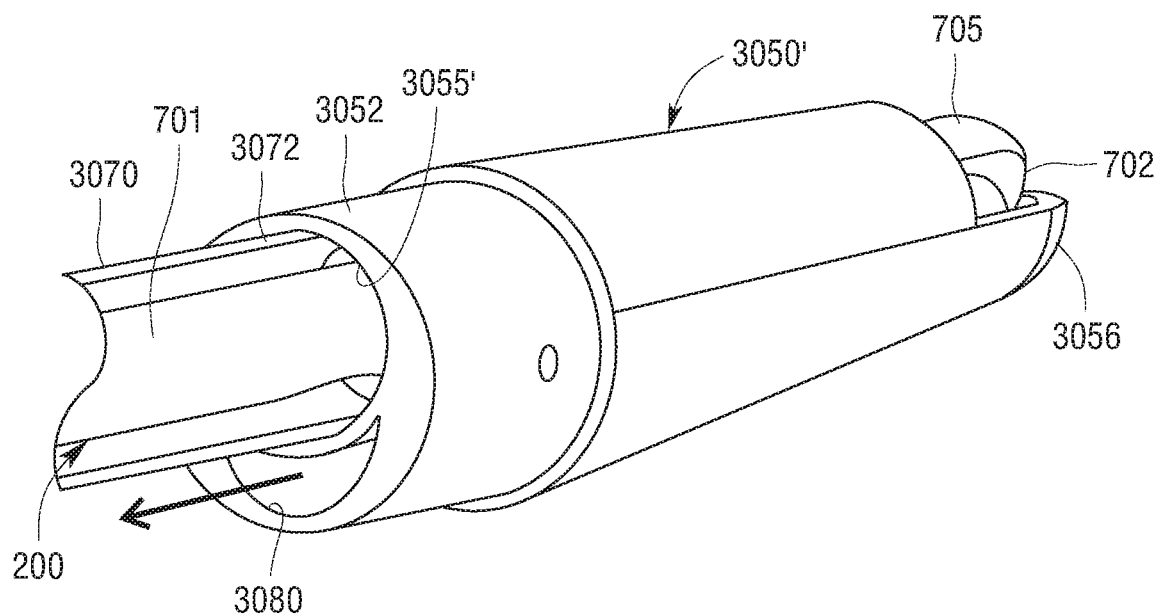
FIG. 99 is a partial rear perspective view of a portion of another non-limiting outer sheath and blade embodiment.

Also, to facilitate the drawing of tissue into the window opening 3056, suction must be applied within the distal outer sheath tip 3050 from a source of suction (not shown) in the various manners described above. In this embodiment, for example, a suction path 3080 is provided in the distal outer sheath tip 3050 as shown in FIGS. 97 and 98. A seal 3090 is journaled on the distal portion 711 of the blade 200 to establish a fluid tight seal at a point wherein the distal portion 711 of the blade 200 exits the inner sheath 3070. See FIG. 97. Also in this embodiment, the distal end 3072 of the inner sheath 2070 extends into an opening 3055 in the bearing portion 3052 of the distal outer sheath tip 3050 to provide relative rigid support thereto. As can be seen in FIG. 98, the suction path 3080 forms a discontinuity in the inner sheath support surface 3057 defined by opening 3055. FIG. 99 depicts an alternative distal outer sheath tip 3050' wherein the suction path 3080' does not extend into the opening 3055' that supports the distal end 3072 of the inner sheath 3070.

Various ultrasonic surgical instruments that employ an outer sheath and rotatable cutting member arrangement also face the challenge of outer sheath and blade deformation due to heat and high contact forces between those two components. Deformation of the distal tip portion of the outer sheath can be reduced by changing the tip material to metal, but this can result in the undesirable effect of damaging the blade via galling, which can ultimately result in broken blades and extremely limited blade life. Such sheath tip blade galling damage can occur due to metal-to-metal contact between the blade and the sheath tip. This condition may be exacerbated when cutting tough tissues such as tendon and the like. As was discussed above, such tough tissues may bias the cutting edges away from each other and force the opposite cutting edge or face of the blade into contact with the sheath tip, thereby resulting in galling.

Figure 100:
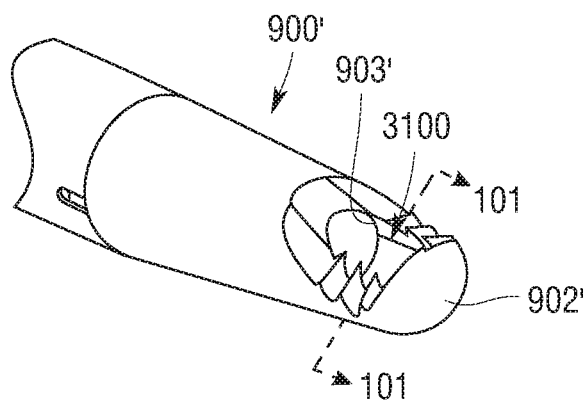
FIG. 100 is a partial perspective view of another non-limiting outer sheath embodiment.
Figure 101:
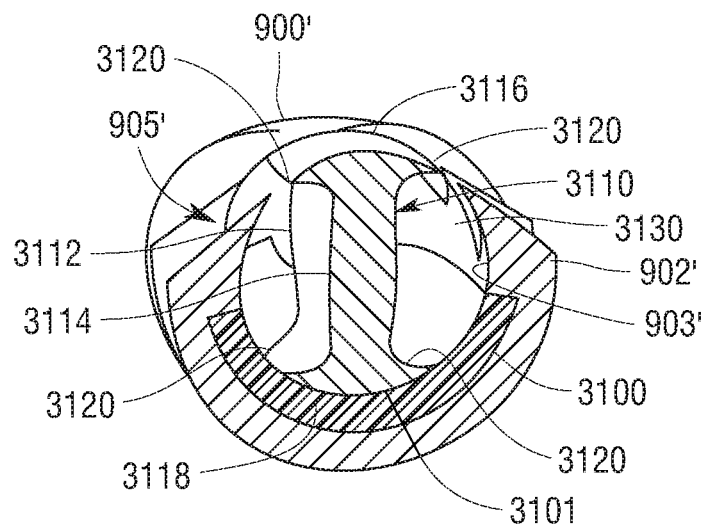
FIG. 101 is a cross-sectional end view of the outer sheath embodiment of FIG. 100 supporting a cutting blade embodiment therein.

Various non-limiting embodiments described herein and their respective equivalents may employ a thin friction-reducing material on the inner wall of the tip cavity formed within the distal tip portion of the outer sheath or, in alternative embodiments, a low friction or friction reducing pad may be affixed within the tip cavity to protect the blade. One exemplary embodiment is depicted in FIGS. 100 and 101. As can be seen in those Figures, the outer sheath 900' that was described above has a friction-reducing polymeric coating or pad 3100 therein. In various embodiments, the distal tip portion 902' of the sheath 900' may be fabricated from metal such as stainless steel and the friction reducing material or pad 3100 may be fabricated from, for example, polyimide, carbon-filled polyimide, Teflon®, Teflon-Ceramic, etc. In those embodiments in which a pad is employed, the pad may be affixed within the tip portion 902' by, for example, adhesive or a dovetail joint arrangement. The pad 3100 is preferably configured to match the corresponding geometry of the blade. For example, as shown in FIG. 101, a blade 3110 that may be substantially similar to blade 200 described above, has a distal end portion 3112 that has a central portion 3114 that separates two cutting faces 3116, 3118. The cutting faces 3116, 3118 have an arcuate shape and have cutting edges 3120 formed on each edge thereof. In that embodiment, the polymeric pad 3100 also has a similar arcuately shaped upper surface 3101. The advantage of this concept is that it maintains a hard metallic cutting edge (e.g., stainless steel), which is advantageous for cutting tough tissue. It also protects the broad cutting faces 3116, 3118 of the blade 200 when the pad 3100 is fabricated from softer materials that can otherwise support the forces applied to the blade. In addition or in the alternative, the inner wall 903' of the tip portion 902' may be coated with a friction-reducing coating 3130 of the type described above. The coating 3130 may comprise a separate component that is held in place via adhesive or it may comprise a deposition coating that is directly adhered to the inner surface 903' of the tip portion 902'. For example, a Teflon® material may be applied to portions of the inner wall 903' through vapor deposition. The portions of the tip 902' wherein the coating is not needed may be masked off using known masking techniques before exposing the tip 902' to the vapor deposition process.

Figure 102:
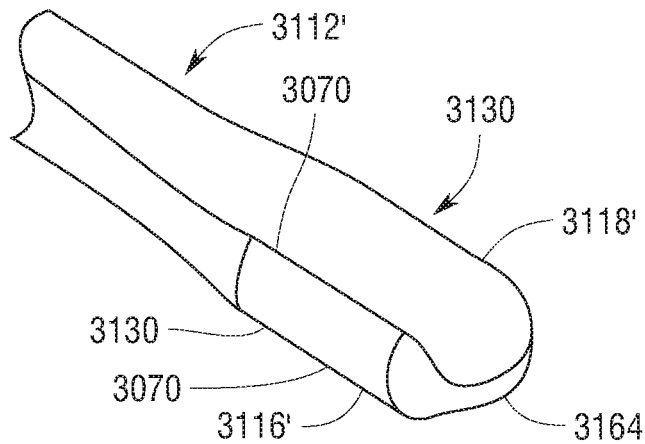
FIG. 102 is a perspective view of a portion of another non-limiting blade embodiment.

FIG. 102 depicts a tissue cutting blade end 3112' that may be coated with a relatively hard, low-friction material to increase surface hardness and reduce friction. In particular, as can be seen in that Figure, at least portions of the cutting faces 3116', 3118' are coated with the coating material 3130. In some embodiments, for example, the coating material may comprise coating materials such as Titanium Nitride, Diamond-Like coating, Chromium Nitride, Graphit iC™, etc. The blade 3060' may be employed in connection with an outer sheath tip that is fabricated from metal (e.g., stainless steel) in order to avoid blade galling and eventual blade breakage. In alternative embodiments, the entire distal tissue cutting end of the blade may be coated with the coating material 3130.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Sterilization can also be done by any number of ways known to those skilled in the art including beta or gamma radiation, ethylene oxide, and/or steam.

In various embodiments, an ultrasonic surgical instrument can be supplied to a surgeon with a waveguide and/or end effector already operably coupled with a transducer of the surgical instrument. In at least one such embodiment, the surgeon, or other clinician, can remove the ultrasonic surgical instrument from a sterilized package, plug the ultrasonic instrument into a generator, as outlined above, and use the ultrasonic instrument during a surgical procedure. Such a system can obviate the need for a surgeon, or other clinician, to assemble a waveguide and/or end effector to the ultrasonic surgical instrument. After the ultrasonic surgical instrument has been used, the surgeon, or other clinician, can place the ultrasonic instrument into a sealable package, wherein the package can be transported to a sterilization facility. At the sterilization facility, the ultrasonic instrument can be disinfected, wherein any expended parts can be discarded and replaced while any reusable parts can be sterilized and used once again. Thereafter, the ultrasonic instrument can be reassembled, tested, placed into a sterile package, and/or sterilized after being placed into a package. Once sterilized, the reprocessed ultrasonic surgical instrument can be used once again.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

All of the above U.S. Patents and U.S. Patent applications, and published U.S. Patent Applications referred to in this specification are incorporated herein by reference in their entirety, but only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ultrasonic surgical instrument, comprising:
    a housing;
    an ultrasonic transducer assembly to selectively generate ultrasonic motion, wherein the ultrasonic transducer assembly is rotatably supported within the housing;
    a motor within the housing, wherein the motor is configured to selectively apply a rotary motion to the ultrasonic transducer assembly;
    an outer sheath coupled to the housing, wherein the outer sheath comprises a distal tip portion defining a tip cavity; and
    a blade operably coupled to the ultrasonic transducer assembly and rotatably supported within the outer sheath for rotation with the ultrasonic transducer assembly, wherein the blade includes a tissue-cutting distal end rotatably supported within the tip cavity, and wherein a portion of the tissue-cutting distal end is configured to apply the ultrasonic motion to tissue.

2. The ultrasonic surgical instrument of claim 1, wherein the tip cavity comprises a friction reducing material, and wherein the friction reducing material is applied to at least one of:
    an inner wall of the tip cavity; or
    a portion of the tissue-cutting distal end.

3. The ultrasonic surgical instrument of claim 1, wherein the tissue-cutting distal end comprises a curved segment, and wherein a cutting edge is defined on each lateral side of the curved segment.

4. The ultrasonic surgical instrument of claim 1, wherein the outer sheath defines a distal aperture configured to expose the tissue-cutting distal end.

5. The ultrasonic surgical instrument of claim 4, wherein the tissue-cutting distal end is configured to cut tissue drawn into the distal aperture.

6. The ultrasonic surgical instrument of claim 1, wherein the tissue-cutting distal end is selectively:
    rotatable without applying the ultrasonic motion;
    rotatable while applying the ultrasonic motion; and
    non-rotatable while applying the ultrasonic motion.

7. The ultrasonic surgical instrument of claim 1, wherein the ultrasonic transducer assembly is rotatable to a predetermined position for the portion of the tissue-cutting distal end to apply the ultrasonic motion to the tissue.

* * * * *